United States Patent
Song et al.

(10) Patent No.: US 12,037,647 B2
(45) Date of Patent: Jul. 16, 2024

(54) COMPOSITIONS AND METHODS FOR DETECTING PANCREATIC CANCER

(71) Applicant: THE JOHNS HOPKINS UNIVERSITY, Baltimore, MD (US)

(72) Inventors: Jin Song, Baltimore, MD (US); Zhen Zhang, Dayton, MD (US); Daniel Wan-yui Chan, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 17/013,989

(22) Filed: Sep. 8, 2020

(65) Prior Publication Data

US 2021/0230704 A1    Jul. 29, 2021

Related U.S. Application Data

(63) Continuation of application No. 16/737,084, filed on Jan. 8, 2020, now abandoned, and a continuation of application No. 15/747,780, filed as application No. PCT/US2016/043833 on Jul. 25, 2016, now abandoned.

(60) Provisional application No. 62/197,946, filed on Jul. 28, 2015.

(51) Int. Cl.
*G01N 33/00* (2006.01)
*C07K 14/47* (2006.01)
*C12Q 1/6886* (2018.01)
*G01N 33/574* (2006.01)

(52) U.S. Cl.
CPC ........ *C12Q 1/6886* (2013.01); *C07K 14/4748* (2013.01); *G01N 33/57438* (2013.01); *C12Q 2600/158* (2013.01)

(58) Field of Classification Search
CPC ............ C12Q 1/6886; C12Q 2600/158; C07K 14/4748; G01N 33/57438
See application file for complete search history.

(56) References Cited

PUBLICATIONS

Simeone et al, Pancreas 34:436;443, 2007, IDS 11, Nov. 4, 2020 (Year: 2007).*
Fitori et al, Can Cell International 5:1-8, Feb. 2005, IDS #3, Nov. 4, 2020 (Year: 2005).*
Koopmann et al (Clin Cancer Res 12: 442-446, 2006, IDS #6, Nov. 4, 2020 (Year: 2006).*
Kosanam et al, Mole and Cell proteomic 12: 2820-32. 2013, IDS #7, Nov. 4, 2020(Year: 2013).*
Liao et a, Pancreas 2009, 38:422-426, IDS #9, Nov. 4, 2020 (Year: 2009).*
Weber et al (Cancer Genomics and proteomics 8:263-288 2011 (Year: 2011).*
Soikkeli et al (American J Pathology 177: 387-403, 2010 (Year: 2010).*
Pan et al (J Proteome Res 10: 2359-2376, 2011) (Year: 2011).*
Ballehaninna, U., "Biomarkers for pancreatic cancer: promising new markers and options beyong CA 19-9" Tumor Biol. (2013) DOI 10.1007/s13277-013-1033-3, pp. 1-14.
Benton, W., et al., "Screening Agt recombinant clones by hybridization to single plaques in situ" Science (1977) vol. 196, pp. 180-182.
Fitori, J., et al., "Melanoma inhibitory activity (MIA) increases the invasiveness of pancreatic cancer cells", Cancer Cell International (2005) vol. 5, No. 3.
Grunstein, M., et al., "Colony hybridization: a method for the isolation of cloned DNAs that contain a specific gene" Proc. Nat. Acad. Sci., (1975) vol. 72, No. 10, pp. 3961-3965.
Kimmel, A., "Identification and characterization of specific clones: strategy for confirming the validity of presumptive clones", Methods in Enzymology (1987) vol. 152.
Koopmann, J., et al., "Evaluation of osteopontin as biomarker for pancreatic adenocarcinoma", Cancer Epidemiology, Biomarkers & Prevention, (2004) vol. 13, No. 3.
Kosanam, H., et al., "Laminin, gamma 2 (LAMC2): a promising new putative pancreatic cancer biomarker identified by proteomic analysis of pancreatic adenocarcinoma tissues", Molecular & Cellular Proteomics (2013) 12:10.1074/mcp.m112.023507, pp. 2820-2832.
Li, C., et al., "A multiplexed bead assay for profiling glycosylation patterns on serum protein biomarkers of pancreatic cancer", Electrophoresis, (2011) vol. 32, No. 15, pp. 2028-2035.
Liao, W., et al., "Serum heat shock protein 27 is increased in chronic pancreatitis and pancreatic carcinoma" Pancreas (2009) vol. 38, No. 4, pp. 422-426.
Wahl, G., et al., "Molecular hybridization of immobilized nucleic acids: theoretical concepts and practical considerations" Methods in Enzymology (1987) vol. 152.
Simeone, D., et al., "CEACAM1, a Novel Serum Biomarker for Pancreatic Cancer" Pancreas (2007) vol. 34, No. 4, pp. 436-443.
"Serum markers in patients with resectable pancreatic adenocarcinoma: macrophage inhibitory cytokine I versus CA19-9", Koopmann J, Rosenzweig CN, Zhang Z et al., Clinical cancer research, vol. 12, No. 2, pp. 442-446.
"Molecular Analysis of Precursor Lesions in Familial Pancreatic Cancer", Cmogorac-Jurcevic T, Chelala C, Barry S et al., PLoS One, vol. 8, No. 1, pp. 1-14.
"Periostin, a matrix specific protein, is associated with proliferation and invasion of pancreatic cancer," Ben QW, Jin XL, Liu J et al., Oncol Rep, vol. 25, No. 3, pp. 709-716.

(Continued)

*Primary Examiner* — Lei Yao
(74) *Attorney, Agent, or Firm* — Fox Rothschild LLP

(57) ABSTRACT

Provided herein are methods of detecting pancreatic cancer in a subject, the method comprising measuring in a sample from the subject a level of CA19-9 polysaccharide relative to a reference, and a level of a polynucleotide or polypeptide of at least one marker selected from the group consisting of: OPN, MIA, CEACAM-1, MIC-1, SPON1, HSP27, POSTN, and LGALS3BP relative to a reference, wherein an increased level of the CA19-9 polysaccharide relative to a reference and an increased level of the polynucleotide or polypeptide relative to a reference indicates presence of pancreatic cancer in the subject.

4 Claims, 15 Drawing Sheets

Specification includes a Sequence Listing.

(56) References Cited

PUBLICATIONS

"Quantitative Glycoproteomics Analysis Reveals Changes in N-Glycosylation Level Associated with Pancreatic Ductal Adenocarcinoma", Pan S, Chen R, Tamura Y et al., J Proteome Res, vol. 13, No. 3, pp. 1293-1306.

\* cited by examiner

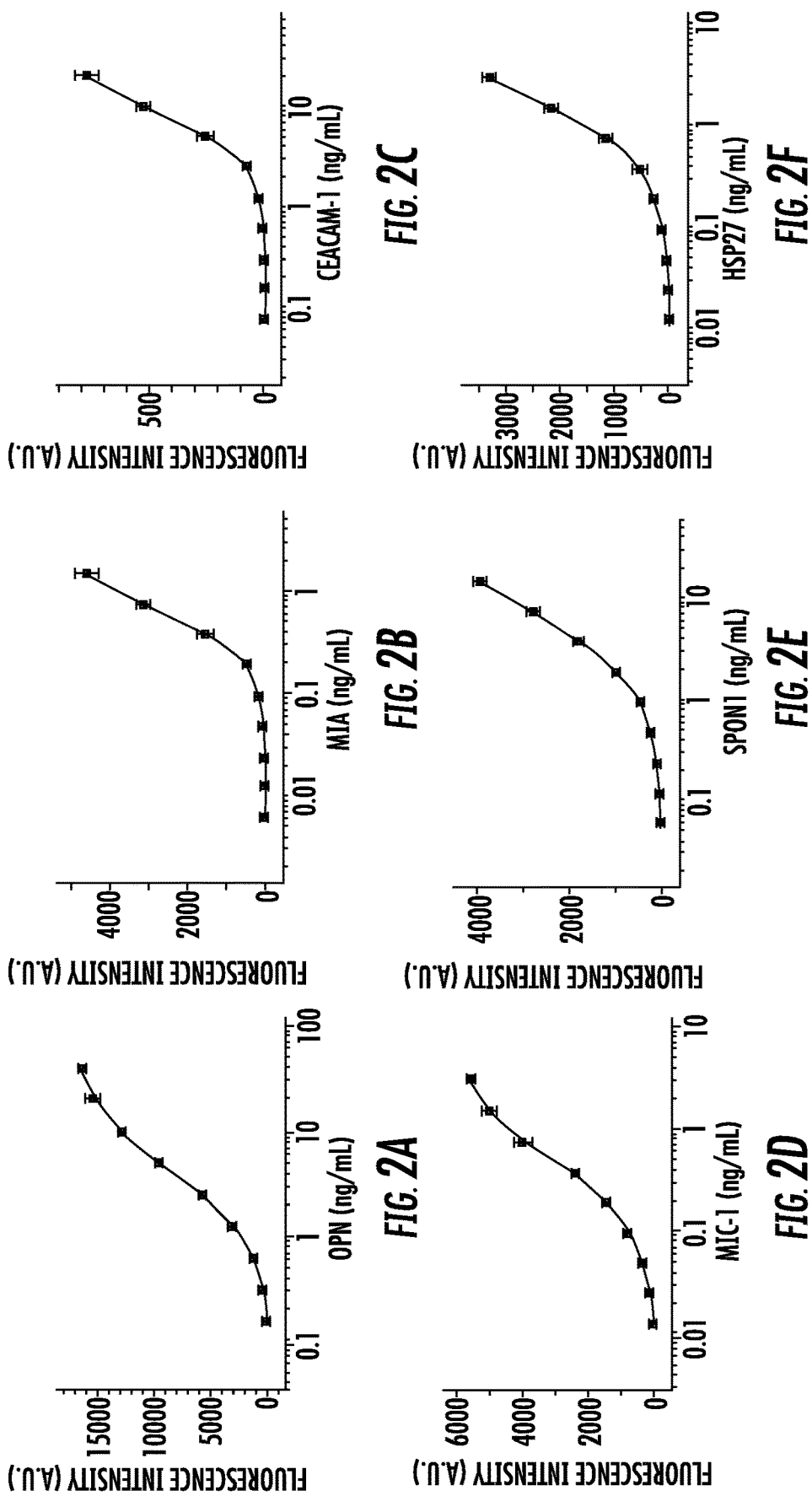

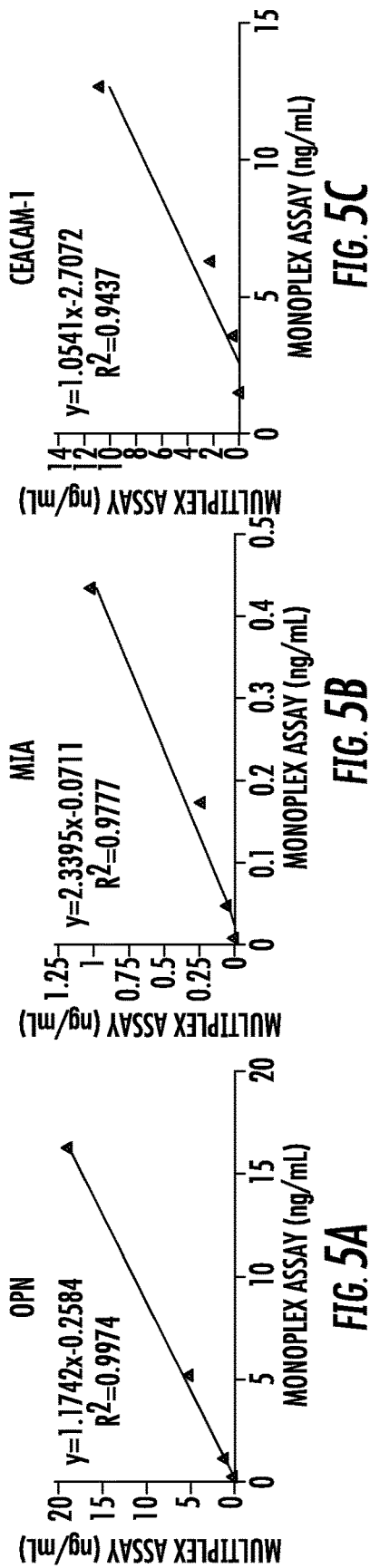
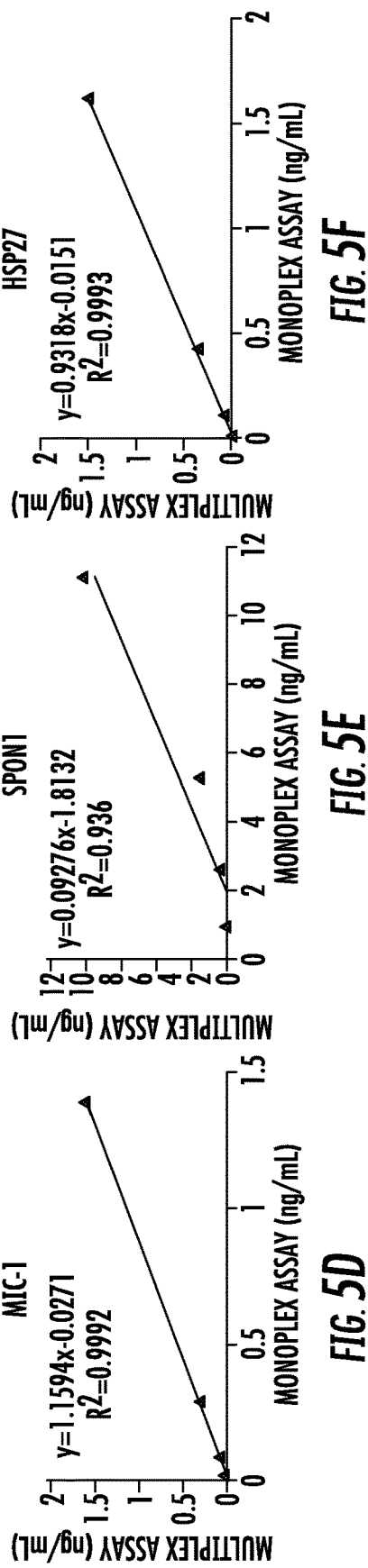
FIG. 5A  FIG. 5B  FIG. 5C  FIG. 5D  FIG. 5E  FIG. 5F

COMPOSITIONS AND METHODS FOR DETECTING PANCREATIC CANCER

REFERENCE TO RELATED APPLICATIONS

This application is a Continuation of U.S. patent application Ser. No. 16/737,084, filed Jan. 8, 2020, which is a Continuation of U.S. patent application Ser. No. 15/747,780, filed Jan. 26, 2018, which is a 35 U.S.C. § 371 U.S. national entry of International Application PCT/US2016/043833, having an international filing date of Jul. 25, 2016, which claims the benefit of U.S. Provisional Application No. 62/197,946, filed Jul. 28, 2015, the content of each of the aforementioned applications is herein incorporated by reference in their entirety.

STATEMENT OF GOVERNMENT INTEREST

This invention was made with government support under grant number CA115102, awarded by the National Institute of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jun. 8, 2016, is named P13737-02_SL.txt and is 54,475 bytes in size.

BACKGROUND OF THE INVENTION

Pancreatic cancer is the 4th leading cause of cancer death in the United States. The majority of patients present with unresectable disease leading to a median survival of 6 months and an overall 5-year survival of less than 5%. Because intervention at an early stage could greatly improve the prognosis of patients, methods for early detection of this disease are urgently required.

SUMMARY OF THE INVENTION

As described below, the present invention provides diagnostic compositions and methods for detecting pancreatic cancer in a subject. Compositions and articles defined by the invention were isolated or otherwise manufactured in connection with the examples provided below. Other features and advantages of the invention will be apparent from the detailed description, and from the claims.

In one aspect, the invention provides a method of detecting pancreatic cancer in a subject, the method comprising measuring in a sample from the subject a level of CA19-9 polysaccharide relative to a reference, and a level of a polynucleotide or polypeptide of at least one marker selected from the group consisting of: OPN, MIA, CEACAM-1, MIC-1, SPON1, HSP27, POSTN, and LGALS3BP relative to a reference, wherein an increased level of the CA19-9 polysaccharide relative to a reference and an increased level of the polynucleotide or polypeptide relative to a reference indicates presence of pancreatic cancer in the subject.

In another aspect, the invention provides a method of distinguishing a pancreatic ductal adenocarcinoma (PDAC) from a benign pancreatic condition, the method comprising measuring in a sample from the subject a level of CA19-9 polysaccharide relative to a reference, and a level of a polynucleotide or polypeptide of at least one marker selected from the group consisting of: OPN, MIA, CEACAM-1, MIC-1, SPON1, HSP27, POSTN, and LGALS3BP relative to a reference.

In another aspect, the invention provides a method of selecting a subject for pancreatic cancer treatment, the method comprising detecting in a sample from the subject an increased level of CA19-9 polysaccharide relative to a reference, and an increased level of a polynucleotide or polypeptide of at least one marker selected from the group consisting of: OPN, MIA, CEACAM-1, MIC-1, SPON1, HSP27, POSTN, and LGALS3BP relative to a reference.

In another aspect, the invention provides a method of characterizing pancreatic cancer status in a subject, the method comprising measuring in a sample from the subject a level of CA19-9 polysaccharide relative to a reference, and a level of a polynucleotide or polypeptide of at least one marker selected from the group consisting of: OPN, MIA, CEACAM-1, MIC-1, SPON1, HSP27, POSTN, and LGALS3BP relative to a reference, wherein an increased level of the CA19-9 polysaccharide relative to a reference and an increased level of the polynucleotide or polypeptide relative to a reference indicates presence of pancreatic cancer in the subject.

In various embodiments of any aspect delineated herein, the marker is selected from the group consisting of: MIA, SPON1, MIC-1, and CEACAM-1. In various embodiments of any aspect delineated herein, the measuring step comprises measuring in a sample from the subject levels of markers comprising or consisting of a CA19-9 polysaccharide, a HSP27 polynucleotide or polypeptide, and a MIA polynucleotide or polypeptide. In various embodiments of any aspect delineated herein, the measuring step comprises measuring in a sample from the subject levels of markers comprising or consisting of a CA19-9 polysaccharide, a CEACAM-1 polynucleotide or polypeptide, a MIC-1 polynucleotide or polypeptide, a SPON1 polynucleotide or polypeptide, and a MIA polynucleotide or polypeptide.

In another aspect, the invention provides a method of detecting pancreatic cancer and/or characterizing a pancreatic cancer status in a subject, the method comprising measuring in a serum sample from the subject levels of markers comprising or consisting of a CA19-9 polysaccharide, a HSP27 polypeptide, and a MIA polypeptide, using a multiplexed bead based immunoassay, wherein levels of each marker are measured relative to a reference, and wherein increased levels of the markers indicate presence of pancreatic cancer.

In another aspect, the invention provides a method of detecting pancreatic cancer and/or characterizing a pancreatic cancer status in a subject, the method comprising measuring in a serum sample from the subject levels of markers comprising or consisting of a CA19-9 polysaccharide, a CEACAM-1 polypeptide, a MIC-1 polypeptide, a SPON1 polypeptide, and a MIA polypeptide, using a multiplexed bead based immunoassay, wherein levels of each marker are measured relative to a reference, and wherein increased levels of the markers indicate presence of pancreatic cancer.

In another aspect, the invention provides a method of detecting pancreatic cancer and/or characterizing a pancreatic cancer status in a subject, the method comprising measuring in a serum sample from the subject levels of markers comprising or consisting of a CA19-9 polysaccharide and a MIA polypeptide using a multiplexed bead based immunoassay, wherein levels of each marker are measured relative to a reference, and wherein increased levels of the markers indicate presence of pancreatic cancer.

In another aspect, the invention provides a method of detecting pancreatic cancer and/or characterizing a pancreatic cancer status in a subject, the method comprising measuring in a serum sample from the subject levels of markers comprising or consisting of a CA19-9 polysaccharide and a MIC-1 polypeptide using a multiplexed bead based immunoassay, wherein levels of each marker are measured relative to a reference, and wherein increased levels of the markers indicate presence of pancreatic cancer.

In another aspect, the invention provides a method of detecting pancreatic cancer and/or characterizing a pancreatic cancer status in a subject, the method comprising measuring in a serum sample from the subject levels of markers comprising or consisting of a CA19-9 polysaccharide and a CEACAM-1 polypeptide using a multiplexed bead based immunoassay, wherein levels of each marker are measured relative to a reference, and wherein increased levels of the markers indicate presence of pancreatic cancer.

In another aspect, the invention provides a method of detecting pancreatic cancer and/or characterizing a pancreatic cancer status in a subject, the method comprising measuring in a serum sample from the subject levels of markers comprising or consisting of a CA19-9 polysaccharide and a SPON1 polypeptide using a multiplexed bead based immunoassay, wherein levels of each marker are measured relative to a reference, and wherein increased levels of the markers indicate presence of pancreatic cancer.

In various embodiments of any aspect delineated herein, the sample is a serum sample. In various embodiments of any aspect delineated herein, the level of polysaccharide or polypeptide is measured using a bead based immunoassay or an ELISA. In various embodiments of any aspect delineated herein, the pancreatic cancer status is non-pancreatic cancer, pancreatitis, intraductal papillary mucinous neoplasm (IPMN), early stage pancreatic ductal adenocarcinoma (PDAC), or late stage pancreatic ductal adenocarcinoma (PDAC). In various embodiments of any aspect delineated herein, the benign pancreatic condition is pancreatitis or intraductal papillary mucinous neoplasm (IPMN).

In various embodiments of any aspect delineated herein, the pancreatic cancer treatment is chemotherapy or surgery. In various embodiments of any aspect delineated herein, the subject is a human.

In another aspect, the invention provides a diagnostic composition comprising a capture reagent detecting a CA19-9 polysaccharide and a capture reagent detecting at least one marker selected from the group consisting of: a MIA polynucleotide or polypeptide, a MIC-1 polynucleotide or polypeptide, a CEACAM-1 polynucleotide or polypeptide, a OPN polynucleotide or polypeptide, a SPON1 polynucleotide or polypeptide, a HSP27 polynucleotide or polypeptide, a POSTN polynucleotide or polypeptide, and a LGALS3BP polynucleotide or polypeptide.

In various embodiments of any aspect delineated herein, the capture reagent detecting a CA19-9 polysaccharide is an anti-CA19-9 antibody or an antigen-binding fragment thereof. In various embodiments, the capture reagents are fixed to a substrate. In further embodiments, the substrate is a magnetic bead.

In various embodiments of any aspect delineated herein, the diagnostic composition comprises an anti-CA19-9 antibody or an antigen-binding fragment thereof, and at least one antibody or antigen-binding fragment thereof selected from the group consisting of: an anti-MIC-1 antibody, an anti-CEACAM-1 antibody, an anti-MIA antibody, and an anti-SPON1 antibody.

In various embodiments of any aspect delineated herein, the diagnostic composition comprises an anti-CA19-9 antibody or an antigen-binding fragment thereof, an anti-HSP27 antibody or an antigen-binding fragment thereof, and an anti-MIA antibody or an antigen-binding fragment thereof.

In another aspect, the invention provides a kit comprising a diagnostic composition according to any other aspect delineated herein. In various embodiments of any aspect delineated herein, the level of polysaccharide or polypeptide is measured using a kit according to any other aspect delineated herein.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "CA19-9 polysaccharide" is meant a polysaccharide having the sequence Neu5Acα2,3Galβ1,3(Fucα1,4)GlcNAc (a sialyl Lewis (a) antigen) and having antigenic activity. The CA19-9 polysaccharide may be attached to a polypeptide a to form a glycoprotein (i.e. a polypeptide modified by the addition of carbohydrate residues).

By "CEACAM-1 polypeptide" is meant a polypeptide or fragment thereof having at least about 85% amino acid identity to NCBI Accession No. NP_001192273, NP_001171745, NP_001171744, NP_001171742, NP_001020083, or NP_001703 (various isoforms) and having cell adhesion mediation activity. The sequence at NCBI Accession No. NP_001192273 (SEQ ID NO: 1) is shown below:

```
  1 mghlsaplhr vrvpwqglll taslltfwnp pttaqlttes
    mpfnvaegke vlllvhnlpq 61 qlfgyswykg ervdgnrqiv gyaigtqqat pgpansgret
    iypnaslliq nvtqndtgfy 121 tlqviksdlv neeatgqfhv ypelpkpsis snnsnpvedk
    davaftcepe tqdttylwwi 181 nnqslpvspr lqlsngnrtl tllsvtrndt gpyeceiqnp
    vsanrsdpvt lnvtygpdtp 241 tispsdtyyr pganlslscy aasnppaqys wlingtfqqs
    tqelfipnit vnnsgsytch 301 annsvtgcnr ttvktiivte lspvvakpqi kaskttvtgd
    kdsvnltcst ndtgisirwf 361 fknqslpsse rmklsqgntt lsinpvkred agtywcevfn
    pisknqsdpi mlnvnynalp 421 qenglspgai agivigvval valiavalac flhfgktgrt
    tpmthltr
```

By "HSP27 polypeptide" is meant a polypeptide or fragment thereof having at least about 85% amino acid identity to GenBank Accession No. BAB17232 and having chaperone and cellular stress protection activities. The sequence at GenBank Accession No. BAB17232 (SEQ ID NO: 2) is shown below.

```
  1 mterrvpfsl lrgpswdpfr dwyphsrlfd qafglprlpe ewsqwlggss wpgyvrplpp 61 aaiespavaa paysralsrq lssgvseirh tadrwrvsld vnhfapdelt vktkdgvvei 121 tgkheerqde hgyisrcftr kytlppgvdp tqvssslspe gtltveapmp klatqsneit 181 ipvtfesraq lggpeaaksd etaak
```

By "LGALS3BP polypeptide" is meant a polypeptide or fragment thereof having at least about 85% amino acid identity to NCBI Accession No. NP_005558 and having beta-galactoside binding activity. The sequence at NCBI Accession No. NP_005558 (SEQ ID NO: 3) is shown below.

```
  1 mtpprlfwvw llvagtqgvn dgdmrladgg atnqgrveif yrgqwgtvcd nlwdltdasv 61 vcralgfena tqalgraafg qgsgpimlde vqctgteasl adckslgwlk sncrherdag 121 vvctnetrst htldlsrels ealgqifdsq rgcdlsisvn vqgedalgfc ghtviltanl 181 eaqalwkepg snvtmsvdae cvpmvrdllr yfysrridit lssvkcfhkl asaygarqlq 241 gycaslfail lpqdpsfqmp ldlyayavat gdalleklcl qflawnfeal tqaeawpsvp 301 tdllqlllpr sdlavpsela llkavdtwsw gerasheeve glvekirfpm mlpeelfelq 361 fnlslywshe alfqkktlqa lefhtvpfql larykglnlt edtykpriyt sptwsafvtd 421 sswsarksql vyqsrrgplv kyssdyfqap sdyryypyqs fqtpqhpsfl fqdkrvswsl 481 vylptiqscw nygfscssde lpvlgltksg gsdrtiayen kalmlceglf vadvtdfegw 541 kaaipsaldt nsskstssfp cpaghfngfr tvirpfyltn ssgvd
```

By "MIA polypeptide" is meant a polypeptide or fragment thereof having at least about 85% amino acid identity to NCBI Accession No. NP_001189482 or NP_006524 (various isoforms) and having melanoma inhibitory activity. The sequence at NCBI Accession No. NP_001189482 (SEQ ID NO: 4) is shown below:

```
  1 marslvclgv iillsafsgp gvrggpmpkl adrklcadqe cshpismava lqdymapdcr 61 fltihrgqvv yvfsklkgrg rlfwggsvqg dyygdlaarl gyfpssivre dqtlkpgkvd 121 vktdkwdfyc q
```

By "MIC-1 polypeptide" is meant a polypeptide or fragment thereof having at least about 85% amino acid identity to GenBank Accession No. AAB88673 and having macrophage inhibitory activity. The sequence at GenBank Accession No. AAB88673 (SEQ ID: NO: 5) is shown below.

```
  1 mpgqelrtln gsqmllvllv lswlphggal slaeasrasf pgpselhted srfrelrkry 61 edlltrlran qswedsntdl vpapavrilt pevrlgsggh lhlrisraal peglpeasrl 121 hralfrlspt asrswdvtrp lrrqlslarp qapalhlrls pppsqsdqll aesssarpql 181 elhlrpqaar grrrararng dhcplgpgrc crlhtvrasl edlgwadwvl sprevqvtmc 241 igacpsqfra anmhaqikts lhrlkpdtvp apccvpasyn pmvliqktdt gvslqtyddl 301 lakdchci
```

By "OPN polypeptide" is meant a polypeptide or fragment thereof having at least about 85% amino acid identity to NCBI Accession No. NP_001035149, NP_001035147, NP_000573.1, or NP_001238759.1 (various isoforms) and having hydroxyapatite binding activity. The sequence at NCBI Accession No. NP_001035149 (SEQ ID NO: 6) is shown below:

```
  1 mriavicfcl lgitcaipvk qadsgssek qnavsseetn dfkqetlpsk sneshdhmdd 61 mddeddddhv dsqdsidsnd sddvddtdds hqsdeshhsd esdelvtdfp tdlpatevft 121 pvvptvdtyd grgdsvvygl rskskkfrrp diqypdatde ditshmesee lngaykaipv 181 aqdlnapsdw dsrgkdsyet sqlddqsaet hshkqsrlyk rkandesneh sdvidsqels 241 kvsrefhshe fhshedmlvv dpkskeedkh lkfrisheld sassevn
```

By "POSTN polypeptide" is meant a polypeptide or fragment thereof having at least about 85% amino acid identity to GenBank Accession No. AAI06710 or AAI06711 (various isoforms) and having cell adhesion mediation activity. The sequence at GenBank Accession No. AAI06710 (SEQ ID NO: 7) is shown below.

```
  1 mipflpmfsl lllivnpin annhydkila hsrirgrdqg pnvcalqqil gtkkkyfstc 61 knwykksicg qkttvlyecc pgymrmegmk gcpavlpidh vygtlgivga tttqrysdas 121 klreeiegkg sftyfapsne awdnldsdir rglesnvnve llnalhshmi nkrmltkdlk 181 ngmiipsmyn nlglfinhyp ngvvtvncar iihgnqiatn gvvhvidrvl tqigtsiqdf 241 ieaeddlssf raaaitsdil ealgrdghft lfaptneafe klprgvleri mgdkvaseal 301 mkyhilntlq csesimggav fetlegntie igcdgdsitv ngikmvnkkd ivtnngvihl 361 idqvlipdsa kqvielagkq qttftdlvaq lglasalrpd geytllapvn nafsddtlsm 421 dqrllklilq nhilkvkvgl nelyngqile tiggkqlrvf vyrtavcien scmekgskqg 481 rngaihifre iikpaekslh eklkqdkrfs tflslleaad lkelltqpgd wtlfvptnda 541 fkgmtseeke ilirdknalq niilyhltpg vfigkgfepg vtnilkttqg skiflkevnd 601 tllvnelksk esdimttngv ihvvdkllyp adtpvgndql leilnkliky iqikfvrgst 661 fkeipvtvyk piikkytkii dgvpveitek etreeriitg peikytrist gggeteetlk 721 kllqeevtkv tkfieggdgh lfedeeikrl lqgdtpvrkl qankkvqgsr rrlregrsq
```

By "SPON1 polypeptide" is meant a polypeptide or fragment thereof having at least about 85% amino acid identity to NCBI Accession No. NP_006099 and having cell adhesion promotion activity. The sequence at NCBI Accession No. NP_006099 (SEQ ID NO: 8) is shown below.

```
  1 mrlspaplkl srtpallala lplaaalafs detldkvpks egycsrilra qgtrrregyte
 61 fslrvegdpd fykpgtsyrv tlsaappsyf rgftlialre nregdkeedh agtfqiidee
121 etqfmsncpv avtestprrr triqvfwiap pagtgcvilk asivqkriiy fqdegsltkk
181 lceqdstfdg vtdkpildcc acgtakyrlt fygnwsekth pkdyprranh wsaiiggshs
241 knyvlweygg yasegvkqva elgspvkmee eirqqsdevl tvikakaqwp awqplnvraa
301 psaefsvdrt rhlmsfltmm gpspdwnvgl saedlctkec gwvqkvvqdl ipwdagtdsg
361 vtyespnkpt ipqekirplt sldhpqspfy dpeggsitqv arvvieriar kgeqcnivpd
421 nvddivadla peekdeddtp etciysnwsp wsacsssstcd kgkrmrqrml kaqldlsvpc
481 pdtqdfqpcm gpgcsdedgs tctmsewitw spcsiscgmg mrsreryvkq fpedgsvctl
541 pteetekctv neecspsscl mtewgewdec satcgmgmkk rhrmikmnpa dgsmckaets
601 qaekcmmpec htipcllspw sewsdcsvtc gkgmrtrqrm lkslaelgdc nedleqvekc
661 mlpecpidce ltewsqwsec nkscgkghvi rtrmiqmepq fggapcpetv qrkkcrirkc
721 lrnpsiqklr wrearesrrs eqlkeesege qfpgcrmrpw tawsectklc gggiqerymt
781 vkkrfkssqf tsckdkkeir acnvhpc
```

By "CEACAM-1 polynucleotide" is meant a polynucleotide encoding a CEACAM-1 polypeptide. An exemplary CEACAM-1 polynucleotide sequence is provided at NCBI Accession No. NM_001205344 (SEQ ID NO: 9). SEQ ID NO: 9 is provided below.

```
   1 aaagctctgg gccccaggga ggaggctcag cacagagagt ggaaaacagc agaggtgaca
  61 gagcagccgt gctcgaagcg ttcctggagc ccaagctctc ctccacaggt gaagacaggg
 121 ccagcaggag acaccatggg gcacctctca gccccacttc acagagtgcg tgtaccctgg
 181 caggggcttc tgctcacagc ctcacttcta accttctgga acccgcccac cactgcccag
 241 ctcactactg aatccatgcc attcaatgtt gcagagggga aggaggttct tctccttgtc
 301 cacaatctgc cccagcaact ttttggctac agctggtaca aggggaaag agtggatggc
 361 aaccgtcaaa ttgtaggata tgcaatagga actcaacaag ctacccagg gcccgcaaac
 421 agcggtcgag agacaatata ccccaatgca tccctgctga tccagaacgt cacccagaat
 481 gacacaggat tctacaccct acaagtcata aagtcagatc ttgtgaatga agaagcaact
 541 ggacagttcc atgtataccc ggagctgccc aagccctcca tctccagcaa caactccaac
 601 cctgtggagg acaaggatgc tgtggccttc acctgtgaac ctgagactca ggacacaacc
 661 tacctgtggt ggataaacaa tcagagcctc ccggtcagtc ccaggctgca gctgtccaat
 721 ggcaacagga ccctcactct actcagtgtc acaaggaatg acacaggacc ctatgagtgt
 781 gaaatacaga cccagtgag tgcgaaccgc agtgacccag tcaccttgaa tgtcacctat
 841 ggcccggaca cccccaccat ttccccttca gacacctatt accgtccagg ggcaaacctc
 901 agcctctcct gctatgcagc ctctaaccca cctgcacagt actcctggct tatcaatgga
 961 acattccagc aaagcacaca agagctcttt atccctaaca tcactgtgaa taatagtgga
1021 tcctataccc tgccacgcca ataactcagtc actggctgca acaggaccac agtcaagacg
1081 atcatagtca ctgagctaag tccagtagta gcaaagcccc aaatcaaagc cagcaagacc
1141 acagtcacag gagataagga ctctgtgaac ctgacctgct ccacaaatga cactggaatc
1201 tccatccgtt ggttcttcaa aaaccagagt ctccgtcct cggagaggat gaagctgtcc
1261 cagggcaaca ccacccctcag cataaaccct gtcaagaggg aggatgctgg gacgtattgg
```

-continued

```
1321 tgtgaggtct tcaacccaat cagtaagaac caaagcgacc ccatcatgct gaacgtaaac
1381 tataatgctc taccacaaga aaatggcctc tcacctgggg ccattgctgg cattgtgatt
1441 ggagtagtgg ccctggttgc tctgatagca gtagccctgg catgttttct gcatttcggg
1501 aagaccggca ggaccactcc aatgacccac ctaacaagat gaatgaagtt acttattcta
1561 ccctgaactt tgaagcccag caacccacac aaccaacttc agcctcccca tccctaacag
1621 ccacagaaat aatttattca gaagtaaaaa agcagtaatg aaacctgtcc tgctcactgc
1681 agtgctgatg tatttcaagt ctctcaccct catcactagg agattccttt ccctgtagg
1741 ggtagagggg tggggacaga aacaactttc tcctactctt ccttcctaat aggcatctcc
1801 aggctgcctg gtcactgccc ctctctcagt gtcaatagat gaaagtacat tgggagtctg
1861 taggaaaccc aaccttcttg tcattgaaat ttggcaaagc tgactttggg aaagagggac
1921 cagaacttcc cctcccttcc ccttttccca acctggactt gttttaaact tgcctgttca
1981 gagcactcat tccttcccac ccccagtcct gtcctatcac tctaattcgg atttgccata
2041 gccttgaggt tatgtccttt tccattaagt acatgtgcca ggaaacaaga gagagagaaa
2101 gtaaaggcag taatgccttc tcctatttct ccaaagcctt gtgtgaactc accaaacaca
2161 agaaaatcaa atatataacc aatagtgaaa tgccacacct ttgtccactg tcagggttgt
2221 ctacctgtag gatcagggtc taagcacctt ggtgcttagc tagaatacca cctaatcctt
2281 ctggcaagcc tgtcttcaga gaacccacta gaagcaacta ggaaaatcac ttgccaaaat
2341 ccaaggcaat tcctgatgga aaatgcaaaa gcacatatat gttttaatat ctttatgggc
2401 tctgttcaag gcagtgctga gagggagggg ttatagcttc aggagggaac cagcttctga
2461 taaacacaat ctgctaggaa cttgggaaag gaatcagaga gctgcccttc agcgattatt
2521 taaattattg ttaaagaata cacaatttgg ggtattggga ttttctcct tttctctgag
2581 acattccacc attttaattt ttgtaactgc ttatttatgt gaaaagggtt attttttactt
2641 agcttagcta tgtcagccaa tccgattgcc ttaggtgaaa gaaaccaccg aaatccctca
2701 ggtcccttgg tcaggagcct ctcaagattt tttttgtcag aggctccaaa tagaaaataa
2761 gaaaaggttt tcttcattca tggctagagc tagatttaac tcagtttcta ggcacctcag
2821 accaatcatc aactaccatt ctattccatg tttgcacctg tgcattttct gtttgccccc
2881 attcactttg tcaggaaacc ttggcctctg ctaaggtgta tttggtcctt gagaagtggg
2941 agcaccctac agggacacta tcactcatgc tggtggcatt gtttacagct agaaagctgc
3001 actggtgcta atgccccttg gggaaatggg gctgtgagga ggaggattat aacttaggcc
3061 tagcctcttt taacagcctc tgaaatttat cttttcttct atgggtctta taaatgtatc
3121 ttataataaa aaggaaggac aggaggaaga caggcaaatg tacttctcac ccagtcttct
3181 acacagatgg aatctctttg gggctaagag aaaggtttta ttctatattg cttacctgat
3241 ctcatgttag gcctaagagg ctttctccag gaggattagc ttggagttct ctatactcag
3301 gtacctcttt caggggtttc taaccctgac acggactgtg catactttcc ctcatccatg
3361 ctgtgctgtg ttatttaatt tttcctggct aagatcatgt ctgaattatg tatgaaaatt
3421 attctatgtt tttataataa aaataatata tcagacatcg aaaaaaaaaa
```

By "HSP27 polynucleotide" is meant a polynucleotide encoding a HSP27 polypeptide. An exemplary HSP27 polynucleotide sequence is provided at GenBank Accession No. AB020027 (SEQ ID NO: 10). SEQ ID NO: 10 is provided below.

```
  1 ggcacgagga gcagagtcag ccagcatgac cgagcgccgc gtccccttct cgctcctgcg
 61 gggccccagc tgggaccoct tccgcgactg gtaccogcat agccgcctct tcgaccaggc
121 cttcgggctg ccccggctgc cggaggagtg gtcgcagtgg ttaggcggca gcagctggcc
181 aggctacgtg cgccccctgc ccccogccgc catcgagagc cccgcagtgg ccgcgcccgc
241 ctacagccgc gcgctcagcc ggcaactcag cagcggggtc tcggagatcc ggcacactgc
301 ggaccgctgg cgcgtgtccc tggatgtcaa ccacttcgcc ccggacgagc tgacggtcaa
361 gaccaaggat ggcgtggtgg agatcaccgg caagcacgag gagcggcagg acgagcatgg
421 ctacatctcc cggtgcttca cgcggaaata cacgctgccc cccggtgtgg acccaccca
481 agtttcctcc tccctgtccc ctgagggcac actgaccgtg gaggccccca tgcccaagct
541 agccacgcag tccaacgaga tcaccatccc agtcaccttc gagtcgcggg cccagcttgg
601 gggcccagaa gctgcaaaat ccgatgagac tgccgccaag taaagccta gcccggatgc
661 ccaccctgc tgccgccact ggctgtgcct ccccgccac ctgtgtgttc ttttgataca
721 tttatcttct gtttttctca aataaagttc aaagcaacca cctg
```

By "LGALS3BP polynucleotide" is meant a polynucleotide encoding a LGALS3BP polypeptide. An exemplary LGALS3BP polynucleotide sequence is provided at GenBank Accession No. NM_005567 (SEQ ID NO: 11). SEQ ID NO: 11 is provided below.

```
   1 aatcgaaagt agactctttt ctgaagcatt tcctgggatc agcctgacca cgctccatac
  61 tgggagaggc ttctgggtca aggaccagt ctgcagaggg atcctgtggc tggaagcgag
 121 gaggctccac acggccgttg cagctaccgc agccaggatc tgggcatcca ggcacggcca
 181 tgacccctcc gaggctcttc tgggtgtggc tgctggttgc aggaacccaa ggcgtgaacg
 241 atggtgacat gcggctggcc gatggggggcg ccaccaacca gggccgcgtg gagatcttct
 301 acagaggcca gtggggcact gtgtgtgaca acctgtggga cctgactgat gccagcgtcg
 361 tctgccggc cctgggcttc gagaacgcca cccaggctct gggcagagct gccttcgggc
 421 aaggatcagg ccccatcatg ctggatgagg tccagtgcac gggaaccgag gcctcactgg
 481 ccgactgcaa gtccctgggc tggctgaaga gcaactgcag gcacgagaga gacgctggtg
 541 tggtctgcac caatgaaacc aggagcaccc acaccctgga cctctccagg gagctctcgg
 601 aggcccttgg ccagatcttt gacagccagc ggggctgcga cctgtccatc agcgtgaatg
 661 tgcagggcga ggacgccctg ggcttctgtg ccacacggt catcctgact gccaacctgg
 721 aggcccaggc cctgtggaag gagccgggca gcaatgtcac catgagtgtg gatgctgagt
 781 gtgtgcccat ggtcagggac cttctcaggt acttctactc ccgaaggatt gacatcaccc
 841 tgtcgtcagt caagtgcttc cacaagctgg cctctgccta tggggccagg cagctgcagg
 901 gctactgcgc aagcctcttt gccatcctcc tcccccagga cccctcgttc cagatgcccc
 961 tggacctgta tgcctatgca gtggccacag gggacgccct gctggagaag ctctgcctac
1021 agttcctggc ctggaacttc gaggccttga cgcaggccga ggcctggccc agtgtcccca
1081 cagacctgct ccaactgctg ctgcccagga gcgacctggc ggtgcccagc gagctggccc
1141 tactgaaggc cgtggacacc tggagctggg gggagcgtgc ctcccatgag gaggtggagg
1201 gcttggtgga agatccgc ttccccatga tgctccctga ggagctcttt gagctgcagt
1261 tcaacctgtc cctgtactgg agccacgagg ccctgttcca gaagaagact ctgcaggccc
1321 tggaattcca cactgtgccc ttccagttgc tggccggta caaaggcctg aacctcaccg
```

```
1381 aggataccta caagccccgg atttacacct cgcccacctg gagtgccttt gtgacagaca 1441 gttcctggag tgcacggaag tcacaactgg tctatcagtc cagacggggg cctttggtca 1501 aatattcttc tgattacttc caagccccct ctgactacag atactacccc taccagtcct 1561 tccagactcc acaacacccc agcttcctct tccaggacaa gagggtgtcc tggtccctgg 1621 tctacctccc caccatccag agctgctgga actacggctt ctcctgctcc tcggacgagc 1681 tccctgtcct gggcctcacc aagtctggcg gctcagatcg caccattgcc tacgaaaaca 1741 aagccctgat gctctgcgaa gggctcttcg tggcagacgt caccgatttc gagggctgga 1801 aggctgcgat toccagtgcc ctggacacca acagctcgaa gagcacctcc tccttcccct 1861 gcccggcagg gcacttcaac ggcttccgca cggtcatccg cccttctac ctgaccaact 1921 cctcaggtgt ggactagacg gcgtggccca agggtggtga aaccggaga accccaggac 1981 gccctcactg caggctcccc tcctcggctt ccttcctctc tgcaatgacc ttcaacaacc 2041 ggccaccaga tgtcgcccta ctcacctgag cgctcagctt caagaaatta ctggaaggct 2101 tccactaggg tccaccagga gttctcccac cacctcacca gtttccaggt ggtaagcacc 2161 aggacgccct cgaggttgct ctgggatccc cccacagccc ctggtcagtc tgcccttgtc 2221 actggtctga ggtcattaaa attacattga ggttcctaca aaaaaaaaaa aaaaaaa
```

By "MIA polynucleotide" is meant a polynucleotide encoding a MIA polypeptide. An exemplary MIA polynucleotide sequence is provided at NCBI Accession No. NM_001202553 (SEQ ID NO: 12). SEQ ID NO:12 is provided below.

```
  1 cttctgtggc cagaggggac agcggaggag cccagtccac gatggcccgg tccctggtgt 61 gccttggtgt catcatcttg ctgtctgcct tctccggacc tggtgtcagg ggtggtccta 121 tgcccaagct ggctgaccgg aagctgtgtg cggaccagga gtgcagccac cctatctcca 181 tggctgtggc ccttcaggac tacatggccc ccgactgccg attcctgacc attcaccggg 241 gccaagtggt gtatgtcttc tccaagctga agggccgtgg gcggctcttc tggggaggca 301 gcgttcaggg agattactat ggagatctgg ctgctcgcct gggctatttc cccagtagca 361 ttgtccgaga ggaccagacc ctgaaacctg gcaaagtcga tgtgaagaca gacaaatggg 421 atttctactg ccagtgagct cagcctaccg ctggccctgc cgtttcccct ccttggcttt 481 atgcaaatac aatcagccca gtgcaaacgg aaaaaaaaaa aaaaaaaa
```

By "MIC-1 polynucleotide" is meant a polynucleotide encoding a MIC-1 polypeptide. An exemplary MIC-1 polynucleotide sequence is provided at GenBank Accession No. AF019770 (SEQ ID NO: 13). SEQ ID NO: 13 is provided below.

```
  1 gcggccgctg cacagccatg cccgggcaag aactcaggac gctgaatggc tctcagatgc 61 tcctggtgtt gctggtgctc tcgtggctgc cgcatggggg cgccctgtct ctggccgagg 121 cgagccgcgc aagtttcccg ggaccctcag agttgcacac cgaagactcc agattccgag 181 agttgcggaa acgctacgag gacctgctaa ccaggctgcg ggccaaccag agctgggaag 241 attcgaacac cgacctcgtc ccggcccctg cagtccggat actcacgcca gaagtgcggc 301 tgggatccgg cggccacctg cacctgcgta tctctcgggc cgcccttccc gagggcctcc 361 ccgaggcctc ccgccttcac cgggctctgt tccggcgtgt cccgacggcg tcaaggtcgt 421 gggacgtgac acgacctctg cggcgtcagc tcagccttgc aagacccag gcgcccgcgc
```

```
 481 tgcacctgcg actgtcgccg ccgccgtcgc agtcggacca actgctggca gaatcttcgt 541 ccgcacggcc ccagctggag ttgcacttgc ggccgcaagc cgccaggggg cgccgcagag 601 cgcgtgcgcg caacggggac cactgtccgc tcgggcccgg gcgttgctgc cgtctgcaca 661 cggtccgcgc gtcgctggaa gacctgggct gggccgattg ggtgctgtcg ccacgggagg 721 tgcaagtgac catgtgcatc ggcgcgtgcc cgagccagtt ccgggcggca aacatgcacg 781 cgcagatcaa gacgagcctg caccgcctga gcccgacac ggtgccagcg ccctgctgcg 841 tgcccgccag ctacaatccc atggtgctca ttcaaaagac cgacaccggg gtgtcgctcc 901 agacctatga tgacttgtta gccaaagact gccactgcat atgagcagtc ctggtccttc 961 cactgtgcac ctgcgcgggg gaggcgacct cagttgtcct gccctgtgga atgggctcaa 1021 ggttcctgag acacccgatt cctgcccaaa cagctgtatt tatataagtc tgttatttat 1081 tattaattta ttggggtgac cttcttgggg actcggggggc tggtctgatg gaactgtgta 1141 tttatttaaa actctggtga taaaaataaa gctgtctgaa ctgttaaaaa aaaaaaaaa 1201 aa
```

By "OPN polynucleotide" is meant a polynucleotide encoding a OPN polypeptide. An exemplary OPN polynucleotide sequence is provided at NCBI Accession No. NM_001040060 (SEQ ID NO: 14). SEQ ID NO: 14 is provided below.

```
   1 ctccctgtgt tggtggagga tgtctgcagc agcatttaaa ttctgggagg gcttggttgt 61 cagcagcagc aggaggaggc agagcacagc atcgtcggga ccagactcgt ctcaggccag 121 ttgcagcctt ctcagccaaa cgccgaccaa ggaaaactca ctaccatgag aattgcagtg 181 atttgctttt gcctcctagg catcacctgt gccataccag ttaaacaggc tgattctgga 241 agttctgagg aaaagcagaa tgctgtgtcc tctgaagaaa ccaatgactt aaacaagag 301 acccttccaa gtaagtccaa cgaaagccat gaccacatgg atgatatgga tgatgaagat 361 gatgatgacc atgtggacag ccaggactcc attgactcga acgactctga tgatgtagat 421 gacactgatg attctcacca gtctgatgag tctcaccatt ctgatgaatc tgatgaactg 481 gtcactgatt ttcccacgga cctgccagca accgaagttt tcactccagt tgtccccaca 541 gtagacacat atgatggccg aggtgatagt gtggtttatg gactgaggtc aaaatctaag 601 aagtttcgca gacctgacat ccagtaccct gatgctacag acgaggacat cacctcacac 661 atggaaagcg aggagttgaa tggtgcatac aaggccatcc ccgttgccca ggacctgaac 721 gcgccttctg attgggacag ccgtgggaag gacagttatg aaacgagtca gctggatgac 781 cagagtgctg aaacccacag ccacaagcag tccagattat ataagcggaa agccaatgat 841 gagagcaatg agcattccga tgtgattgat agtcaggaac tttccaaagt cagccgtgaa 901 ttccacagcc atgaatttca cagccatgaa gatatgctgg ttgtagaccc caaaagtaag 961 gaagaagata acaccctgaa atttcgtatt tctcatgaat tagatagtgc atcttctgag 1021 gtcaattaaa aggagaaaaa atacaatttc tcactttgca tttagtcaaa agaaaaaatg 1081 ctttatagca aaatgaaaga gaacatgaaa tgcttctttc tcagtttatt ggttgaatgt 1141 gtatctattt gagtctggaa ataactaatg tgtttgataa ttagtttagt ttgtggcttc 1201 atggaaactc cctgtaaact aaaagcttca gggttatgtc tatgttcatt ctatagaaga 1261 aatgcaaact atcactgtat tttaatattt gttattctct catgaataga aatttatgta 1321 gaagcaaaca aaatactttt acccacttaa aaagagaata taacatttta tgtcactata
```

-continued

```
1381 atcttttgtt ttttaagtta gtgtatattt tgttgtgatt atcttttttgt ggtgtgaata 1441 aatcttttat cttgaatgta ataagaattt ggtggtgtca attgcttatt tgttttccca 1501 cggttgtcca gcaattaata aaacataacc tttttttactg cctaaaaaaa aaaaaaaaaa
```

By "POSTN polynucleotide" is meant a polynucleotide encoding a POSTN polypeptide. An exemplary POSTN polynucleotide sequence is provided at GenBank Accession No. BC106709 (SEQ ID NO: 15). SEQ ID NO: 15 is provided below.

```
   1 agagactcaa gatgattccc tttttaccca tgttttctct actattgctg cttattgtta 61 accctataaa cgccaacaat cattatgaca agatcttggc tcatagtcgt atcaggggtc 121 gggaccaagg cccaaatgtc tgtgcccttc aacagatttt gggcaccaaa aagaaatact 181 tcagcacttg taagaactgg tataaaaagt ccatctgtgg acagaaaacg actgtgttat 241 atgaatgttg ccctggttat atgagaatgg aaggaatgaa aggctgccca gcagttttgc 301 ccattgacca tgtttatggc actctgggca tcgtgggagc caccacaacg cagcgctatt 361 ctgacgcctc aaaactgagg gaggagatcg agggaaaggg atccttcact tactttgcac 421 cgagtaatga ggcttgggac aacttggatt ctgatatccg tagaggtttg gagagcaacg 481 tgaatgttga attactgaat gctttacata gtcacatgat taataagaga atgttgacca 541 aggacttaaa aaatggcatg attattcctt caatgtataa caatttgggg cttttcatta 601 accattatcc taatggggtt gtcactgtta attgtgctcg aatcatccat gggaaccaga 661 ttgcaacaaa tggtgttgtc catgtcattg accgtgtgct tacacaaatt ggtacctcaa 721 ttcaagactt cattgaagca gaagatgacc tttcatcttt tagagcagct gccatcacat 781 cggacatatt ggaggccctt ggaagagacg gtcacttcac actcttttgct cccaccaatg 841 aggcttttga gaaacttcca cgaggtgtcc tagaaaggat catgggagac aaagtggctt 901 ccgaagctct tatgaagtac cacatcttaa atactctcca gtgttctgag tctattatgg 961 gaggagcagt ctttgagacg ctggaaggaa atacaattga gataggatgt gacggtgaca 1021 gtataacagt aaatggaatc aaaatggtga acaaaaagga tattgtgaca aataatggtg 1081 tgatccattt gattgatcag gtcctaattc ctgattctgc caaacaagtt attgagctgg 1141 ctggaaaaca gcaaaccacc ttcacggatc ttgtggccca attaggcttg gcatctgctc 1201 tgaggccaga tggagaatac actttgctgg cacctgtgaa taatgcattt tctgatgata 1261 ctctcagcat ggatcagcgc ctccttaaat taattctgca gaatcacata ttgaaagtaa 1321 aagttggcct taatgagctt tacaacgggc aaatactgga aaccatcgga ggcaaacagc 1381 tcagagtctt cgtatatcgt acagctgtct gcattgaaaa ttcatgcatg gagaaaggga 1441 gtaagcaagg gagaaacggt gcgattcaca tattccgcga gatcatcaag ccagcagaga 1501 aatccctcca tgaaaagtta aaacaagata gcgcttttag caccttcctc agcctacttg 1561 aagctgcaga cttgaaagag ctcctgacac aacctggaga ctggacatta tttgtgccaa 1621 ccaatgatgc ttttaaggga atgactagtg aagaaaaaga aattctgata cgggacaaaa 1681 atgctcttca aaacatcatt ctttatcacc tgacaccagg agttttcatt ggaaaaggat 1741 ttgaacctgg tgttactaac attttaaaga ccacacaagg aagcaaaatc tttctgaaag 1801 aagtaaatga tacacttctg gtgaatgaat tgaaatcaaa agaatctgac atcatgacaa 1861 caaatggtgt aattcatgtt gtagataaac tcctctatcc agcagacaca cctgttggaa 1921 atgatcaact gctggaaata cttaataaat taatcaaata catccaaatt aagtttgttc
```

-continued

```
1981 gtggtagcac cttcaaagaa atccccgtga ctgtctataa gccaattatt aaaaaataca
2041 ccaaaatcat tgatggagtg cctgtggaaa taactgaaaa agagacacga gaagaacgaa
2101 tcattacagg tcctgaaata aaatacacta ggatttctac tggaggtgga gaaacagaag
2161 aaactctgaa gaaattgtta caagaagagg tcaccaaggt caccaaattc attgaaggtg
2221 gtgatggtca tttatttgaa gatgaagaaa ttaaaagact gcttcaggga gacacacccg
2281 tgaggaagtt gcaagccaac aaaaaagttc aaggatctag aagacgatta agggaaggtc
2341 gttctcagtg aaaatccaaa aaccagaaaa aaatgtttat acaaccctaa gtcaataacc
2401 tgaccttaga aaattgtgag agccaagttg acttcaggaa ctgaaacatc agcac
```

15

By "SPON1 polynucleotide" is meant a polynucleotide encoding a SPON1 polypeptide. An exemplary SPON1 polynucleotide sequence is provided at NCBI Accession No. NM_006108 (SEQ ID NO: 16). SEQ ID NO:16 is provided below.

```
   1 gcaaaatcag ccctccctcc tcccgctcct tcgccgcggc cctcccctcc tcgcgctgct
  61 ctcgttcgct tggctcagct cagctcagct cagcgcagct ccgcggccgc caagccgagg
 121 cgggcacggt ctccgagtcg cggacgccag ctccgagctc cctctctccg ccgcgcctcc
 181 gccaggtcgc gccttcgtcg ggaccacttc gggcaggagt cgcgtggcga aggcctgcgg
 241 ccgcggcaca aagttggggg ccgcgaagat gaggctgtcc ccggcgcccc tgaagctgag
 301 ccggactccg gcactgctgg ccctggcgct gccctggcc gcggcgctgg ccttctccga
 361 cgagaccctg gacaaagtgc ccaagtcaga gggctactgc agccgtatcc tgcgcgccca
 421 gggcacgcgg cgcgagggct acaccgagtt cagcctccgc gtggagggcg accccgactt
 481 ctacaagccg ggaaccagct accgcgtaac actttcagct gctcctccct cctacttcag
 541 aggattcaca ttaattgccc tcagagagaa cagagagggt gataaggaag aagaccatgc
 601 tgggaccttc cagatcatag acgaagaaga aactcagttt atgagcaatt gccctgttgc
 661 agtcactgaa agcactccac ggaggaggac ccggatccag gtgttttgga tagcaccacc
 721 agcgggaaca ggctgcgtga ttctgaaggc cagcatcgta caaaaacgca ttatttattt
 781 tcaagatgag ggctctctga ccaagaaact ttgtgaacaa gattccacat ttgatggggt
 841 gactgacaaa cccatcttag actgctgtgc ctgcggaact gccaagtaca gactcacatt
 901 ttatgggaat tggtccgaga agacacaccc aaaggattac cctcgtcggg ccaaccactg
 961 gtctgcgatc atcggaggat cccactccaa gaattatgta ctgtgggaat atggaggata
1021 tgccagcgaa ggcgtcaaac aagttgcaga attgggctca cccgtgaaaa tggaggaaga
1081 aattcgacaa cagagtgatg aggtcctcac cgtcatcaaa gccaaagccc aatggccagc
1141 ctggcagcct ctcaacgtga gagcagcacc ttcagctgaa ttttccgtgg acagaacgcg
1201 ccatttaatg tccttcctga ccatgatggg ccctagtccc gactgaaacg taggcttatc
1261 tgcagaagat ctgtgcacca aggaatgtgg ctgggtccag aaggtggtgc aagacctgat
1321 tccctgggac gctggcaccg acagcggggt gacctatgag tcacccaaca aacccaccat
1381 tccccaggag aaaatccggc ccctgaccag cctggaccat cctcagagtc ctttctatga
1441 cccagagggt gggtccatca ctcaagtagc cagagttgtc atcgagagaa tcgcacggaa
1501 gggtgaacaa tgcaatattg tacctgacaa tgtcgatgat attgtagctg acctggctcc
1561 agaagagaaa gatgaagatg acaccccctga aacctgcatc tactccaact ggtccccatg
1621 gtccgcctgc agctcctcca cctgtgacaa aggcaagagg atgcgacagc gcatgctgaa
```

-continued

```
1681 agcacagctg gacctcagcg tcccctgccc tgacacccag gacttccagc cctgcatggg
1741 ccctggctgc agtgacgaag acggctccac ctgcaccatg tccgagtgga tcacctggtc
1801 gccctgcagc atctcctgcg gcatgggcat gaggtcccgg gagaggtatg tgaagcagtt
1861 cccggaggac ggctccgtgt gcacgctgcc cactgaggaa acgagaagt gcacggtcaa
1921 cgaggagtgc tctcccagca gctgcctgat gaccgagtgg ggcgagtggg acgagtgcag
1981 cgccacctgc ggcatgggca tgaagaagcg gcaccgcatg atcaagatga ccccgcaga
2041 tggctccatg tgcaaagccg agacatcaca ggcagagaag tgcatgatgc cagagtgcca
2101 caccatccca tgcttgctgt ccccatggtc cgagtggagt gactgcagcg tgacctgcgg
2161 gaagggcatg cgaacccgac agcggatgct caagtctctg gcagaacttg agactgcaa
2221 tgaggatctg gagcaggtgg agaagtgcat gctccctgaa tgccccattg actgtgagct
2281 caccgagtgg tcccagtggt cggaatgtaa caagtcatgt gggaaaggcc acgtgattcg
2341 aacccggatg atccaaatgg agcctcagtt tggaggtgca ccctgcccag agactgtgca
2401 gcgaaaaag tgccgcatcc gaaaatgcct tcgaaatcca tccatccaaa agctacgctg
2461 gagggaggcc cgagagagcc ggcggagtga gcagctgaag gaagagtctg aaggggagca
2521 gttcccaggt tgtaggatgc gcccatggac ggcctggtca gaatgcacca aactgtgcgg
2581 aggtggaatt caggaacgtt acatgactgt aaagaagaga ttcaaaagct cccagtttac
2641 cagctgcaaa gacaagaagg agatcagagc atgcaatgtt catccttgtt agcaagggta
2701 cgagttcccc agggctgcac tctagattcc agagtcacca atggctggat tatttgcttg
2761 tttaagacaa tttaaattgt gtacgctagt tttcattttt gcagtgtggt tcgcccagta
2821 gtcttgtgga tgccagagac atcctttctg aatacttctt gatgggtaca ggctgagtgg
2881 ggcgccctca cctccagcca gcctcttcct gcagaggagt agtgtcagcc accttgtact
2941 aagctgaaac atgtccctct ggagcttcca cctggccagg gaggacggag actttgacct
3001 actccacatg gagaggcaac catgtctgga agtgactatg cctgagtccc agggtgcggc
3061 aggtaggaaa cattcacaga tgaagacagc agattcccca cattctcatc tttggcctgt
3121 tcaatgaaac cattgtttgc ccatctcttc ttagtggaac tttaggtctc ttttcaagtc
3181 tcctcagtca tcaatagttc ctggggaaaa acagagctgg tagacttgaa gaggagcatt
3241 gatgttgggt ggcttttgtt ctttcactga gaaattcgga atacatttgt ctcacccctg
3301 atattggttc ctgatgcccc cccaacaaaa ataaataaat aaattatggc tgctttattt
3361 aaatataagg tagctagttt ttacacctga gataaataat aagcttagag tgtattttc
3421 ccttgctttt gggggttcag aggagtatgt acaattcttc tgggaagcca gccttctgaa
3481 cttttggta ctaaatcctt attggaacca agacaaagga agcaaaattg gtctctttag
3541 agaccaattt gcctaaattt taaaatcttc ctacacacat ctagacgttc aagtttgcaa
3601 atcagttttt agcaagaaaa cattttgct atacaaacat tttgctaagt ctgcccaaag
3661 ccccccaat gcattccttc aacaaaatac aatctctgta ctttaaagtt attttagtca
3721 tgaaatttta tatgcagaga gaaaagtta ccgagacaga aaacaaatct aagggaaagg
3781 aatattatgg gattaagctg agcaagcaat tctggtggaa agtcaaacct gtcagtgctc
3841 cacaccaggg ctgtggtcct cccagacatg cataggaatg ccacaggtt tacactgcct
3901 tcccagcaat tataagcaca ccagattcag ggagactgac caccaaggga tagtgtaaaa
3961 ggacattttc tcagttgggt ccatcagcag ttttcttcc tgcatttatt gttgaaaact
4021 attgtttcat ttcttctttt ataggcctta ttactgctta atccaaatgt gtaccattgg
```

```
-continued
4081 tgagacacat acaatgctct gaatacacta cgaatttgta ttaaacacat cagaatattt 4141 ccaaatacaa catagtatag tcctgaatat gtacttttaa cacaagagag actattcaat 4201 aaaaactcac tgggtctttc atgtctttaa gctaagtaag tgttcagaag gttctttttt 4261 atattgtcct ccacctccat cattttcaat aaaagatagg gcttttgctc ccttgttctt 4321 ggagggacca ttattacatc tctgaactac ctttgtatcc aacatgtttt aaatccttaa 4381 atgaattgct ttctcccaaa aaaagcacaa tataaagaaa cacaagattt aattattttt 4441 ctacttgggg ggaaaaaagt cctcatgtag aagcacccac ttttgcaatg ttgttctaag 4501 ctatctatct aactctcagc ccatgataaa gttccttaag ctggtgattc ctaatcaagg 4561 acaagccacc ctagtgtctc atgtttgtat ttggtcccag ttgggtacat tttaaaatcc 4621 tgattttgga gacttaaaac caggttaatg gctaagaatg ggtaacatga ctcttgttgg 4681 attgttattt tttgtttgca atggggaatt tataagaagc atcaagtctc tttcttacca 4741 aagtcttgtt aggtggttta tagttctttt ggctaacaaa tcattttgga aataaagatt 4801 ttttactaca aaaatgaaat ttgtttggac ttccacttga gacagtaaag agagtattag 4861 acacccagta aaaactgcca tataaagaag ttgtaattgt ttgttgtgta tgtatttttt 4921 tcaatgccaa accagctgtg atccaattta catccacatt ttaggtccaa cagcaagaag 4981 ttcagagaga gatttcccaa ccagacattg ggtcactcac tggtcacctt gccagtgcat 5041 tttattagaa gggaatctgt tgtagcaaat gggaataaac ctgggtttct atagacccag 5101 aactgaaaaa ataaacatcg tgctgttttt aatttgaaaa aaaaaaaaaa aaaa
```

By "anti-CA19-9 antibody" is meant an antibody that selectively binds a CA19-9 polysaccharide.

By "anti-CEACAM-1 antibody" is meant an antibody that selectively binds a CEACAM-1 polypeptide.

By "anti-HSP27 antibody" is meant an antibody that selectively binds a HSP27 polypeptide.

By "anti-MIA antibody" is meant an antibody that selectively binds a MIA polypeptide.

By "anti-MIC-1 antibody" is meant an antibody that selectively binds a MIC-1 polypeptide.

By "anti-SPON1 antibody" is meant an antibody that selectively binds a SPON1 polypeptide.

By "disease" is meant any condition or disorder that damages or interferes with the normal function of a cell, tissue, or organ. Examples of diseases include pancreatic cancer.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen.

Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

"Diagnostic" means identifying the presence or nature of a pathologic condition, i.e., pancreatic cancer. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

By "marker" is meant any protein or polynucleotide having an alteration in expression level or activity that is associated with a disease or disorder. The term "biomarker" is used interchangeably with the term "marker."

The term "measuring" means methods which include detecting the presence or absence of marker(s) in the sample, quantifying the amount of marker(s) in the sample, and/or qualifying the type of biomarker. Measuring can be accomplished by methods known in the art and those further described herein, including but not limited to immunoassay. Any suitable methods can be used to detect and measure one or more of the markers described herein. These methods include, without limitation, ELISA and bead-based immunoassays (e.g., monoplexed or multiplexed bead-based immunoassays, magnetic bead-based immunoassays).

As used herein, "obtaining" as in "obtaining an agent" includes synthesizing, purchasing, or otherwise acquiring the agent.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

"Immunoassay" is an assay that uses an antibody to specifically bind an antigen (e.g., a marker). The immunoassay is characterized by the use of specific binding properties of a particular antibody to isolate, target, and/or quantify the antigen.

The term "antibody," as used in this disclosure, refers to an immunoglobulin or a fragment or a derivative thereof, and encompasses any polypeptide comprising an antigen-binding site, regardless of whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')2, Fv, scFv, Fd, dAb, and other antibody fragments that retain antigen-binding function, i.e., the ability to bind, for example, PD-L1, specifically. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant." An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

Binding fragments of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')2 fragment in which the two arms of the antibody molecule remain linked and comprise two-antigen binding sites. The F(ab')2 fragment has the ability to crosslink antigen. "Fv" when used herein refers to the minimum fragment of an antibody that retains both antigen-recognition and antigen-binding sites. "Fab" when used herein refers to a fragment of an antibody that comprises the constant domain of the light chain and the CHI domain of the heavy chain.

The term "mAb" refers to monoclonal antibody. Antibodies of the invention comprise without limitation whole native antibodies, bispecific antibodies; chimeric antibodies; Fab, Fab', single chain V region fragments (scFv), fusion polypeptides, and unconventional antibodies.

By "specifically binds" is meant a compound or antibody that recognizes and binds a polypeptide of the invention, but which does not substantially recognize and bind other molecules in a sample, for example, a biological sample, which naturally includes a polypeptide of the invention.

As used herein, the term "sensitivity" is the percentage of subjects with a particular disease.

As used herein, the term "specificity" is the percentage of subjects correctly identified as having a particular disease i.e., normal or healthy subjects. For example, the specificity is calculated as the number of subjects with a particular disease as compared to non-cancer subjects (e.g., normal healthy subjects).

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100. mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 2A-2F are plots showing calibration curves of the 6-plex immunoassay. Calibration curves of OPN, MIA, CEACAM-1, MIC-1, SPON1, and HSP27 (shown in FIGS. 2A-2F, respectively) in the 6-plex immunoassay were generated using the 5 parameter (5PL) logistic regression model. "A.U." refers to arbitrary units.

FIGS. 5A-5F are comparisons of the multiplex immunoassay and monoplex immunoassay. A-F, correlations of the 6-plex immunoassay and their respective monoplex immunoassay for measurements of OPN, MIA, CEACAM-1, MIC-1, SPON1 and HSP27.

DETAILED DESCRIPTION OF THE INVENTION

Figure 1A:
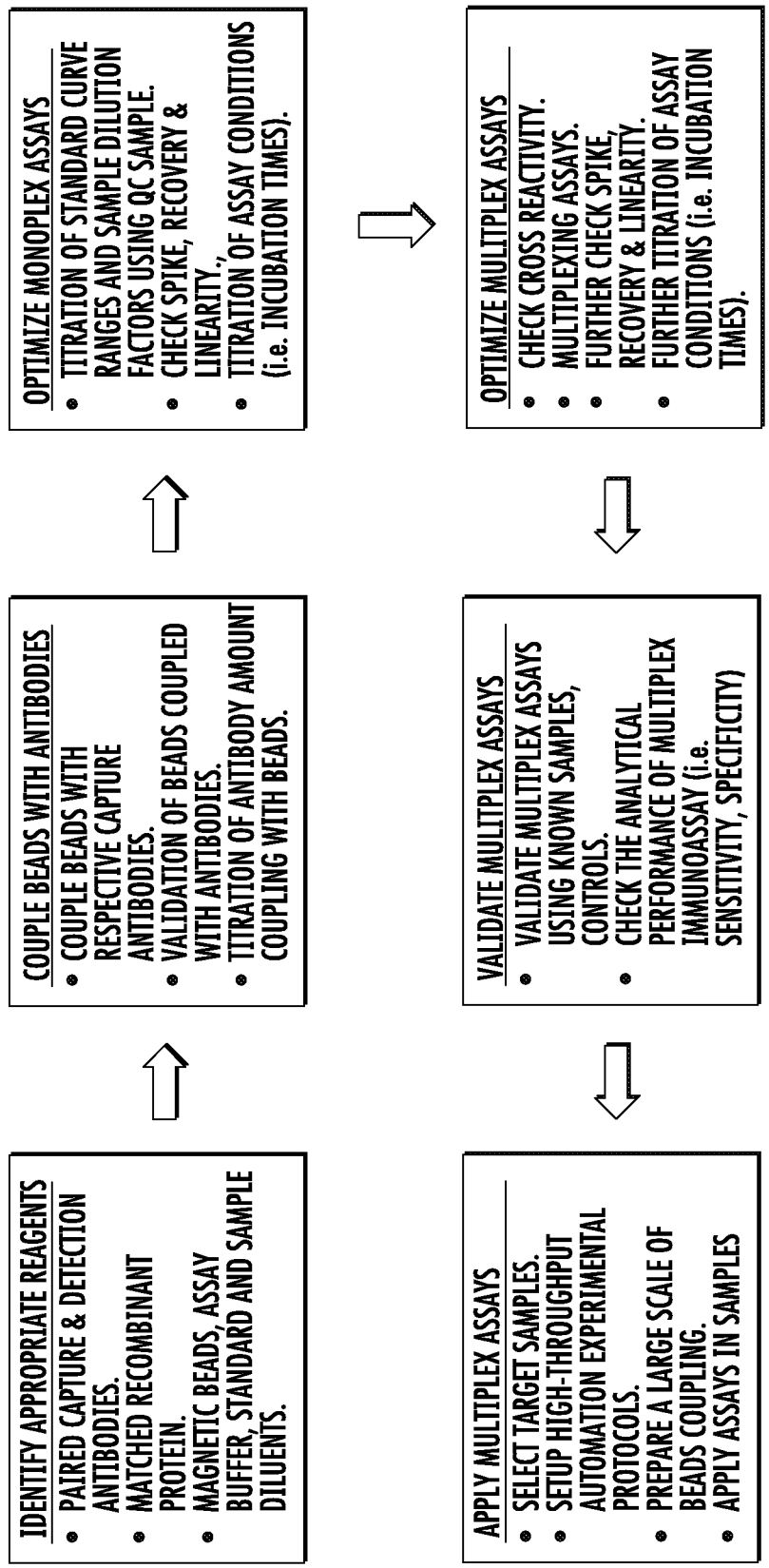
FIGS. 1A-1B are a general view of magnetic bead-based multiplex immunoassay development and application. A, a flowchart of multiplex immunoassay development and application. B, a workflow of mangetic bead-based multiplex immunoassay.

The invention features compositions and methods that are useful for early detection of pancreatic cancer. The invention is based, at least in part, on the discovery of biomarkers (e.g., MIC-1, CEACAM-1, MIA, SPON1) that complement CA19-9, whereby the panel comprising CA19-9 and complementary biomarkers of the invention improve accuracy of detection of pancreatic cancer.

Pancreatic cancer is the 4th leading cause of cancer death in the United States. The majority of patients present with unresectable disease leading a median survival of 6 months and an overall 5-year survival of <5%. The early detection of this disease is critical because surgery at an early stage is the most promising therapy that could greatly improve the prognosis of patients.

Development and Validation of a 6-Plex Immunoassay

Customized magnetic bead-based multiplex immunoassays were developed for the selected candidate serum biomarkers using a Bio-Plex 200 suspension array system. Magnetic bead-based monoplex immunoassays were first developed for OPN, MIA, CEACAM-1, MIC-1, SPON1 and HSP27 using pooled normal human sera. The cross-reactivity studies through single-detection and mutiplexed-detection antibody experiments indicated that the degree of cross-reactivity across the 6 immunoassays was generally <1%, based on the measurements in response to high concentrations of the recombinant proteins at first dilution point (except SPON1 at the third dilution because only 1.4% of sera with SPON1 exceed the third dilution) of the standard curve (Table 2). About 1.3-3.3% of nonspecific cross-reactions were observed in SPON1 antibody against other proteins. But, it should be noted that majority of these nonspecific cross-reactions were observed at recombinant protein concentrations that exceed physiological levels, thereby reducing the chance of cross-reactivity in physiological human serum samples.

By mixing the capture antibody-coupled beads and detection antibodies used in the monoplex immunoassays, a 6-plex immunoassay of OPN, MIA, CEACAM-1, MIC-1, SPON1 and HSP27 was developed and evaluated. The calibration curves of the 6-plex immunoassay generated using the 5PL logistic regression models are shown in FIG. 2A-F. The 6-plex immunoassay results correlated significantly with their respective monoplex immunoassay results (FIGS. 5A-F and Table 3), suggesting that the 6-plex immunoassay was comparable to the monoplex immunoassays in protein quantifications. Furthermore, there were significant correlations of OPN and HSP27 protein measurements using the the 6-plex immunoassay compared with using the commercial ELISA kits (Table 3).

The analytical performance of the 6-plex immunoassay is shown in Table 3, with recovery of 89-104% (standard curve points and QCs), intra-assay precision of 2.1-15.4% (QCs) and inter-assay precision of 3.7-21.5% (QCs). The 6-plex immunoassay exhibited wide dynamic concentration ranges the calibration curves covered (median at 227-fold) defined by LLOQ and ULOQ, and low LOBs for target protein quantifications.

Application of the 6-Plex Immunoassay in the Detection of PDAC

Figure 9A:
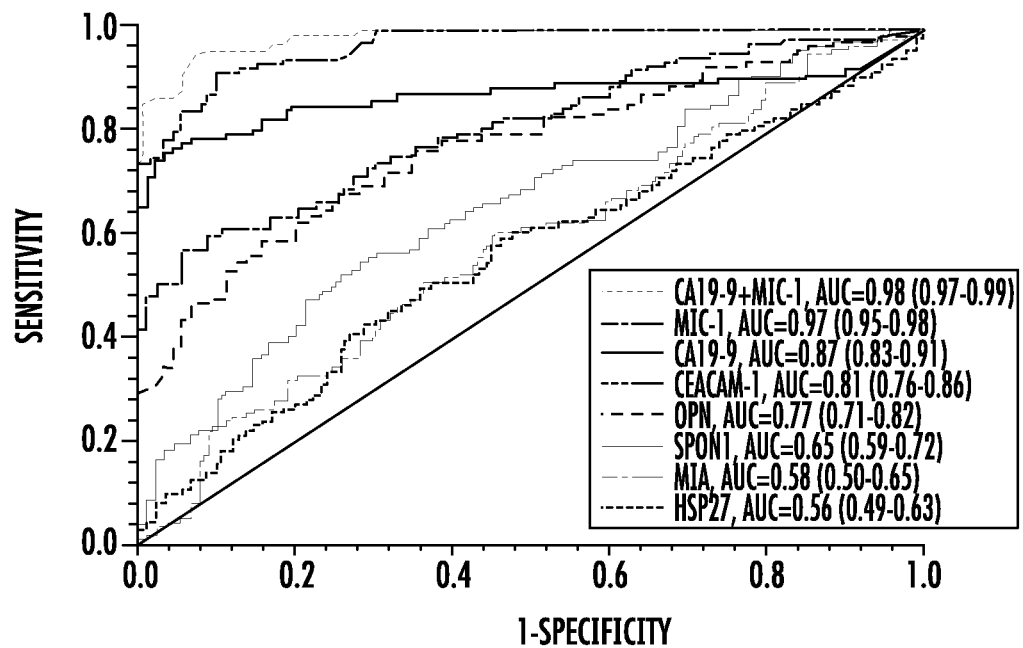
FIGS. 9A-9B are the diagnostic performances of 7 serum biomarkers in detection of PDAC. Diagnostic performances of CA19-9, OPN, MIA, CEACAM-1, MIC-1, SPON1 & HSP27 as individual markers or the combination of two best biomarkers (CA19-9 & MIC-1) in differentiating patients with PDAC versus healthy controls (A) or benign conditions (B). ROC curves with AUCs are presented along with their 95% CI in brackets.
Figure 9B:
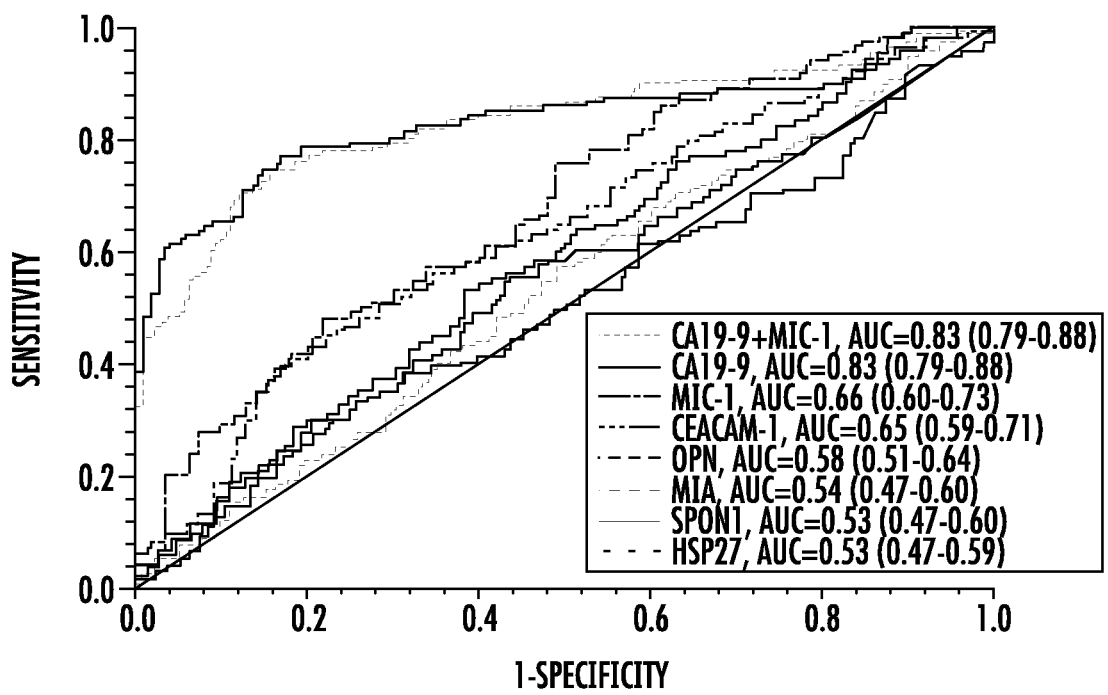

The developed 6-plex immunoassay was applied to analyze the target protein levels in sera of 189 patients diagnosed with PDAC, 131 patients with benign pancreatic conditions, and 89 healthy controls (Table 1). The performances of the individual markers were compared to CA19-9 in discriminating PDAC versus healthy controls or benign conditions (FIG. 6, FIGS. 8-9, and Table 5). Serum levels of OPN, CEACAM-1, MIC-1 SPON1 & CA19-9 were significantly increased in PDAC patients compared to healthy controls (all at $p<0.0001$), but MIA was significantly decreased in PDAC patients compared to healthy controls (p=0.043) (FIG. 8). Serum levels of OPN, CEACAM-1, MIC-1 & CA19-9 were also significantly increased in PDAC patients compared to benign conditions (all p<0.0001, except OPN at p=0.021) (FIG. 8). Individually, the best biomarkers to separate PDAC patients from healthy controls or benign conditions on the ROC analysis were MIC-1 (AUC=0.97, [0.95-0.98]), CA19-9 (0.87, [0.83-0.91]), CEACAM-1 (0.81, [0.76-0.86]) & OPN (0.77, [0.71-0.82]) or CA19-9 (0.83, [0.79-0.88]), MIC-1 (0.66, [0.60-0.73]), CEACAM-1 (0.65, [0.59-0.71]) & OPN (0.58, [0.51-0.64]), respectively (FIG. 9). The combination of CA19-9 with other biomarkers did not show obvious improvement in discriminating PDAC from benign conditions; however the combination of CA19-9 and MIC-1 significantly improve the diagnostic performance of CA19-9 alone in detection of PDAC from healthy controls (only the combination of CA19-9 & MIC-1 on the ROC analysis were shown in Supplement FIG. 2; other combinations of individual biomarkers not shown).

Serum levels of individual biomarkers were further analyzed in different subgroups consisting of 89 healthy controls, 68 chronic pancreatitis, 63 IPMN, 97 PDAC early stage, and 92 PDAC late stage patients (FIG. 6). Demonstrating as the most interesting findings in this study, serum levels of CA19-9, MIC-1 & CEACAM-1 were significantly increased in PDAC early stage compared to chronic pancreatitis patients (CA19-9 at p<0.0001, MIC-1 at p<0.01, and CEACAM-1 at p<0.05) (FIG. 6). Serum levels of CA19-9, MIC-1, CEACAM-1 & OPN were also significantly increased in PDAC early stage compared to IPMN patients (CA19-9 & MIC-1 at p<0.0001, CEACAM-1 at p<0.001, and OPN at p=0.01) (FIG. 4). Individually, the best biomarkers to separate PDAC early stage from pancreatitis or IPMN based on the ROC analysis were CA19-9 (AUC=0.77, [0.70-0.84]), MIC-1 (0.64, [0.55-0.73]), CEACAM-1 (0.60, [0.51-0.69]) & MIA (0.57, [0.49-0.66]) or CA19-9 (AUC=0.81, [0.74-0.88]), MIC-1 (0.73, [0.65-0.81]), CEACAM-1 (0.67, [0.59-0.75]) & OPN (0.64, [0.55-0.73]), respectively (FIG. 5). Logistic regression modeling and ROC analysis selected a five-marker panel of CA19-9, MIC-1, CEACAM-1, MIA & OPN with an AUC=0.84 (0.78-0.90) for PDAC early stage versus pancreatitis or AUC=0.86 (0.80-0.91) for PDAC early stage versus IPMN, which significantly improved the individual biomarker performance (FIG. 7).

In the present invention, the inventors identified a five-marker panel of CA19-9, MIC-1, CEACAM-1, MIA & OPN showing strong diagnostic performances and significant complementarities of these markers with CA19-9 in the detection of early stage PDAC from healthy controls and benign pancreatic conditions. These results provide an advanced validation on the utilities of these serum biomarkers in early detection of PDAC. MIC-1 belongs to transforming growth factor-β superfamily, originally identified in activated macrophages and was found overexpressed in several cancer types. MIC-1 may have anticancer functions, as its promoter region is a target for p53. Koopmann et al reported that serum MIC-1 outperforms CA19-9 in the differention of patients with resectable pancreatic cancer from healthy controls with an AUC=0.99 (MIC-1) versue 0.78 (CA19-9) but not from chronic pancreatitis (0.81 versue 0.74). CEACAM-1 is a member of the human carcinoembryonic antigen (CEA) family. The CEACAM subgroup members belong to the immunoglobulin superfamily of adhesion molecules. CEACAM1 is expressed in a number of epithelia, granulocytes, and lymphocytes, and the expression of CEACAM-1 was also reported in different cancer types. CEACAM-1 plays an important role in the regulation of tumor growth, angiogenesis, and immune modulation. OPN is a glycophosphoprotein normally produced and secreted into most body fluids by osteoblasts, arterial smooth muscle cells, various epithelia, activated T cells and macrophages, and was often found overexpressed in different cancer types. OPN is most likely related to tumorigenesis, cancer cell proliferation and progression, migration and invasion, protection from apoptosis, and enhancement of metastatic ability. MIA is a small secreted protein coded by a single copy gene on chromosome 19q13.31-q13.33 and acts as an autocrine growth factor. MIA is strongly expressed by malignant melanoma cells and interacts with extracellular matrix proteins. Its overexpreesion promotes the metastatic behaviour of malignant melanoma. MIA was found overexpressed in pancreatic cancer and has the potential of promoting the invasiveness of pancreatic cancer cells, but its serum level were not significantly different between healthy donors and pancreatic cancer patients.

In the present invention, a 6-plex immunoassay of OPN, MIA, CEACAM-1, MIC-1, SPON1 and HSP27 was in-house developed, validated, and applied to a set of serum samples of PDAC patients, benign pancreatic conditions and healthy controls to evaluate their performances individually or in combination on their capacity to complement CA19-9 in early detection of pancreatic cancer. The assay was characterized by LOB/LLOQ, cross-reactivity, recovery, intra- and inter-assay precision; and demonstrated wide dynamic ranges for the target protein measurements that significantly correlated with their respective monoplex assays and/or commercial ELISAs. The assay shows advantages over traditional ELISA and other antibody-based approaches in both multiplexing and flexibility. It measures 6 candidate proteins in only 12.5 µL of serum, and could include more candidate proteins into the panel as soon as appropriate pairs of capture and detection antibodies become available. It is important to note a few general considerations for the development of a multiplex immunoassay of human serum biomarkers. First, due to the different abundances of the candidate proteins in human serum, the effective biological range of each protein must be considered to ensure the fluorescence signal falling into the dynamic range of the assay. A more sensitive assay is needed for one protein with low abundance in the 6-plex immunoassay such as MIA, while a less sensitive assay may be required for another protein which may be of high abundance in the same multiplex immunoassay such as OPN. The sensitivity of each assay may be affected by the affinity/amount of the capture antibody and the amount of capture beads used for that protein. Second, antibody characteristics such as affinity and specificity are critical for the performance of a multiplex immunoassay. All pairs of capture and detection antibodies used in this study have been tested as compatible in the sandwich ELISA for human serum samples. The majority of the capture antibodies used in this study were monoclonal antibodies which are potentially more specific than polyclonal antibodies. All of the detection antibodies except SPON1 used in this study were commercially available biotinylated antibodies. Third, the performance of the multiplex immunoassays is more analyte and sample matrix dependent compared to monoplex immunoassays. Improper storage and non-optimal sample dilutions of serum samples can influence concentration measurements of some selected proteins in a complex sample matrix. It is vital to properly store serum samples at −80° C. prior to the analysis and avoid repeated freeze-thawing of serum samples.

In summary, a magnetic bead-based multiplex immunoassay was developed demonstrating sufficient analytical performance to evaluate serum biomarkers that may complement CA19-9 in early detection of PDAC. The biomarker panels identified in this study warrant additional clinical validation to determine their role in early detection of pancreatic cancer, which could lead to earlier intervention and better outcomes.

Pancreatic Cancer Treatment

The present invention provides methods of selecting a subject for pancreatic cancer treatment. Pancreatic cancer treatment includes, without limitation, surgery and/or administration of chemotherapeutic agent(s) to the subject. In one embodiment, the pancreatic cancer treatment is surgery. Chemotherapeutic agents suitable for treating pancreatic cancer include, without limitation, gemcitabine, 5-fluorouracil, irinotecan, oxaliplatin, paclitaxel, capecitabine, cisplatin, and docetaxel. Pancreatic cancer treatment comprising chemotherapeutic methods of (which include prophylactic treatment) in general comprise administration of a therapeutically effective amount of a chemotherapeutic agent to a subject (e.g., animal, human) in need thereof, including a mammal, particularly a human.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Such treatment (surgery and/or chemotherapy) will be suitably administered to subjects, particularly humans, suffering from, having, susceptible to, or at risk for pancreatic cancer or disease, disorder, or symptom thereof. Determination of those subjects "at risk" can be made by any objective or subjective determination by a diagnostic test or opinion of a subject or health care provider (e.g., genetic test, enzyme or protein marker, a marker (as defined herein), family history, and the like). In particular embodiments, determination of subjects susceptible to or having a pancreatic cancer is determined by measuring levels of at least one of the markers of the invention (e.g., CA19-9, MIA, MIC-1, CEACAM-1, OPN, SPON1, HSP27, POSTN, or LGALS3BP). In particular embodiments, a subject determined susceptible to or having a pancreatic cancer is selected for surgery.

Diagnostics

The present invention provides a number of diagnostic assays that are useful for early detection of pancreatic cancer in a subject. Current existing serum markers for pancreatic cancer such as CA19-9 lack the necessary sensitivity and specificity. Accordingly, the present invention provides other markers (e.g., MIA, MIC-1, CEACAM-1, OPN, SPON1, HSP27, POSTN, LGALS3BP) which are useful individually, in any combination with each other, or in any combination with CA19-9 for the detection of pancreatic cancer.

The presence or absence of the herein disclosed marker(s) is measured in a biological sample from a subject. Biological samples that are used to evaluate the presence or absence of the herein disclosed markers include without limitation blood, serum, plasma, urine. In one embodiment, the biological sample is serum.

While the examples provided below describe specific methods of detecting levels of these markers, the skilled artisan appreciates that the invention is not limited to such methods. The biomarkers of this invention can be detected by any suitable method. For example, marker levels are quantifiable by any standard method, such methods include, but are not limited to real-time PCR, Southern blot, PCR, mass spectroscopy, and/or antibody binding.

The methods described herein can be used individually or in combination for a more accurate detection of the biomarkers (e.g., immunoassay, mass spectrometry, and the like). The accuracy of a diagnostic assay can be characterized by a Receiver Operating Characteristic curve ("ROC curve"). An ROC is a plot of the true positive rate against the false positive rate for the different possible cutpoints of a diagnostic test. An ROC curve shows the relationship between sensitivity and specificity. That is, an increase in sensitivity will be accompanied by a decrease in specificity. The closer the curve follows the left axis and then the top edge of the ROC space, the more accurate the test. Conversely, the closer the curve comes to the 45-degree diagonal of the ROC graph, the less accurate the test. The area under the ROC is a measure of test accuracy. The accuracy of the test depends on how well the test separates the group being tested into those with and without the disease in question. An area under the curve (referred to as "AUC") of 1 represents a perfect test, while an area of 0.5 represents a less useful test. In certain embodiments, biomarkers and diagnostic methods of the present invention have an AUC greater than 0.50. In other embodiments, biomarkers and diagnostic methods of the present invention have an AUC greater than 0.60. In other embodiments, biomarkers and diagnostic methods of the present invention have an AUC greater than 0.70. Exemplary combinations of markers (or panels of biomarkers) of the invention include, without limitation, the combination CA19-9 and MIA; the combination CA19-9 and SPON1; the combination CA19-9 and MIC-1; and, the combination CA19-9 and CEACAM-1. Exemplary combinations of markers (or panels of biomarkers) of the invention include, without limitation, the combination CA19-9, HSP27, and MIA1. Exemplary combinations of markers (or panels of biomarkers) of the invention include, without limitation, the combination CA19-9, CEACAM-1, MIC-1, SPON1 and MIA.

In particular embodiments, the biomarkers of the invention (e.g., CA19-9, MIA, MIC-1, CEACAM-1, OPN, SPON1, HSP27, POSTN, LGALS3BP) are measured by immunoassay. Immunoassay typically utilizes an antibody (or other agent that specifically binds the marker) to detect the presence or level of a biomarker in a sample. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, Western blot, sandwich immunoassays including ELISA and other enzyme immunoassays, fluorescence-based immunoassays, and chemiluminescence. Other forms of immunoassay include magnetic immunoassay, radioimmunoassay, and real-time immunoquantitative PCR (iqPCR).

Immunoassays can be carried out on solid substrates (e.g., chips, beads, microfluidic platforms, membranes) or on any other forms that supports binding of the antibody to the marker and subsequent detection. A single marker may be detected at a time or a multiplex format may be used. Multiplex immunoanalysis may involve planar microarrays (protein chips) and bead based microarrays (suspension arrays).

In particular embodiments, the immunoassay is carried out using multiplexed bead assays. In particular embodiments, the immunoassay is carried out using magnetic bead-based multiplexed assays. Multiplexed bead assays use a series of spectrally discrete particles that are used to capture and quantitate soluble analytes. The analyte is then measured by detection of a fluorescence-based emission and flow cytometric analysis. Multiplexed bead assays generate data that is comparable to ELISA based assays, but in a multiplexed or simultaneous fashion. Concentration of unknowns is calculated for the cytometric bead array as with any sandwich format assay, i.e., through the use of known standards and by plotting unknowns against a standard curve. Further, multiplexed bead assays allow quantification of soluble analytes in samples never previously considered due to sample volume limitations. In addition to the quantitative data, powerful visual images are generated revealing unique profiles or signatures that provide the user with additional information at a glance.

In particular embodiments, subjects are characterized as having an increased level of CA19-9. In particular embodiments, subjects are characterized as having an increased level of MIA. In particular embodiments, subjects are characterized as having an increased level of MIC-1. In particular embodiments, subjects are characterized as having an increased level of CEACAM-1. In particular embodiments, subjects are characterized as having an increased level of OPN. In particular embodiments, subjects are characterized as having an increased level of SPON1.

In particular embodiments, subjects are characterized as having an increased level of CA19-9 and at least one of the markers selected from the group consisting of: MIA, MIC-1, CEACAM-1, OPN, SPON1, HSP27, POSTN, and LGALS3BP. In particular embodiments, subjects are characterized as having increased levels of CA19-9 and MIA. In particular embodiments, subjects are characterized as having increased levels of CA19-9 and MIC-1. In particular embodiments, subjects are characterized as having increased levels of CA19-9 and CEACAM-1. In particular embodiments, subjects are characterized as having increased levels of CA19-9 and SPON1.

In particular embodiments, subjects are characterized as having an increased level of the combination of markers CA19-9, HSP27, and MIA1. In particular embodiments, subjects are characterized as having an increased level of the combination of markers CA19-9, CEACAM-1, MIC-1, SPON1 and MIA.

In particular embodiments, the level of a marker is compared to a reference. In one embodiment, the reference is the level of marker present in a control sample obtained from a patient that does not have a pancreatic cancer. In some examples of the disclosed methods, when the level of expression of a biomarker(s) is assessed, the level is compared with the level of expression of the biomarker(s) in a reference standard. By reference standard is meant the level of expression of a particular biomarker(s) from a sample or subject lacking a pancreatic cancer, at a selected stage of pancreatic cancer or other pancreatic condition (e.g., pancreatitis, intraductal papillary mucinous neoplasm (IPMN), early stage or late stage pancreatic ductal adenocarcinoma (PDAC)) or in the absence of a particular variable such as a therapeutic agent. Alternatively, the reference standard comprises a known amount of biomarker. Such a known amount correlates with an average level of subjects lacking a cancer, at a selected stage of pancreatic cancer or pancreatic condition, or in the absence of a particular variable such as a therapeutic agent. A reference standard also includes the expression level of one or more biomarkers from one or more selected samples or subjects as described herein. For example, a reference standard includes an assessment of the expression level of one or more biomarkers in a sample from a subject that does not have a pancreatic cancer, is at a selected stage of progression of a pancreatic cancer, or has not received treatment for a pancreatic cancer. Another exemplary reference standard includes an assessment of the expression level of one or more biomarkers in samples taken from multiple subjects that do not have a pancreatic cancer, are at a selected stage of progression of a pancreatic cancer (e.g., pancreatitis, intraductal papillary mucinous neoplasm (IPMN), early stage or late stage pancreatic ductal adenocarcinoma (PDAC)), or have not received treatment for pancreatic cancer.

In one embodiment, the invention provides a method of monitoring treatment progress. The method includes the step of determining a level of diagnostic marker ("Marker") (e.g., CA19-9, MIA, MIC-1, CEACAM-1, OPN, SPON1, HSP27, POSTN, LGALS3BP) or diagnostic measurement (e.g., screen, assay) in a subject suffering from or susceptible to a disorder or symptoms thereof associated with pancreatic cancer, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In some embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Kits

The invention provides kits for detecting a pancreatic cancer in a subject and/or characterizing a pancreatic cancer status in a subject. A diagnostic kit of the invention provides a reagent (e.g., an antibody or antigen binding fragment thereof that selectively bind a marker of the invention) for measuring relative expression of a marker (e.g., CA19-9, MIA, MIC-1, CEACAM-1, OPN, SPON1, HSP27, POSTN, LGALS3BP). In other embodiments, the kit further includes reagents suitable for CA19-9, MIA, MIC-1, CEACAM-1, OPN, SPON1, HSP27, POSTN, or LGALS3BP immunoassay.

In one embodiment, the kit includes a diagnostic composition comprising a capture reagent detecting a CA19-9 polysaccharide and a capture reagent detecting at least one marker selected from the group consisting of a MIA polynucleotide or polypeptide, a MIC-1 polynucleotide or polypeptide, a CEACAM-1 polynucleotide or polypeptide, a OPN polynucleotide or polypeptide, a SPON1 polynucleotide or polypeptide, a HSP27 polynucleotide or polypeptide, a POSTN polynucleotide or polypeptide, and a LGALS3BP polynucleotide or polypeptide. In one embodiment, the capture reagent detecting a CA19-9 polysaccharide is an anti-CA19-9 antibody or an antigen-binding fragment thereof. In one embodiment, the capture reagents are fixed to a substrate. In one embodiment, the substrate is a magnetic bead. In one embodiment, the kit includes a diagnostic composition comprising an anti-CA19-9 antibody or an antigen-binding fragment thereof and at least one antibody or antigen-binding fragment thereof selected from: an anti-MIC-1 antibody, an anti-CEACAM-1 antibody, an anti-MIA antibody, and an anti-SPON1 antibody. In one embodiment, the kit includes a diagnostic composition comprising an anti-CA19-9 antibody or an antigen-binding fragment thereof, an anti-HSP27 antibody or an antigen-binding fragment thereof, and an anti-MIA antibody or an antigen-binding fragment thereof. In one embodiment, the kit includes a diagnostic composition comprising an anti-CA19-9 antibody or an antigen-binding fragment thereof, an anti-CEACAM-1 antibody or an antigen-binding fragment thereof, an anti-MIC-1 antibody or an antigen-binding fragment thereof, an anti-SPON1 antibody or an antigen-binding fragment thereof, and an anti-MIA antibody or an antigen-binding fragment thereof.

The kits may be in combination with a therapeutic composition comprising an chemotherapeutic agent suitable for treating pancreatic cancer. In one embodiment, the kit includes a diagnostic composition and a therapeutic composition comprising a chemotherapeutic agent.

In some embodiments, the kit comprises a sterile container which contains a therapeutic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, the kit further comprises instructions for administering the therapeutic combinations of the invention. In particular embodiments, the instructions include at least one of the following: description of the therapeutic agent; dosage schedule and administration for enhancing anti-tumor activity; precautions; warnings; indications; counter-indications; over dosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Examples/Methods

Example 1: Development of Magnetic Bead-Based Multiplex Immunoassay Comprising a Three Marker Panel of CA19-9, HSP27, and MIA to Evaluate Serum Biomarkers for the Early Detection of Pancreatic Cancer Pancreatic cancer is the 4th leading cause of cancer death in the United States. The majority of patients present with unresectable disease leading a median survival of 6 months and an overall 5-year survival of <5%. The early detection of this disease is critical because surgery at an early stage is the most promising therapy that could greatly improve the prognosis of patients. The current existing serum markers such as CA19-9 lack the necessary sensitivity and specificity. Multiplex immunoassay simultaneously measuring multiple analytes in the same sample using minimum volume allows evaluation of serum biomarker panels that can potentially complement CA19-9 in early detection of pancreatic cancer. The study described herein is aimed at developing magnetic bead-based multiplex immunoassays to evaluate serum biomarkers for the early detection of pancreatic cancer.

Curated results from PUBMED database search using a combination of terms "pancreatic cancer, pancreatic neoplasm, PANIN, pancreatic adenocarcinoma, sensitivity, and fold change" were analyzed. Candidate biomarkers were selected using a weighted scoring system based on 1) fold changes and number of publications, or 2) sensitivity/specificity and study sample sizes. Magnetic bead-based multiplex immunoassays were developed for the selected candidate serum biomarkers using a Bio-Plex 200 suspension array system (Bio-Rad). Briefly, monoplex assays of individual candidates were first developed, cross-reactivity checked, and multiplex assays validated and optimized. All of these proteins plus HE4 (Roche) and CA19-9 (Tosoh) were analyzed in sera of patients diagnosed with pancreatic ductal adenocarcinoma (PDAC: IB/IIA/IIB, n=10; IV, n=10), benign pancreatic conditions including intraductal papillary mucinous neoplasm (IPMN, n=10) and chronic pancreatitis (n=10), and healthy controls (n=19). The performances of these candidate markers were evaluated individually or in combination on their capacity to complement CA19-9 in early detection of pancreatic cancer.

The biomarkers evaluated included 1) a 5-plex assay of OPN, CEACAM-1, MIC-1, MIA, and SPON1; 2) a 2-plex assay of POSTN and HSP27; and 3) a monoplex assay of LGALS3BP. These assays were all in-house developed with negligible crossreactivity, recovery of 75-119%, and intra-assay or inter-assay precision of 0.3-9.6% or 0-18%, respectively. LOD or LLOQ was 0.179 ng/mL or 0.181 ng/mL (OPN), 0.101 ng/mL or 0.213 ng/mL (CEACAM-1), 0.001 ng/mL or 0.046 ng/mL (MIC-1), 0.009 ng/mL or 0.016 ng/mL (MIA), 0.041 ng/mL or 0.191 ng/mL (SPON1), 0.094 ng/mL or 0.767 ng/mL (POSTN), 0.005 ng/mL or 0.062 ng/mL (HSP27), and 0.035 ng/mL or 0.289 ng/mL (LGALS3BP). Individually, the best biomarkers (AUC in ROC analysis, 95% CI) to separate PDAC from benign pancreatic conditions were CA19-9 (0.9425, [0.85-1.00]), CEACAM (0.845, [0.71-0.98]), MIC (0.79, [0.65-0.93]), and SPON1 (0.68, [0.51-0.85]). However, stepwise backward logistic regression selected a three marker panel of CA19-9, HSP27, and MIA (p-values: <3E-9, <0.03, <0.01, respectively) with an AUC=0.99 [0.97-1.00]. Probably due to the small sample size, the improvement over CA19-9 alone is not statistically significantly.

The multiplex immunoassay workflow provides sufficient analytical performance to evaluate serum biomarker panels that complement CA19-9 in early detection of pancreatic cancer.

Figure 1B:
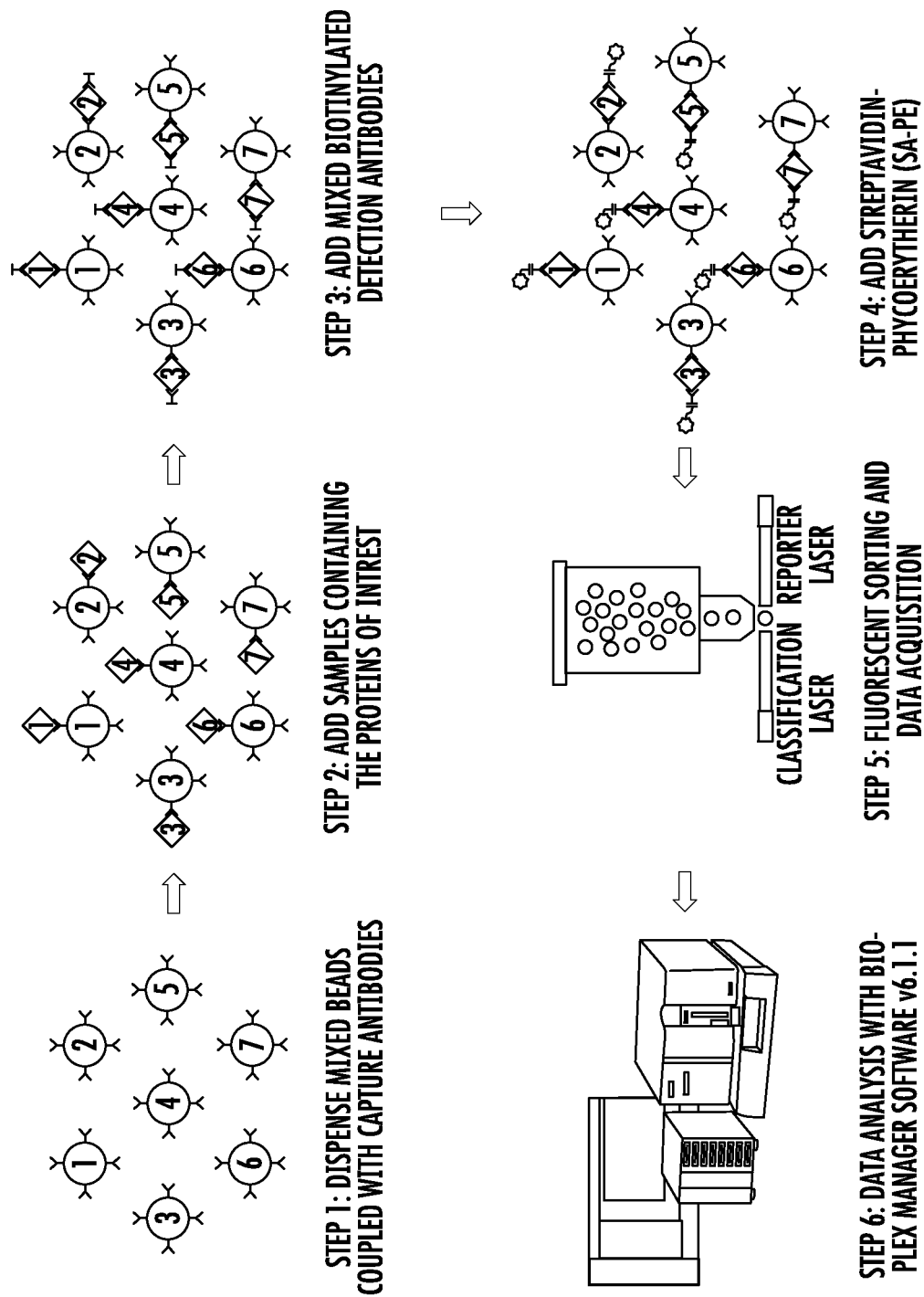
Figure 3B:
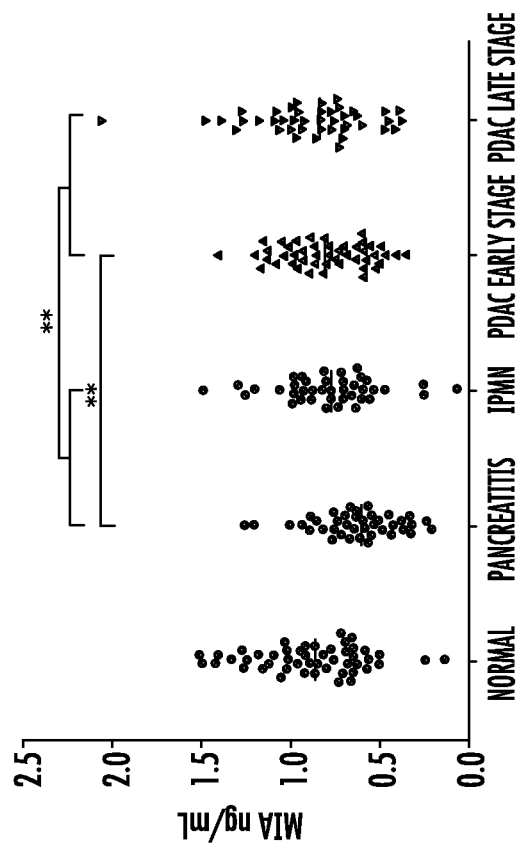
FIGS. 3A-3G are scatter plots of 7 serum biomarker levels in this cohort. Only serum levels of biomarkers demonstrating significant differences between pancreatitis or intraductal papillary mucinous neoplasm (IPMN) and pancreatic ductal adenocarcinoma (PDAC) early stage (or benign and PDAC) are asterisked (Mann-Whitney U test). Bars indicate median value. *, $p<0.05$; , $p<0.01$; *, $p<0.001$; *, $p<0.0001$.
Figure 3D:
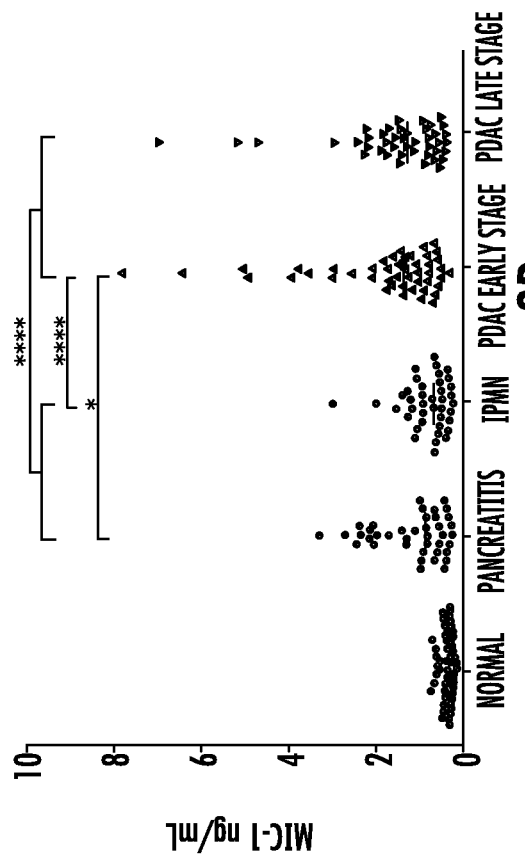
Figure 3A:
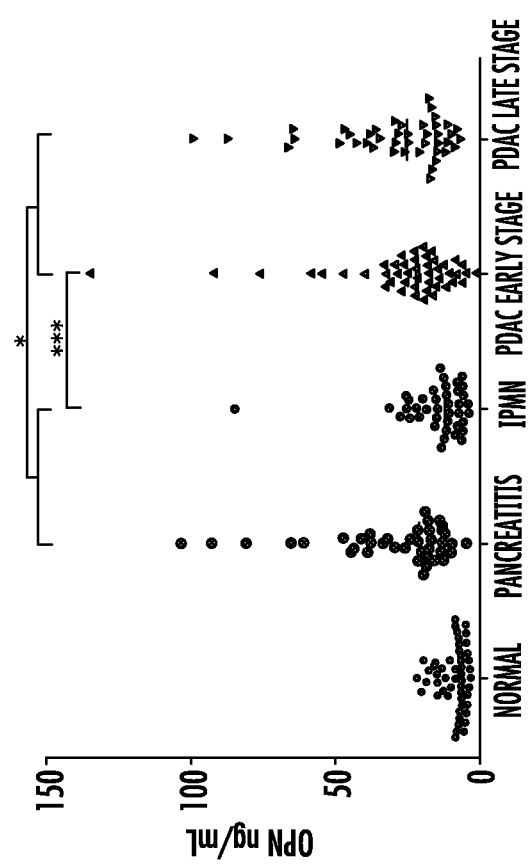
Figure 3C:
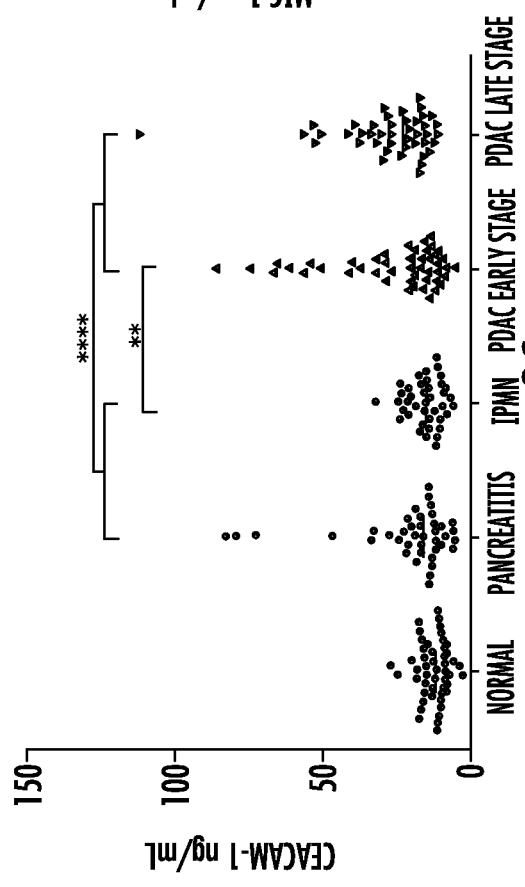
Figure 3F:
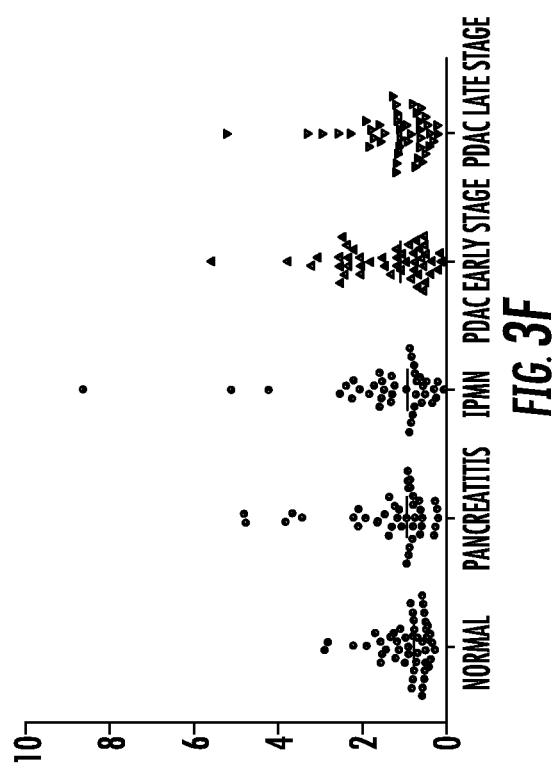
Figure 3E:
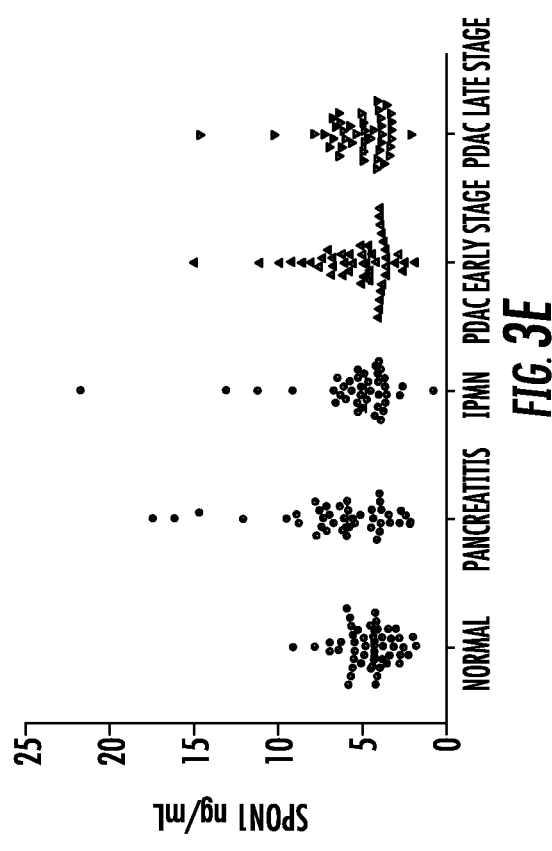
Figure 3G:
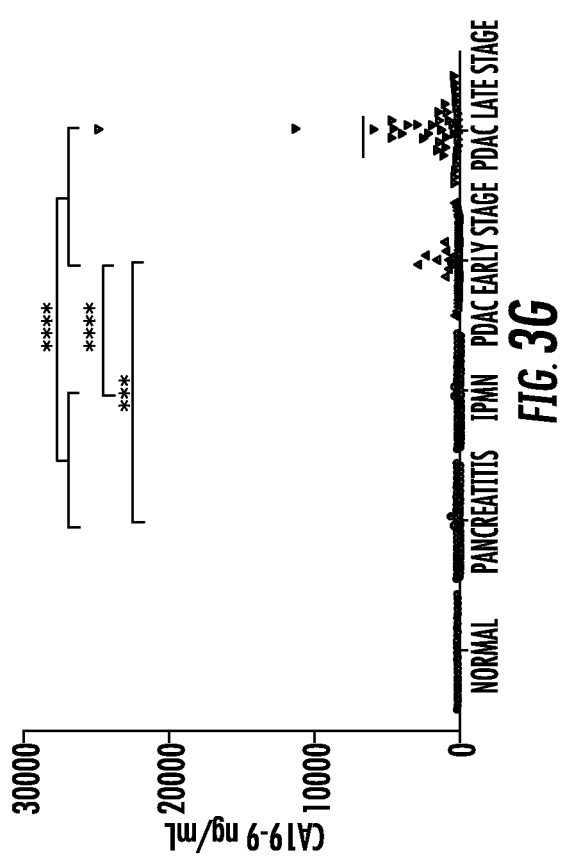

Example 2: Development of Magnetic Bead-Based Multiplex Immunoassay Comprising a Five Marker Panel of CA19-9, MIA, SPON1, MIC-1 and CEACAM-1 to Evaluate Serum Biomarkers for the Early Detection of Pancreatic Cancer Curated results from PUBMED database search using a combination of terms "pancreatic cancer, pancreatic neoplasm, PANIN, pancreatic adenocarcinoma, sensitivity, and fold change" were analyzed. Candidate biomarkers were selected using a weighted scoring system based on 1) fold changes and number of publications, or 2) sensitivity/specificity and study sample sizes. Magnetic bead-based multiplex immunoassays were developed for the selected candidate serum biomarkers using a Bio-Plex 200 suspension array system (Bio-Rad). Briefly, monoplex assays of individual candidates were first developed, cross-reactivity checked, and multiplex assays validated and optimized (FIG. 1). All of these proteins plus CA19-9 (Tosoh) were analyzed in sera of patients diagnosed with pancreatic ductal adenocarcinoma (PDAC: IA/IB/IIA/IIB, 11/13/10/13; III/IV, 3/40), benign pancreatic conditions including intraductal papillary mucinous neoplasm (IPMN, 40) and chronic pancreatitis (40), and healthy controls (49). The performances of these candidate markers were evaluated individually or in combination on their capacity to complement CA19-9 in early detection of pancreatic cancer.

Figure 4A:
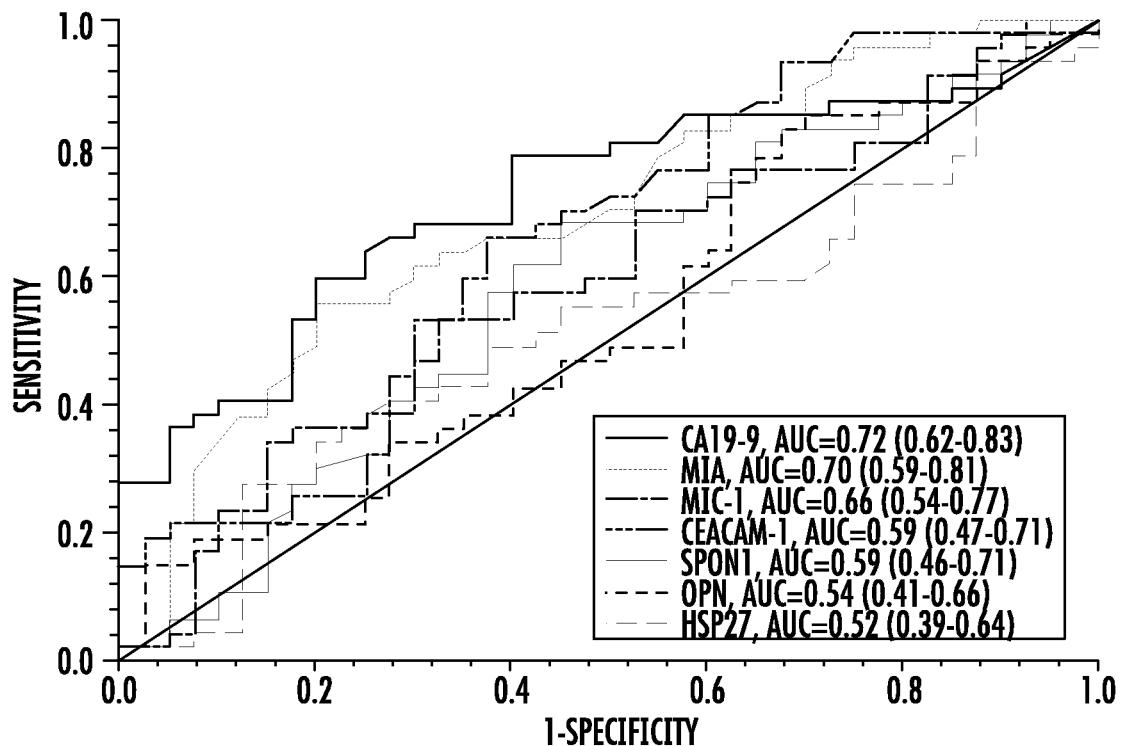
FIGS. 4A-4D are plots showing diagnostic performances of CA19-9, OPN, MIA, CEACAM-1, MIC-1, SPON1 and HSP27 as individual markers (FIGS. 4A and 4C) and their complementary (FIGS. 4B and 4D) in differentiating patients with pancreatic ductal adenocarcinoma (PDAC) early stage versus pancreatitis (FIGS. 4A and 4B) or intraductal papillary mucinous neoplasm (IPMN) (FIGS. 4C and 4D). Receiver operating characteristic (ROC) curves with areas under the curve (AUCs) are presented along with their 95% confidence interval (CI) in brackets. Logistic regression modeling and ROC analysis selected a five-marker panel of CA19-9, CEACAM-1, MIC-1, SPON1 & MIA with an AUC=0.86 (0.79-0.94) for pancreatitis versus PDAC early stage or AUC=0.88 (0.81-0.95) for IPMN versus PDAC early stage, which significantly improved the individual biomarker performance (p value: 0.0094, 0.0003, 0.0018, 0.0001 & 0.0008 for pancreatitis versus PDAC early stage; and 0.0276, 0.0001, 0.0117, <0.0001 & <0.0001 for IPMN versus PDAC early stage; Delong test).
Figure 4B:
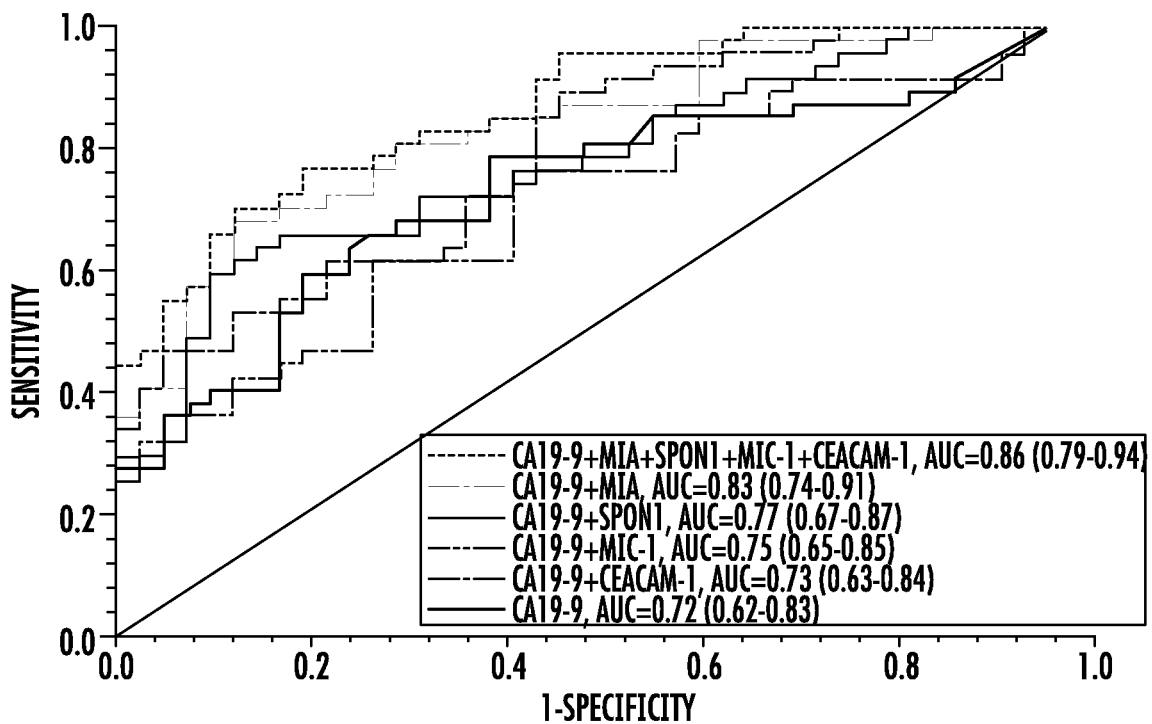
Figure 4C:
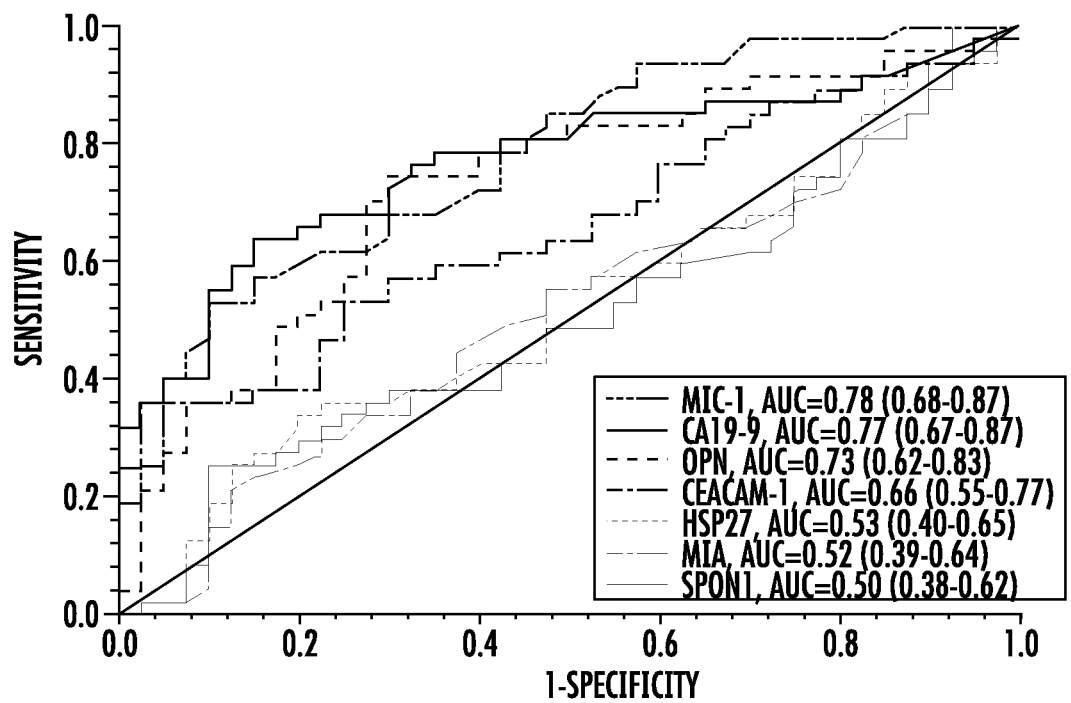
Figure 4D:
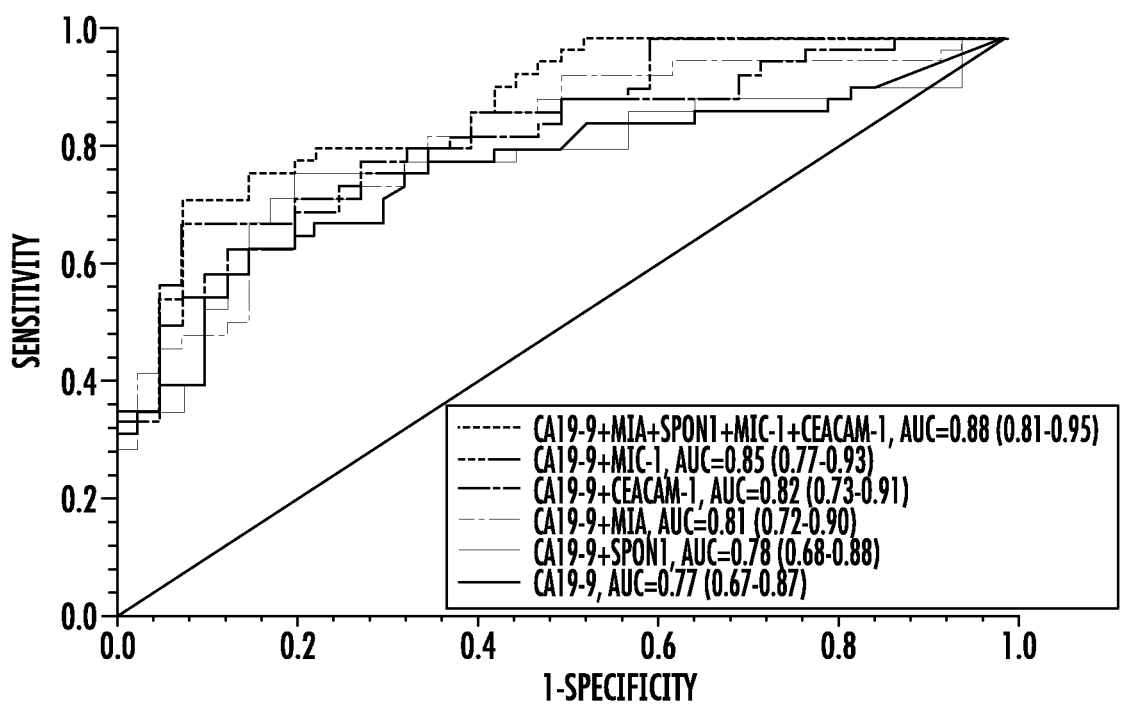
Figure 6A:
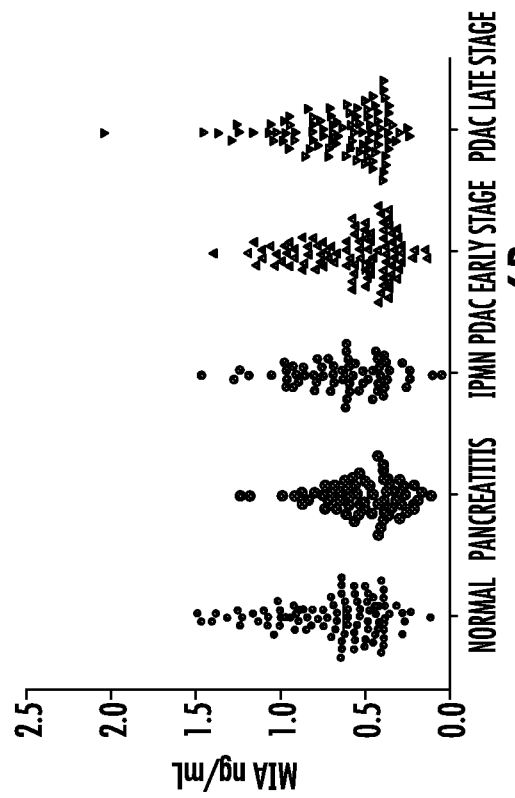
FIGS. 6A-6G are an analysis of biomarkers in sera from PDAC patients, benign conditions, and healthy controls. A-F, expressions of OPN, MIA, CEACAM-1, MIC-1, SPON1, HSP27 and CA19-9 in PDAC patients, benign conditions, and healthy controls. Only serum levels of biomarkers demonstrating significant differences between pancreatitis or IPMN and PDAC early stage (or benign and PDAC) are asterisked (Mann-Whitney U test). Bars indicate median value. *, $p<0.05$; , $p<0.01$; *, $p<0.001$; ****, $p<0.0001$.
Figure 6C:
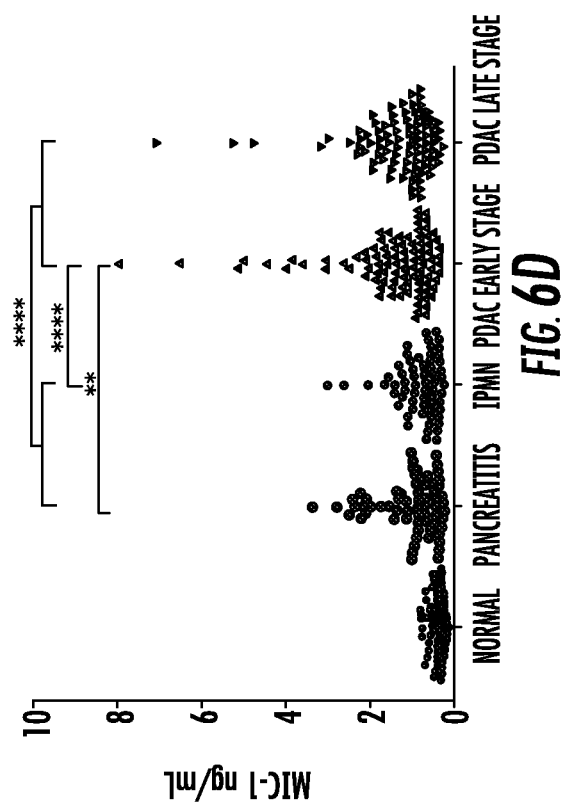
Figure 6B:
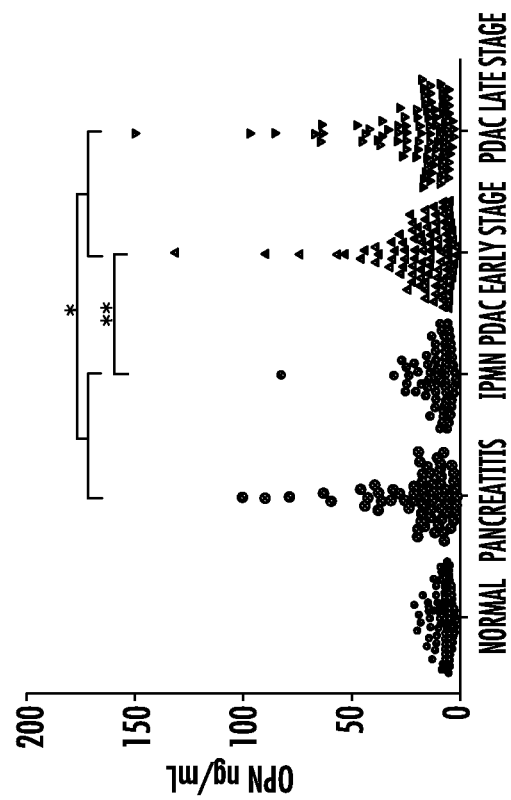
Figure 6D:
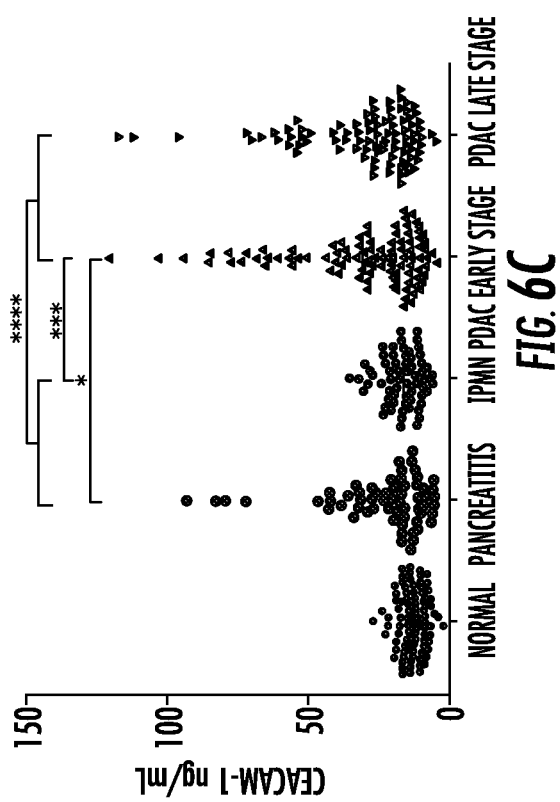
Figure 6F:
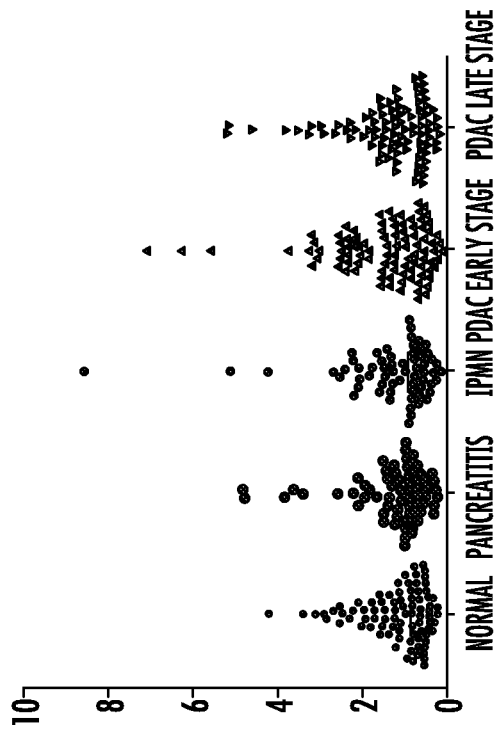
Figure 6E:
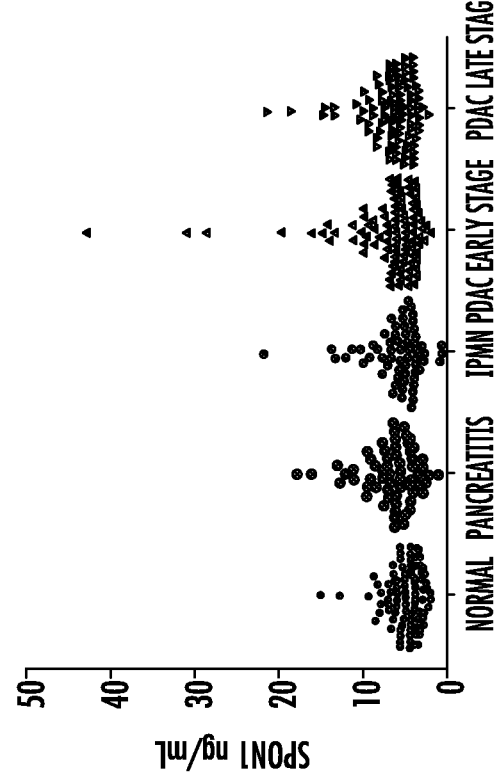
Figure 6G:
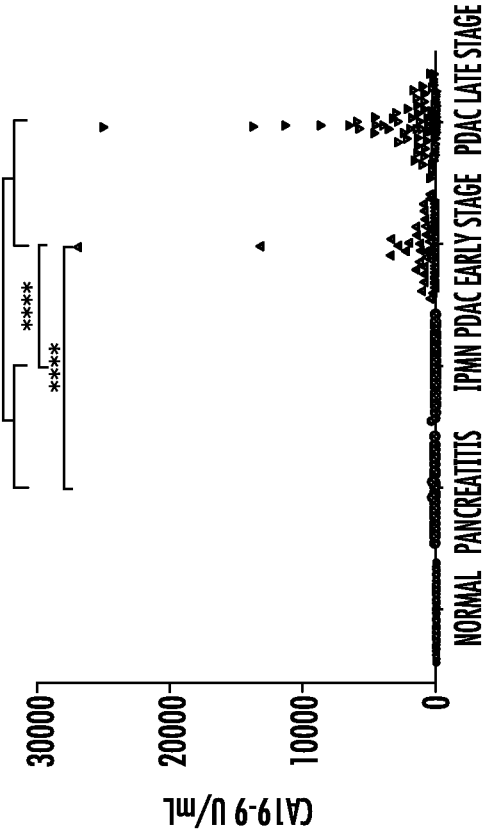
Figure 7A:
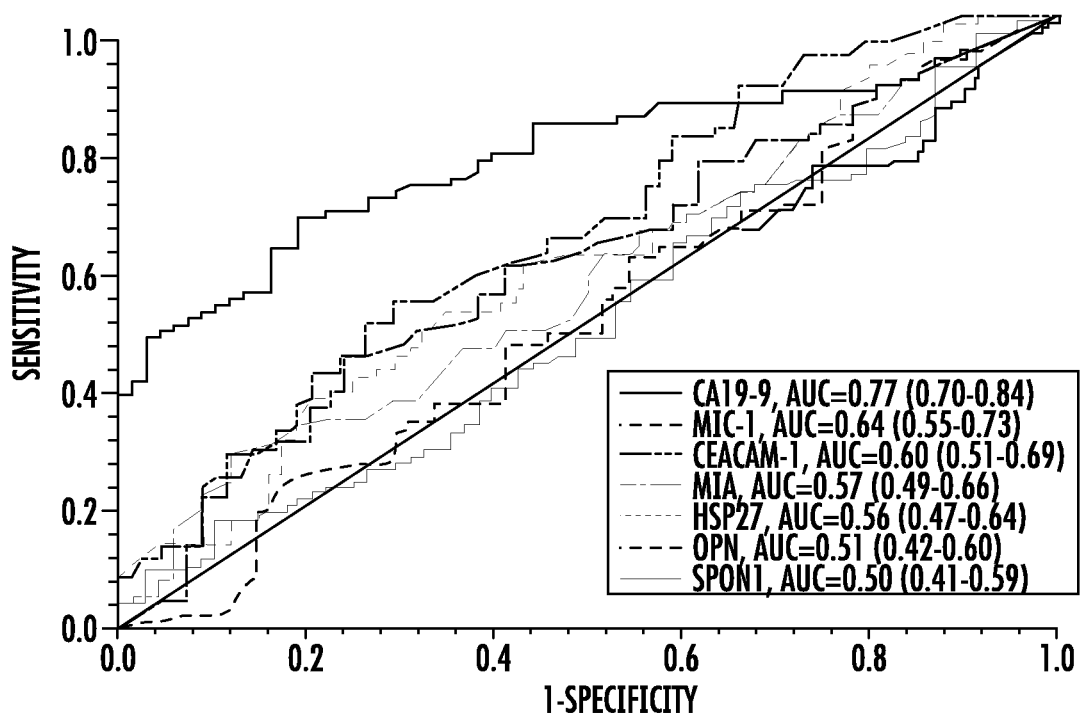
FIGS. 7A-7D are the diagnostic performances of individual or combination of serum biomarkers in detection of PDAC early stage. Diagnostic performances of CA19-9, OPN, MIA, CEACAM-1, MIC-1, SPON1 & HSP27 as individual markers (A&C) and their complementary (B&D) in differentiating patients with PDAC early stage versus pancreatitis (A&B) or IPMN (C&D). ROC curves with AUCs are presented along with their 95% CI in brackets. Logistic regression modeling and ROC analysis selected a five-marker panel of CA19-9, MIC-1, CEACAM-1, MIA & OPN with an AUC=0.84 (0.78-0.90) for pancreatitis versus PDAC early stage or AUC=0.86 (0.80-0.91) for IPMN versus PDAC early stage, which significantly improved the individual biomarker performance.
Figure 7B:
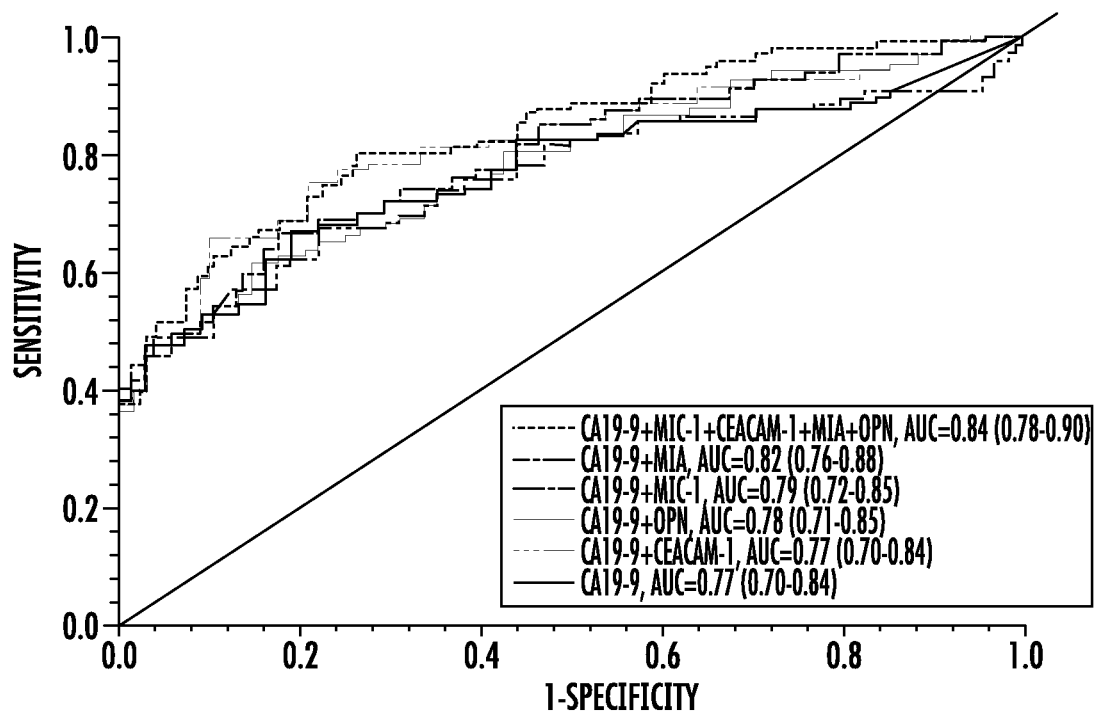
Figure 7C:
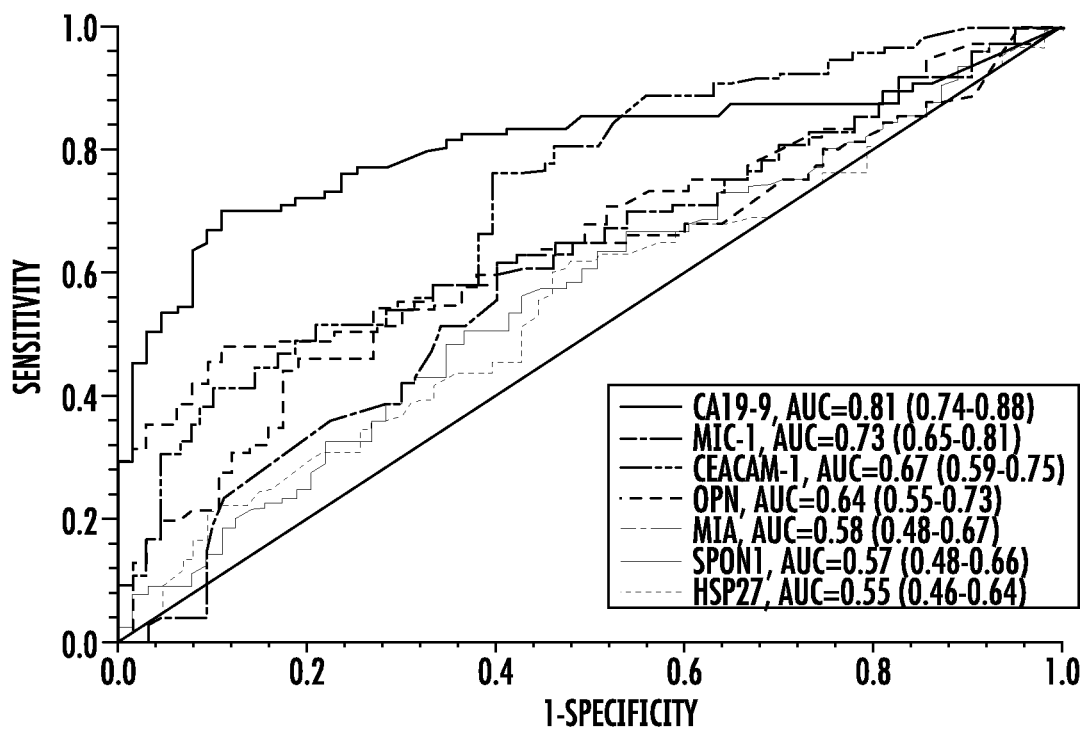
Figure 7D:
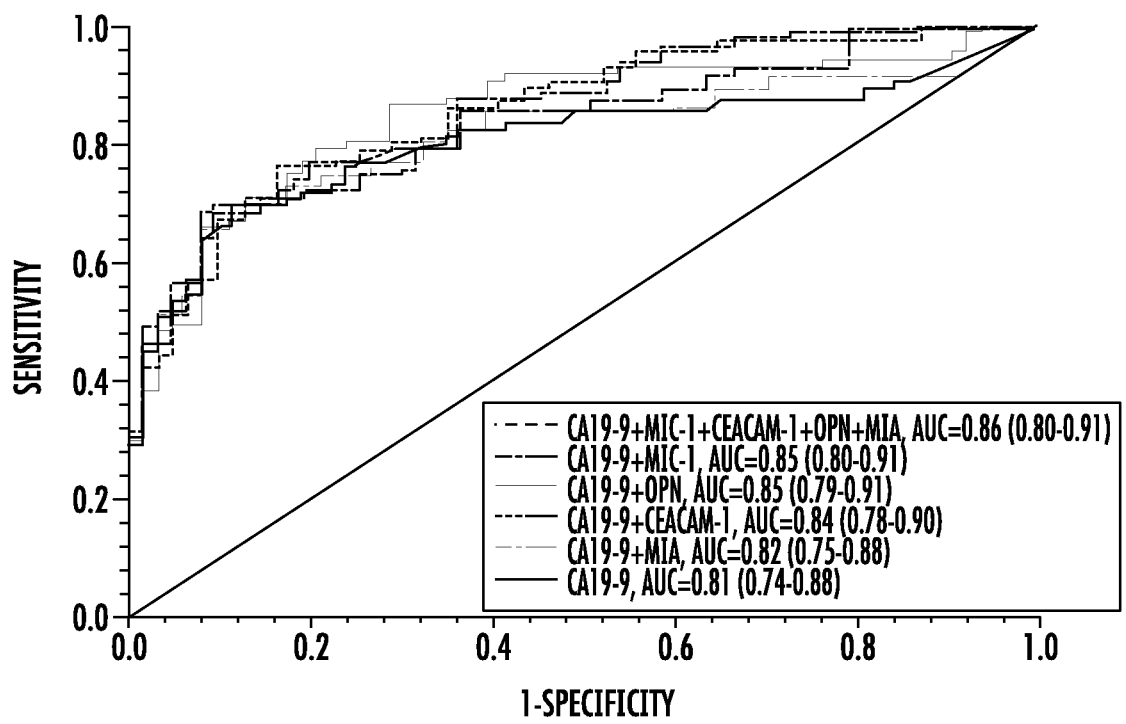
Figure 8A:
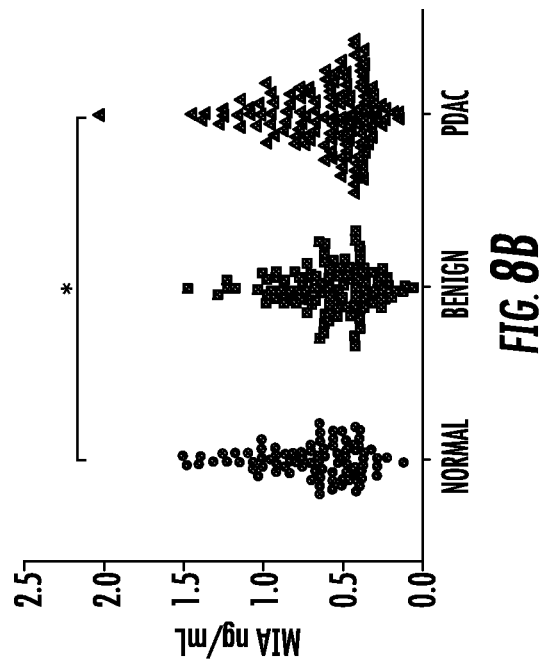
FIGS. 8A-8G. Scatter plots of 7 serum biomarker levels in all samples. A-F, there were significant differences of OPN, MIA, CEACAM-1, MIC-1, SPON1 & CA19-9 serum levels between normal and PDAC (all $p<0.0001$, except MIA at $p=0.043$). There were also significant differences of OPN, CEACAM-1, MIC-1 & CA19-9 serum levels between benign and PDAC (all $p<0.0001$, except OPN at $p=0.021$). Mann-Whitney U test was used for the comparisons. Bars indicate median value. *, $p<0.05$; , $p<0.01$; *, $p<0.001$; ****, $p<0.0001$.
Figure 8B:
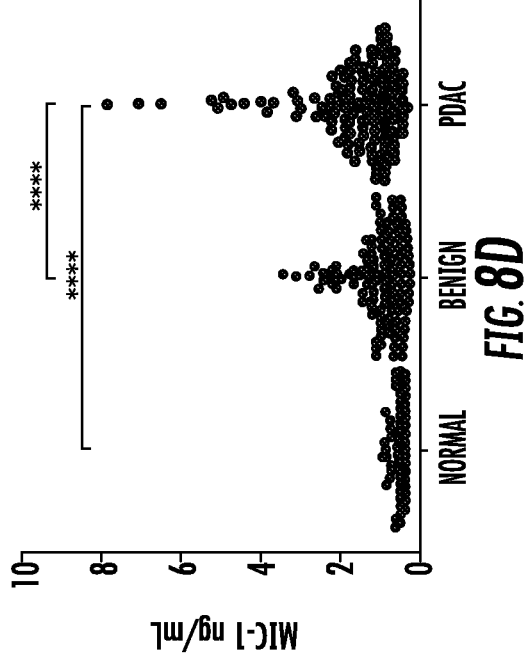
Figure 8C:
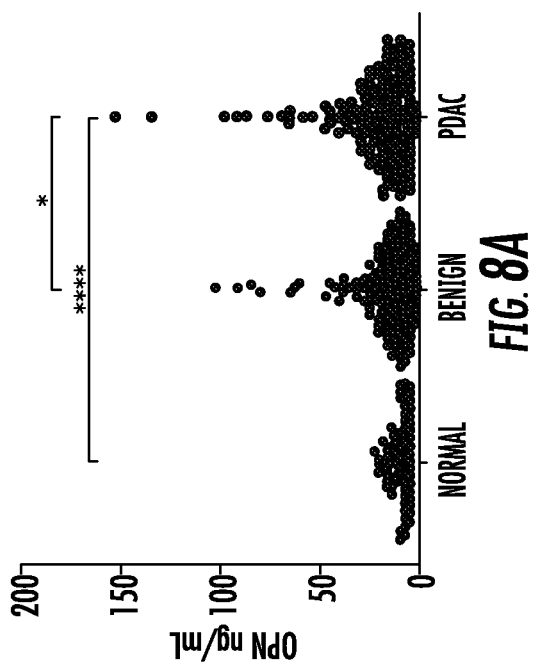
Figure 8D:
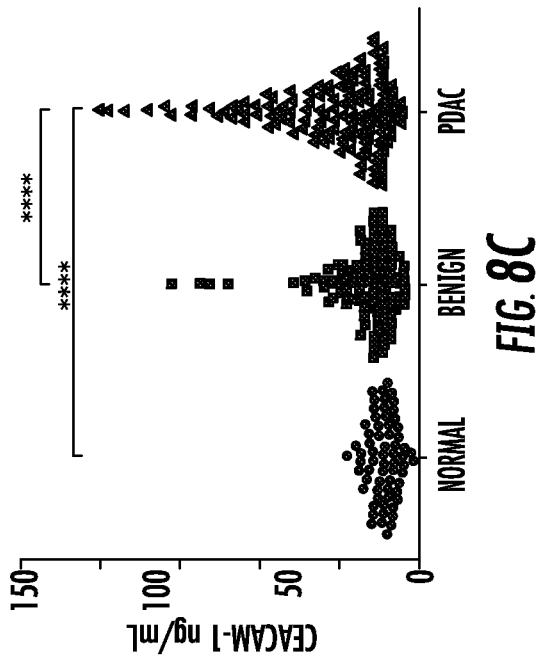
Figure 8E:
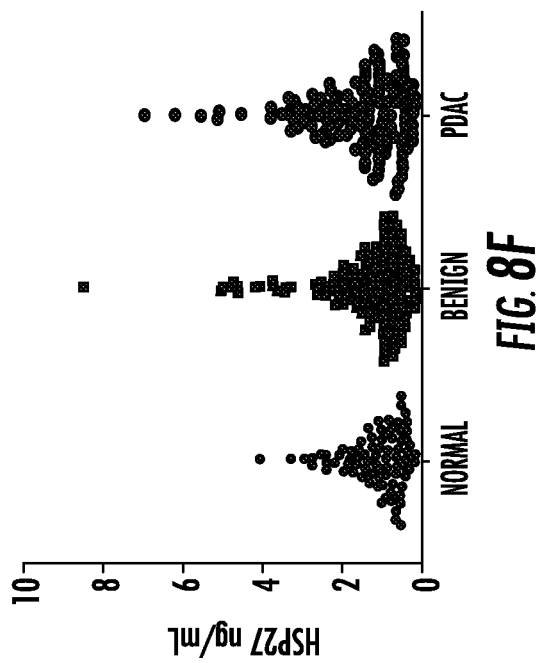
Figure 8G:
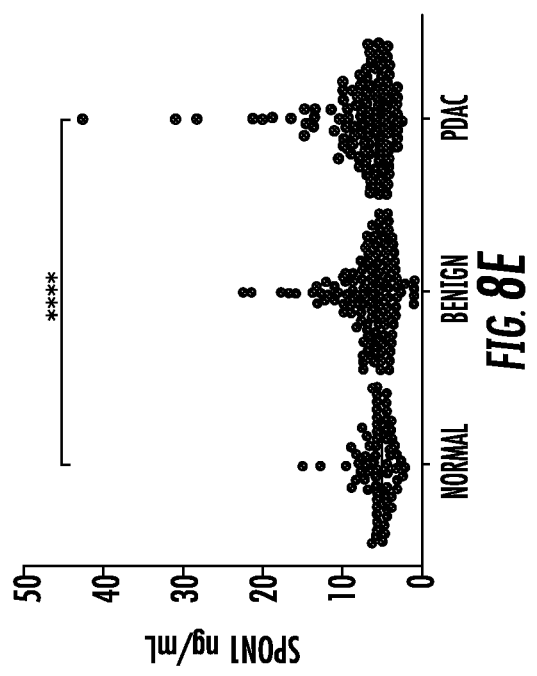
Figure 8F:
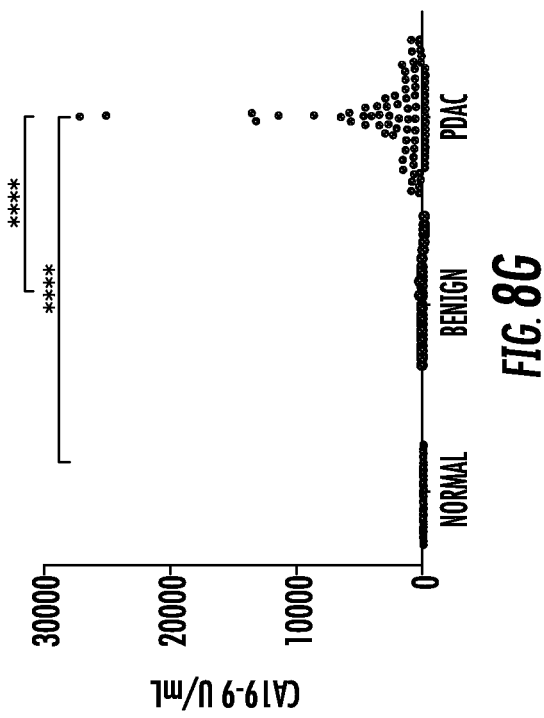

A 6-plex immunoassay of OPN, MIA, CEACAM-1, MIC-1, SPON1, and HSP27 was in-house developed with negligible cross-reactivity, recovery of 89-101%, and intra-assay or inter-assay precision of 3.5-11.6% or 6.1-17.3% for calibrators, respectively (Table 6). LOD or LLOQ was 0.053 ng/mL or 0.156 ng/mL (OPN), 0.054 ng/mL or 0.141 ng/mL (CEACAM-1), 0.002 ng/mL or 0.012 ng/mL (MIC-1), 0.002 ng/mL or 0.007 ng/mL (MIA), 0.011 ng/mL or 0.058 ng/mL (SPON1), and 0.004 ng/mL or 0.012 ng/mL (HSP27) (Table 3). The 6-plex assay demonstrated wide dynamic ranges for the target measurements, and was significant correlated with their respective monoplex assays (p<0.05) and/or commercial ELISAs (p<0.01) (FIGS. 2A-2F; FIGS. 3A-3G). Individually, the best biomarkers (AUC in ROC analysis, 95% CI) to separate PDAC early stage from pancreatitis or IPMN based on the ROC analysis were CA19-9 (0.72, [0.62-0.83]), MIA (0.70, [0.59-0.81]), MIC-1 (0.66, [0.54-0.77]) & CEACAM-1 (0.59, [0.47-0.71]) or MIC-1 (0.78, [0.68-0.87]), CA19-9 (0.77, [0.67-0.87]), OPN (0.73, [0.62-0.83]) & CEACAM-1 (0.66, [0.55-0.77]), respectively (FIGS. 4A and 4C). However, logistic regression modeling and ROC analysis selected a five-marker panel of CA19-9, CEACAM-1, MIC-1, SPON1 & MIA with an AUC=0.86 (0.79-0.94) for pancreatitis versus PDAC early stage or AUC=0.88 (0.81-0.95) for IPMN versus PDAC early stage, which significantly improved the individual biomarker performance (p value: 0.0094, 0.0003, 0.0018, 0.0001 & 0.0008 for pancreatitis versus PDAC early stage; and 0.0276, 0.0001, 0.0117, <0.0001 & <0.0001 for IPMN versus PDAC early stage; Delong test) (FIGS. 4B and 4D).

The multiplex immunoassay workflow provides sufficient analytical performance to evaluate serum biomarker panels that complement CA19-9 in early detection of pancreatic cancer. The biomarker panels identified in this study warrant further validation with a larger number of patient samples.

Patient Specimens

A total of 409 archived serum samples obtained from 189 patients with histologically diagnosed pancreatic ductal adenocarcinoma (PDAC) [mean (SD) age, 65 (10) years; M/F, 81/108] from January 2007 to October 2015, 131 patients with benign pancreatic conditions [57 (15) years; 71/60] from February 2007 to October 2015, and 89 healthy controls without a history of pancreatic diseases [35 (14) years; 45/44] from either April 2013 or August 2015 were collected at the Johns Hopkins Medical Institutions (JHMI) with institutional approval. Among 189 patients with PDAC, there are 97 early stage [IA/IB/IIA/IIB, 13/19/17/48; 65 (10) years; 34/63] and 92 late stage [III/IV, 19/73; 64 (10) years; 47/45] diseases. Among 131 patients with benign pancreatic conditions, there are 63 intraductal papillary mucinous neoplasm (IPMN) [64 (12) years; 24/39] and 68 chronic pancreatitis [51 (15) years; 47/21]. Detailed clinicopathologic characteristics of the study cohort, including diagnosis, age, sex and anatomic stage, were shown in Table 1. All serum samples were obtained before treatment and before surgery, and stored at −80° C. until analysis.

Reagents and Antibodies

All of the recombinant proteins and antibodies were purchased from R&D Systems (Minneapolis, MN)), except the detection antibody for SPON1 which was biotinylated in-house. Majority of the antibodies except those for OPN and SPON1 were from the DuoSet ELISA kits (R&D), which have been commercially tested as an appropriate pair of antibodies for the development of sandwich ELISAs to measure natural and recombinant human proteins in cell culture supernatants. Antibodies of OPN and SPON1 were also compatible for the ELISA applications. Detailed information for the recombinant proteins and antibodies are shown in Table 4. Magnetic COOH beads, amine coupling kits, and Bio-Plex Pro Reagent kits were purchased from Bio-Rad Laboratories (Hercules, CA). NHS and Sulfo-NHS, EDC, EZ-Link™ Sulfo-NHS-Biotin, and Zeba™ Spin Desalting Columns were purchased from Thermo Scientific (Rockford, IL). Human serum CA19-9 level was measured using a commercial kit from Tosoh Bioscience LLC (King of Prussia, PA). The human osteopontin ELISA kit (ABIN414433) and human heat shock protein 27 ELISA kit (ab 113334) were purchased from Antibodies-Online (Atlanta, GA) or Abcam (Cambridge, MA), respectively.

Conjugation of Antibodies to Microspheres

The capture antibodies for OPN, MIA, CEACAM-1, MIC-1, SPON1 and HSP27 were respectively coupled to magnetic beads of different regions using the Bio-Rad amine coupling kit according to the manufacturer's instructions. The use of differentially detectable beads of the different regions enables the simultaneous identification and quantification of multiple analytes in the same sample and the individual immunoassays therefore could be multiplexed. The optimal amounts of capture antibodies for one coupling reaction were used at either 6 μg for OPN, MIA, CEACAM-1, MIC-1 and HSP27 or 9 μg for SPON1, after the titration. The coupled beads were counted using a Coulter Z2 counter, validated using biotinylated rabbit anti-mouse (B8520) or rabbit anti-goat (B7014) IgG antibodies (Sigma-Aldrich, St. Louis, MO), and stored in storage buffer at 4° C. in the dark.

Multiplex Immunoassay

The magnetic bead-based multiplex immunoassay was developed for the selected candidate serum biomarkers using a Bio-Plex 200 suspension array system (Bio-Rad, Hercules, CA). The general workflow of multiplex immunoassay is shown in FIG. 1. The monoplex immunoassays of individual candidates were first developed using the Bio-Plex Pro Reagent kit. Briefly, 2500 coupled beads were incubated with 50 μl of a sample diluted in sample diluent for 1 hour. The beads were washed and incubated with 25 μl of the detection antibody diluted in the detection antibody diluent for 30 minutes. The beads were then washed again and incubated with 50 μl of 2 μg/mL streptavidin-phycoerytherin (SA-PE) diluted in the assay buffer for 10 minutes. The beads were finally washed and suspended in 125 μl of the assay buffer for the analysis by the Bio-Plex 200 system. All assays were carried out at room temperature and protected from light. All washing steps were performed with the washing buffer with an automated plate washer (Bio-Plex Prom II wash station, Bio-Rad). The calibration curves were established using 9 calibrators in 2-fold dilution series and used to determine the protein concentrations. Two pooled normal human sera (one from JHMI Biomarker Reference laboratory of the National Cancer Institute's Early Detection Research Network and the other S7023 from Sigma-Aldrich) were used for the optimization of the assay conditions.

Before multiplexing the individual assays, assay specificity was examined by performing single-detection and multiplexed-detection antibody cross-reactivity studies to detect the fluorescence signals in response to high concentrations of the recombinant proteins at the first dilution point of the standard curve (except SPON1 at the third dilution). The single detection antibody study was conducted by testing an individual detection antibody in the presence of multiplexed capture beads and a single antigen, which evaluates the specificity of a capture antibody. The multiplexed-detection antibody study was conducted by testing multiplexed detection antibodys in the presence of multiplexed capture beads and a single antigen, which evaluates the specificity of a detection antibody and to some degree the specificity of the capture antibody. Cross-reactivity was defined as the percentage of nonspecific cross-reacting signal detected relative to the specific signal for that analyte.

For the multiplex immunoassay, the capture beads and the detection antibodies were prepared by mixing the 2500 coupled beads and the detection antibodies used in the monoplex assays. The final concentrations of the detection antibodies in the multiplex assay were used at 0.4 μg/mL for OPN and CEACAM-1 or 2 μg/mL for SPON1 or 0.2 μg/mL for MIA and HSP27 or 0.0125 μg/mL for MIC-1, respectively, after the titration. The calibration curve was established using 9 calibrators in 2-fold dilution series derived from a mixture of the highest standard points of 7 recombinant proteins. The highest standards of 7 recombinant proteins in the multiplex assay were used at 40, 1.5, 20, 3, 15 and 3 ng/mL for OPN, MIA, CEACAM-1, MIC-1, SPON1 and HSP27, respectively. To assess the correlations of the developed immunoassays in protein quantifications, the multiplex immunoassays were compared to the monoplex immunoassays by measuring 4 dilutions of individual recombinant proteins based on their respective calibration curves. The correlations of the developed multiplex immunoassays and commercial ELISA kits in serum OPN or HSP27 protein quantifications were also determined in 7 or 13 patient sera, respectively. The multiplex immunoassay was carried out using the Bio-Plex Pro Reagent kit in the same procedures as those in the monoplex assays described above. The serum samples were 4-fold diluted in the sample diluent in the multiplex immunoassay. Two quality controls (QC) were prepared by diluting the mixture of the highest standards of 6 recombinant proteins at either 3-fold (QC1) or 30-fold (QC2). Two pooled human sera with the known CA19-9 measurements at either high or low levels were used as the calibrators. The multiplex immunoassay was performed in duplicate on 13×96-well Bio-Plex flat bottom plates with a calibration curve, 2 doses of QCs and 2 doses of calibrators in each plate. All samples were randomized with regard to their plate locations.

Data acquisition and primary data analysis were performed on the Bio-Plex 200 system in combination with Bio-Plex Manager Software version 6.1.1 by use of a 5-parametric (5-PL) nonlinear logistic regression curve fitting model (Bio-Rad). According to Bio-Rad Bio-Plex multiplex immunoassay handout (bio-rad.com/en-us/applications-technologies/bio-plex-multiplex-immunoassays), in this study, the assay sensitivity (limit of black, LOB) was defined as the concentration of analyte corresponding to the median fluorescent intensity (MFI) of the background plus two standard deviations (SD) of the mean background MFI. The assay reproducibility was assessed in both intra- and inter-assay precisions. Intra-assay precision was calculated as the coefficient of variance (% CV) on the duplicates of two QCs or two calibrators on a single assay plate. Inter-assay precision was calculated as the % CV from 6 independent assays. The assay accuracy (recovery percentage) was calculated as the percentage of the observed concentration relative to the expected concentration of each standard point or QC. The assay working dynamic range was defined as the range between the lower limit of quantification (LLOQ) and the upper limit of quantification (ULOQ) in which an assay is both precise (intra-assay % CV≤10% and inter-assay % CV 15%) and accurate (80-120% recovery).

Data Analysis

The nonparametric Mann-Whitney U test was used to compare serum biomarker levels between PDAC patients, benign pancreatic conditions and healthy controls, with a p-value less than 0.05 considered significant. Receiver operator characteristic (ROC) analysis was performed and the area under the curve (AUC) was calculated separately for each of 7 biomarkers and the combinations of biomarkers. Delong test was used to compare the AUCs. Pearson correlation coefficients were determined to assess correlation of the measurements between the multiplex and monoplex immunoassays or commercial ELISA kits. Logistic regression analysis (both backward stepwise and forward stepwise) was performed to select the panels of biomarkers with the highest performance. The Statistica 12 (StatSoft) and GraphPad Prism 6 (GraphPa Software) were used for statistical analysis.

TABLE 1

Clinicopathologic characteristics of the study cohort.

| Variables | Number (%) |
|---|---|
| Total | 409 |
| Healthy control | 89 (21.8) |
| Age (year) | |
| Mean ± SD | 35 ± 14 |
| Range | 21-67 |

TABLE 1-continued

Clinicopathologic characteristics of the study cohort.

| Variables | Number (%) |
|---|---|
| Gender | |
| Male | 45 (50.6) |
| Female | 44 (49.4) |
| Benign conditions | 131 (32) |
| Age (year) | |
| Mean ± SD | 57 ± 15 |
| Range | 13-89 |
| Gender | |
| Male | 71 (54.2) |
| Female | 60 (45.8) |

TABLE 2

Assay specificity of the 6-plex immunoassay. Percentage of cross-reactivity (single-detection/multiplexed-detection antibody) was calculated based on fluorescence signals detected in response to high concentrations of the recombinant proteins at the $1^{st}$ dilution point (at $3^{rd}$ for SPON1) of the standard curve in single-detection and multiplexed-detection antibody cross-reactivity studies (both with multiplexed beads and single antigen).

| Target | OPN | MIA | CEACAM-1 | MIC-1 | SPON1 | HSP27 |
|---|---|---|---|---|---|---|
| OPN | | 0.0/0.0 | 0.0/0.0 | 0.0/0.0 | 0.0/0.0 | 0.0/0.0 |
| MIA | 0.3/0.1 | | 0.4/0.0 | 0.1/0.1 | 0.3/0.0 | 0.1/0.1 |
| CEACAM-1 | 0.0/0.3 | 0.2/0.0 | | 0.0/0.2 | 0.0/0.0 | 0.0/0.0 |
| MIC-1 | 0.0/0.0 | 0.0/0.0 | 0.0/0.0 | | 0.0/0.0 | 0.0/0.0 |
| SPON1 | 2.4/2.1 | 1.7/1.3 | 2.0/2.0 | 2.7/2.4 | | 3.3/3.3 |
| HSP27 | 0.1/0.1 | 0.2/0.1 | 0.2/0.1 | 0.2/0.1 | 0.7/0.7 | |

TABLE 3

Analytical performance of the 6-plex immunoassay. QC1, high control. QC2, low control. LOD, limit of detection. LLOQ, lower limit of quantitation. ULOQ, upper limit of quantification. The correlation of 6-plex vs monoplex was examined on 4 doses of individual recombinant proteins. The correlation of 6-plex vs the commercial ELISA kit was examined on 7 (OPN) or 13 (HSP27) patient sera.

| | Mean (pg/mL) | | Intra-assay Precision (% CV) | | Inter-assay Precision (% CV) | | LOD (pg/mL) | LLOQ (pg/mL) | ULOQ (pg/mL) | Replicates* (% CV) | 6-plex vs Monoplex, Pearson R/p value | 6-plex vs ELISA, Pearson R/p value |
|---|---|---|---|---|---|---|---|---|---|---|---|---|
| | QC1 | QC2 | QC1 | QC2 | QC1 | QC2 | | | | | | |
| OPN | 13448.3 | 1228.3 | 2.1 | 5.1 | 3.7 | 4.2 | 52.5 | 155.7 | 34728.7 | 3.4 | 0.9987/0.0013 | 0.8945/0.0066 |
| MIA | 481.7 | 48.3 | 8.6 | 10.0 | 4.4 | 8.4 | 2.3 | 6.7 | 1541.1 | 9.2 | 0.9888/0.0112 | ND** |
| CEACAM-1 | 6141.7 | 658.3 | 9.3 | 6.6 | 8.6 | 16.3 | 53.7 | 140.7 | 20118.4 | 7.5 | 0.9715/0.0285 | ND |
| MIC-1 | 963.3 | 93.3 | 8.1 | 10.3 | 21.5 | 18.8 | 1.5 | 11.6 | 2327.0 | 5.1 | 0.9996/0.0004 | ND |
| SPON1 | 4746.7 | 473.3 | 4.3 | 2.7 | 5.0 | 6.8 | 10.7 | 58.1 | 15032.7 | 6.3 | 0.9675/0.0325 | ND |
| HSP27 | 933.3 | 88.3 | 15.4 | 12.6 | 14.5 | 13.2 | 4.4 | 11.7 | 3000.6 | 9.0 | 0.9997/0.0003 | 0.9254/<0.00001 |

*mean of % CV for replicates in all samples for each protein.
**ND, not determined.

TABLE 1-continued

Clinicopathologic characteristics of the study cohort.

| Variables | Number (%) |
|---|---|
| Chronic pancreatitis | 68 (51.9) |
| IPMN | 63 (48.1) |
| PDAC | 189 (46.2) |
| Age (year) | |
| Mean ± SD | 65 ± 10 |
| Range | 30-92 |
| Gender | |
| Male | 81 (42.9) |
| Female | 108 (57.1) |
| Early stage | 97 (51.3) |
| IA/IB/IIA/IIB | 13/19/17/48 |
| Late stage | 92 (48.7) |
| III/IV | 19/73 |

NOTE:
IPMN, intraductal papillary mucinous neoplasm.

TABLE 4

6-plex immunoassay recombinant proteins and antibodies.

| Target | Recombinant Protein Cat. # | Capture Antibody Cat. # | Capture Antibody Host | Detection Antibody Cat. # | Detection Antibody Host |
|---|---|---|---|---|---|
| OPN | 1433-OP-050 | MAB14332 | Mouse | BAF1433 | Goat |
| MIA | DY2050 | DY2050 | Mouse | DY2050 | Goat |
| CEACAM-1 | DY2244 | DY2244 | Mouse | DY2244 | Goat |
| MIC-1 | DY957 | DY957 | Mouse | DY957 | Goat |
| SPON1 | 3135-SP/CF | AF3135 | Goat | AF3135* | Goat |
| HSP27 | DY1580 | DY1580 | Goat | DY1580 | Rabbit |

NOTE:
*all of the recombinant proteins and antibodies were purchased from R&D Systems, except detection antibody of SPON1 was biotinylated in-house.

TABLE 5

Statistics of individual biomarkers in healthy controls, benign conditions and PDAC patients.
(NOTE: all biomarkers are at ng/ml, except CA19-9 at U/ml.

| Biomarker | Subgroup | Number | Min | Max | Median | Mean |
|---|---|---|---|---|---|---|
| OPN | Healthy Control | 89 | 2.14 | 21.66 | 6.88 | 7.93 |
| | Chronic Pancreatitis | 68 | 0.76 | 103.56 | 13.59 | 20.68 |

TABLE 5-continued

Statistics of individual biomarkers in healthy
controls, benign conditions and PDAC patients.
(NOTE: all biomarkers are at ng/ml, except CA19-9 at U/ml.

| Biomarker | Subgroup | Number | Min | Max | Median | Mean |
|---|---|---|---|---|---|---|
|  | IPMN | 63 | 2.28 | 84.75 | 8.51 | 12.05 |
|  | PDAC early stage | 97 | 2.03 | 135.26 | 14.19 | 18.99 |
|  | PDAC late stage | 92 | 2.31 | 154.05 | 14.53 | 21.48 |
| MIA | Healthy Control | 89 | 0.12 | 1.50 | 0.63 | 0.69 |
|  | Chronic Pancreatitis | 68 | 0.12 | 1.24 | 0.48 | 0.51 |
|  | IPMN | 62 | 0.05 | 1.48 | 0.62 | 0.64 |
|  | PDAC early stage | 97 | 0.14 | 1.40 | 0.51 | 0.59 |
|  | PDAC late stage | 92 | 0.24 | 2.05 | 0.58 | 0.66 |
| CEACAM-1 | Healthy Control | 89 | 2.33 | 26.86 | 12.66 | 13.01 |
|  | Chronic Pancreatitis | 68 | 5.15 | 93.21 | 16.83 | 22.88 |
|  | IPMN | 63 | 5.65 | 35.40 | 16.06 | 17.01 |
|  | PDAC early stage | 97 | 4.82 | 120.85 | 21.19 | 31.16 |
|  | PDAC late stage | 92 | 4.58 | 117.79 | 22.63 | 29.74 |
| MIC-1 | Healthy Control | 89 | 0.11 | 0.77 | 0.26 | 0.32 |
|  | Chronic Pancreatitis | 68 | 0.22 | 3.35 | 0.86 | 1.02 |
|  | IPMN | 63 | 0.25 | 3.01 | 0.69 | 0.83 |
|  | PDAC early stage | 96 | 0.35 | 7.93 | 1.14 | 1.51 |
|  | PDAC late stage | 92 | 0.20 | 7.05 | 1.01 | 1.30 |
| SPON1 | Healthy Control | 89 | 1.87 | 14.90 | 4.70 | 5.02 |
|  | Chronic Pancreatitis | 68 | 1.00 | 17.46 | 5.92 | 6.42 |
|  | IPMN | 63 | 0.60 | 21.82 | 5.15 | 5.87 |
|  | PDAC early stage | 97 | 1.95 | 42.76 | 5.81 | 7.24 |
|  | PDAC late stage | 92 | 2.09 | 21.14 | 5.85 | 6.46 |
| HSP27 | Healthy Control | 89 | 0.22 | 4.20 | 0.86 | 1.16 |
|  | Chronic Pancreatitis | 68 | 0.22 | 4.83 | 0.97 | 1.26 |
|  | IPMN | 63 | 0.10 | 8.62 | 0.90 | 1.34 |
|  | PDAC early stage | 97 | 0.15 | 7.10 | 1.20 | 1.51 |
|  | PDAC late stage | 92 | 0.15 | 5.22 | 1.13 | 1.33 |
| CA19-9 | Healthy Control | 89 | 1.00 | 71.60 | 11.00 | 15.55 |
|  | Chronic Pancreatitis | 68 | 1.00 | 203.20 | 20.10 | 32.24 |
|  | IPMN | 63 | 1.00 | 386.90 | 16.80 | 26.85 |
|  | PDAC early stage | 97 | 1.00 | 27027.80 | 90.60 | 824.71 |
|  | PDAC late stage | 92 | 1.00 | 25110.70 | 354.75 | 1638.68 |

TABLE 6

Assay specificity of the 6-plex immunoassay. Percentage of cross-reactivity (single-detection/multiplexed-detection antibody) was calculated based on fluorescence signals detected in response to high concentrations of the recombinant proteins at the $1^{st}$ dilution point (except SPON1 at $3^{rd}$ because only 1.4% of sera with SPON1 exceed STD3) of the standard curve in single-detection and multiplexed-detection antibody cross-reactivity studies (both with multiplexed beads and single antigen).

| Target | OPN | MIA | CEACAM-1 | MIC-1 | SPON1 | HSP27 |
|---|---|---|---|---|---|---|
| OPN |  | 0.0/0.0 | 0.0/0.0 | 0.0/0.0 | 0.0/0.0 | 0.0/0.0 |
| MIA | 0.3/0.1 |  | 0.4/0.0 | 0.1/0.1 | 0.3/0.0 | 0.1/0.1 |
| CEACAM-1 | 0.0/0.3 | 0.2/0.0 |  | 0.0/0.2 | 0.0/0.0 | 0.0/0.0 |
| MIC-1 | 0.0/0.0 | 0.0/0.0 | 0.0/0.0 |  | 0.0/0.0 | 0.0/0.0 |
| SPON1 | 2.4/2.1 | 1.7/1.3 | 2.0/2.0 | 2.7/2.4 |  | 3.3/3.3 |
| HSP27 | 0.1/0.1 | 0.2/0.1 | 0.2/0.1 | 0.2/0.1 | 0.7/0.7 |  |

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of diagnosing and treating a subject having pancreatic ductal adenocarcinoma (PDAC), the method comprising:
   (a) detecting in a blood or serum sample from a subject, having an increased level of CA19-9 polysaccharide relative to a healthy subject, increased levels relative to a healthy subject of markers of HSP27, CEMAM-1, OPN, MIA and MIC-1, and
   (b) determining the subject has pancreatic ductal adenocarcinoma (PDAC) based on the increased levels of the markers; and
   (c) administering a therapeutically effective chemotherapeutic agent to the subject determined to have pancreatic ductal adenocarcinoma (PDAC).

2. The method of claim 1, wherein the levels of polysaccharide or markers are measured using a bead based immunoassay or an ELISA.

3. The method of claim 1, consisting essentially of:
   (a) detecting in a blood or serum sample from the subject having an increased level of CAI 9-9 polysaccharide relative to a healthy subject, increased levels relative to a healthy subject of markers of HSP27, CEMAM-1, OPN, MIA, and MIC-1,
   (b) determining the subject has pancreatic ductal adenocarcinoma (PDAC) based on the increased levels of the markers; and
   (c) administering a therapeutically effective chemotherapeutic agent to the subject determined to have pancreatic ductal adenocarcinoma (PDAC).

4. The method of claim 1 consisting of:
   (a) detecting in a blood or serum sample from the subject having an increased level of CAI 9-9 polysaccharide relative to a healthy subject, increased levels relative to a healthy subject of markers of HSP27, CEMAM-1, OPN, MIA, and MIC-1,
   (b) determining the subject has pancreatic ductal adenocarcinoma (PDAC) based on the increased levels of the markers; and
   (c) administering a therapeutically effective chemotherapeutic agent to the subject determined to have pancreatic ductal adenocarcinoma (PDAC).

* * * * *

SEQUENCE LISTING

<160> NUMBER OF SEQ ID NOS: 16

<210> SEQ ID NO 1
<211> LENGTH: 468
<212> TYPE: PRT
<213> ORGANISM: Homo sapiens

<400> SEQUENCE: 1

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
            85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
        435                 440                 445

Ala Cys Phe Leu His Phe Gly Lys Thr Gly Arg Thr Thr Pro Met Thr
    450                 455                 460

His Leu Thr Arg
465

<210> SEQ ID NO 2
<211> LENGTH: 205
<212> TYPE: PRT
<213> ORGANISM: Homo sapiens -continued

```
<400> SEQUENCE: 2

Met Thr Glu Arg Arg Val Pro Phe Ser Leu Leu Arg Gly Pro Ser Trp
1               5                   10                  15

Asp Pro Phe Arg Asp Trp Tyr Pro His Ser Arg Leu Phe Asp Gln Ala
            20                  25                  30

Phe Gly Leu Pro Arg Leu Pro Glu Glu Trp Ser Gln Trp Leu Gly Gly
        35                  40                  45

Ser Ser Trp Pro Gly Tyr Val Arg Pro Leu Pro Pro Ala Ala Ile Glu
50                  55                  60

Ser Pro Ala Val Ala Ala Pro Ala Tyr Ser Arg Ala Leu Ser Arg Gln
65                  70                  75                  80

Leu Ser Ser Gly Val Ser Glu Ile Arg His Thr Ala Asp Arg Trp Arg
                85                  90                  95

Val Ser Leu Asp Val Asn His Phe Ala Pro Asp Glu Leu Thr Val Lys
            100                 105                 110

Thr Lys Asp Gly Val Val Glu Ile Thr Gly Lys His Glu Glu Arg Gln
        115                 120                 125

Asp Glu His Gly Tyr Ile Ser Arg Cys Phe Thr Arg Lys Tyr Thr Leu
    130                 135                 140

Pro Pro Gly Val Asp Pro Thr Gln Val Ser Ser Ser Leu Ser Pro Glu
145                 150                 155                 160

Gly Thr Leu Thr Val Glu Ala Pro Met Pro Lys Leu Ala Thr Gln Ser
                165                 170                 175

Asn Glu Ile Thr Ile Pro Val Thr Phe Glu Ser Arg Ala Gln Leu Gly
            180                 185                 190

Gly Pro Glu Ala Ala Lys Ser Asp Glu Thr Ala Ala Lys
        195                 200                 205

<210> SEQ ID NO 3
<211> LENGTH: 585
<212> TYPE: PRT
<213> ORGANISM: Homo sapiens

<400> SEQUENCE: 3

Met Thr Pro Pro Arg Leu Phe Trp Val Trp Leu Leu Val Ala Gly Thr
1               5                   10                  15

Gln Gly Val Asn Asp Gly Asp Met Arg Leu Ala Asp Gly Gly Ala Thr
            20                  25                  30

Asn Gln Gly Arg Val Glu Ile Phe Tyr Arg Gly Gln Trp Gly Thr Val
        35                  40                  45

Cys Asp Asn Leu Trp Asp Leu Thr Asp Ala Ser Val Val Cys Arg Ala
50                  55                  60

Leu Gly Phe Glu Asn Ala Thr Gln Ala Leu Gly Arg Ala Ala Phe Gly
65                  70                  75                  80

Gln Gly Ser Gly Pro Ile Met Leu Asp Glu Val Gln Cys Thr Gly Thr
                85                  90                  95

Glu Ala Ser Leu Ala Asp Cys Lys Ser Leu Gly Trp Leu Lys Ser Asn
            100                 105                 110

Cys Arg His Glu Arg Asp Ala Gly Val Val Cys Thr Asn Glu Thr Arg
        115                 120                 125

Ser Thr His Thr Leu Asp Leu Ser Arg Glu Leu Ser Glu Ala Leu Gly
    130                 135                 140

Gln Ile Phe Asp Ser Gln Arg Gly Cys Asp Leu Ser Ile Ser Val Asn
145                 150                 155                 160
```

-continued

Val Gln Gly Glu Asp Ala Leu Gly Phe Cys Gly His Thr Val Ile Leu
            165                 170                 175

Thr Ala Asn Leu Glu Ala Gln Ala Leu Trp Lys Glu Pro Gly Ser Asn
        180                 185                 190

Val Thr Met Ser Val Asp Ala Glu Cys Val Pro Met Val Arg Asp Leu
    195                 200                 205

Leu Arg Tyr Phe Tyr Ser Arg Arg Ile Asp Ile Thr Leu Ser Ser Val
210                 215                 220

Lys Cys Phe His Lys Leu Ala Ser Ala Tyr Gly Ala Arg Gln Leu Gln
225                 230                 235                 240

Gly Tyr Cys Ala Ser Leu Phe Ala Ile Leu Leu Pro Gln Asp Pro Ser
            245                 250                 255

Phe Gln Met Pro Leu Asp Leu Tyr Ala Tyr Ala Val Ala Thr Gly Asp
        260                 265                 270

Ala Leu Leu Glu Lys Leu Cys Leu Gln Phe Leu Ala Trp Asn Phe Glu
    275                 280                 285

Ala Leu Thr Gln Ala Glu Ala Trp Pro Ser Val Pro Thr Asp Leu Leu
        290                 295                 300

Gln Leu Leu Leu Pro Arg Ser Asp Leu Ala Val Pro Ser Glu Leu Ala
305                 310                 315                 320

Leu Leu Lys Ala Val Asp Thr Trp Ser Trp Gly Glu Arg Ala Ser His
            325                 330                 335

Glu Glu Val Glu Gly Leu Val Glu Lys Ile Arg Phe Pro Met Met Leu
        340                 345                 350

Pro Glu Glu Leu Phe Glu Leu Gln Phe Asn Leu Ser Leu Tyr Trp Ser
    355                 360                 365

His Glu Ala Leu Phe Gln Lys Lys Thr Leu Gln Ala Leu Glu Phe His
        370                 375                 380

Thr Val Pro Phe Gln Leu Leu Ala Arg Tyr Lys Gly Leu Asn Leu Thr
385                 390                 395                 400

Glu Asp Thr Tyr Lys Pro Arg Ile Tyr Thr Ser Pro Thr Trp Ser Ala
            405                 410                 415

Phe Val Thr Asp Ser Ser Trp Ser Ala Arg Lys Ser Gln Leu Val Tyr
        420                 425                 430

Gln Ser Arg Arg Gly Pro Leu Val Lys Tyr Ser Ser Asp Tyr Phe Gln
    435                 440                 445

Ala Pro Ser Asp Tyr Arg Tyr Tyr Pro Tyr Gln Ser Phe Gln Thr Pro
        450                 455                 460

Gln His Pro Ser Phe Leu Phe Gln Asp Lys Arg Val Ser Trp Ser Leu
465                 470                 475                 480

Val Tyr Leu Pro Thr Ile Gln Ser Cys Trp Asn Tyr Gly Phe Ser Cys
            485                 490                 495

Ser Ser Asp Glu Leu Pro Val Leu Gly Leu Thr Lys Ser Gly Gly Ser
        500                 505                 510

Asp Arg Thr Ile Ala Tyr Glu Asn Lys Ala Leu Met Leu Cys Glu Gly
    515                 520                 525

Leu Phe Val Ala Asp Val Thr Asp Phe Glu Gly Trp Lys Ala Ala Ile
        530                 535                 540

Pro Ser Ala Leu Asp Thr Asn Ser Ser Lys Ser Thr Ser Ser Phe Pro
545                 550                 555                 560

Cys Pro Ala Gly His Phe Asn Gly Phe Arg Thr Val Ile Arg Pro Phe
            565                 570                 575

Tyr Leu Thr Asn Ser Ser Gly Val Asp

```
            580             585
```

<210> SEQ ID NO 4
<211> LENGTH: 131
<212> TYPE: PRT
<213> ORGANISM: Homo sapiens

<400> SEQUENCE: 4

```
Met Ala Arg Ser Leu Val Cys Leu Gly Val Ile Ile Leu Leu Ser Ala
1               5                   10                  15

Phe Ser Gly Pro Gly Val Arg Gly Gly Pro Met Pro Lys Leu Ala Asp
            20                  25                  30

Arg Lys Leu Cys Ala Asp Gln Glu Cys Ser His Pro Ile Ser Met Ala
        35                  40                  45

Val Ala Leu Gln Asp Tyr Met Ala Pro Asp Cys Arg Phe Leu Thr Ile
    50                  55                  60

His Arg Gly Gln Val Val Tyr Val Phe Ser Lys Leu Lys Gly Arg Gly
65                  70                  75                  80

Arg Leu Phe Trp Gly Gly Ser Val Gln Gly Asp Tyr Tyr Gly Asp Leu
                85                  90                  95

Ala Ala Arg Leu Gly Tyr Phe Pro Ser Ser Ile Val Arg Glu Asp Gln
            100                 105                 110

Thr Leu Lys Pro Gly Lys Val Asp Val Lys Thr Asp Lys Trp Asp Phe
        115                 120                 125

Tyr Cys Gln
        130
```

<210> SEQ ID NO 5
<211> LENGTH: 308
<212> TYPE: PRT
<213> ORGANISM: Homo sapiens

<400> SEQUENCE: 5

```
Met Pro Gly Gln Glu Leu Arg Thr Leu Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Thr
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
```

```
            180                 185                 190
Arg Arg Ala Arg Ala Arg Asn Gly Asp His Cys Pro Leu Gly Pro Gly
            195                 200                 205

Arg Cys Cys Arg Leu His Thr Val Arg Ala Ser Leu Glu Asp Leu Gly
        210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
            290                 295                 300

Cys His Cys Ile
305

<210> SEQ ID NO 6
<211> LENGTH: 287
<212> TYPE: PRT
<213> ORGANISM: Homo sapiens

<400> SEQUENCE: 6

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Asn
            20                  25                  30

Ala Val Ser Ser Glu Glu Thr Asn Asp Phe Lys Gln Glu Thr Leu Pro
        35                  40                  45

Ser Lys Ser Asn Glu Ser His Asp His Met Asp Asp Met Asp Asp Glu
    50                  55                  60

Asp Asp Asp Asp His Val Asp Ser Gln Asp Ser Ile Asp Ser Asn Asp
65                  70                  75                  80

Ser Asp Asp Val Asp Asp Thr Asp Ser His Gln Ser Asp Glu Ser
                85                  90                  95

His His Ser Asp Glu Ser Asp Glu Leu Val Thr Asp Phe Pro Thr Asp
            100                 105                 110

Leu Pro Ala Thr Glu Val Phe Thr Pro Val Val Pro Thr Val Asp Thr
        115                 120                 125

Tyr Asp Gly Arg Gly Asp Ser Val Val Tyr Gly Leu Arg Ser Lys Ser
    130                 135                 140

Lys Lys Phe Arg Arg Pro Asp Ile Gln Tyr Pro Asp Ala Thr Asp Glu
145                 150                 155                 160

Asp Ile Thr Ser His Met Glu Ser Glu Glu Leu Asn Gly Ala Tyr Lys
                165                 170                 175

Ala Ile Pro Val Ala Gln Asp Leu Asn Ala Pro Ser Asp Trp Asp Ser
            180                 185                 190

Arg Gly Lys Asp Ser Tyr Glu Thr Ser Gln Leu Asp Asp Gln Ser Ala
        195                 200                 205

Glu Thr His Ser His Lys Gln Ser Arg Leu Tyr Lys Arg Lys Ala Asn
    210                 215                 220

Asp Glu Ser Asn Glu His Ser Asp Val Ile Asp Ser Gln Glu Leu Ser
225                 230                 235                 240
```

```
Lys Val Ser Arg Glu Phe His Ser His Glu Phe His Ser His Glu Asp
            245                 250                 255
Met Leu Val Val Asp Pro Lys Ser Lys Glu Glu Asp Lys His Leu Lys
        260                 265                 270
Phe Arg Ile Ser His Glu Leu Asp Ser Ala Ser Ser Glu Val Asn
    275                 280                 285
```

<210> SEQ ID NO 7
<211> LENGTH: 779
<212> TYPE: PRT
<213> ORGANISM: Homo sapiens

<400> SEQUENCE: 7

```
Met Ile Pro Phe Leu Pro Met Phe Ser Leu Leu Leu Leu Leu Ile Val
1               5                   10                  15
Asn Pro Ile Asn Ala Asn Asn His Tyr Asp Lys Ile Leu Ala His Ser
            20                  25                  30
Arg Ile Arg Gly Arg Asp Gln Gly Pro Asn Val Cys Ala Leu Gln Gln
        35                  40                  45
Ile Leu Gly Thr Lys Lys Lys Tyr Phe Ser Thr Cys Lys Asn Trp Tyr
    50                  55                  60
Lys Lys Ser Ile Cys Gly Gln Lys Thr Thr Val Leu Tyr Glu Cys Cys
65                  70                  75                  80
Pro Gly Tyr Met Arg Met Glu Gly Met Lys Gly Cys Pro Ala Val Leu
                85                  90                  95
Pro Ile Asp His Val Tyr Gly Thr Leu Gly Ile Val Gly Ala Thr Thr
            100                 105                 110
Thr Gln Arg Tyr Ser Asp Ala Ser Lys Leu Arg Glu Glu Ile Glu Gly
        115                 120                 125
Lys Gly Ser Phe Thr Tyr Phe Ala Pro Ser Asn Glu Ala Trp Asp Asn
    130                 135                 140
Leu Asp Ser Asp Ile Arg Arg Gly Leu Glu Ser Asn Val Asn Val Glu
145                 150                 155                 160
Leu Leu Asn Ala Leu His Ser His Met Ile Asn Lys Arg Met Leu Thr
                165                 170                 175
Lys Asp Leu Lys Asn Gly Met Ile Ile Pro Ser Met Tyr Asn Asn Leu
            180                 185                 190
Gly Leu Phe Ile Asn His Tyr Pro Asn Gly Val Val Thr Val Asn Cys
        195                 200                 205
Ala Arg Ile Ile His Gly Asn Gln Ile Ala Thr Asn Gly Val Val His
    210                 215                 220
Val Ile Asp Arg Val Leu Thr Gln Ile Gly Thr Ser Ile Gln Asp Phe
225                 230                 235                 240
Ile Glu Ala Glu Asp Asp Leu Ser Ser Phe Arg Ala Ala Ala Ile Thr
                245                 250                 255
Ser Asp Ile Leu Glu Ala Leu Gly Arg Asp Gly His Phe Thr Leu Phe
            260                 265                 270
Ala Pro Thr Asn Glu Ala Phe Glu Lys Leu Pro Arg Gly Val Leu Glu
        275                 280                 285
Arg Ile Met Gly Asp Lys Val Ala Ser Glu Ala Leu Met Lys Tyr His
    290                 295                 300
Ile Leu Asn Thr Leu Gln Cys Ser Glu Ser Ile Met Gly Gly Ala Val
305                 310                 315                 320
Phe Glu Thr Leu Glu Gly Asn Thr Ile Glu Ile Gly Cys Asp Gly Asp
                325                 330                 335
```

-continued

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
            355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
            405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
            485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
    515                 520                 525

Gly Asp Trp Thr Leu Phe Val Pro Thr Asn Asp Ala Phe Lys Gly Met
530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
            565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
    595                 600                 605

Ser Lys Glu Ser Asp Ile Met Thr Thr Asn Gly Val Ile His Val Val
610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
            645                 650                 655

Arg Gly Ser Thr Phe Lys Glu Ile Pro Val Thr Val Tyr Lys Pro Ile
            660                 665                 670

Ile Lys Lys Tyr Thr Lys Ile Ile Asp Gly Val Pro Val Glu Ile Thr
    675                 680                 685

Glu Lys Glu Thr Arg Glu Glu Arg Ile Ile Thr Gly Pro Glu Ile Lys
            690                 695                 700

Tyr Thr Arg Ile Ser Thr Gly Gly Glu Thr Glu Thr Leu Lys
705                 710                 715                 720

Lys Leu Leu Gln Glu Glu Val Thr Lys Val Thr Lys Phe Ile Glu Gly
            725                 730                 735

Gly Asp Gly His Leu Phe Glu Asp Glu Glu Ile Lys Arg Leu Leu Gln
            740                 745                 750

Gly Asp Thr Pro Val Arg Lys Leu Gln Ala Asn Lys Val Gln Gly
            755                 760                 765

Ser Arg Arg Arg Leu Arg Glu Gly Arg Ser Gln
    770                 775

<210> SEQ ID NO 8
<211> LENGTH: 807
<212> TYPE: PRT
<213> ORGANISM: Homo sapiens

<400> SEQUENCE: 8

Met Arg Leu Ser Pro Ala Pro Leu Lys Leu Ser Arg Thr Pro Ala Leu
1               5                   10                  15

Leu Ala Leu Ala Leu Pro Leu Ala Ala Ala Leu Ala Phe Ser Asp Glu
                20                  25                  30

Thr Leu Asp Lys Val Pro Lys Ser Glu Gly Tyr Cys Ser Arg Ile Leu
            35                  40                  45

Arg Ala Gln Gly Thr Arg Glu Gly Tyr Thr Glu Phe Ser Leu Arg
50                  55                  60

Val Glu Gly Asp Pro Asp Phe Tyr Lys Pro Gly Thr Ser Tyr Arg Val
65                  70                  75                  80

Thr Leu Ser Ala Ala Pro Pro Ser Tyr Phe Arg Gly Phe Thr Leu Ile
                85                  90                  95

Ala Leu Arg Glu Asn Arg Glu Gly Asp Lys Glu Asp His Ala Gly
            100                 105                 110

Thr Phe Gln Ile Ile Asp Glu Glu Thr Gln Phe Met Ser Asn Cys
        115                 120                 125

Pro Val Ala Val Thr Glu Ser Thr Pro Arg Arg Arg Thr Arg Ile Gln
130                 135                 140

Val Phe Trp Ile Ala Pro Pro Ala Gly Thr Gly Cys Val Ile Leu Lys
145                 150                 155                 160

Ala Ser Ile Val Gln Lys Arg Ile Ile Tyr Phe Gln Asp Glu Gly Ser
                165                 170                 175

Leu Thr Lys Lys Leu Cys Glu Gln Asp Ser Thr Phe Asp Gly Val Thr
            180                 185                 190

Asp Lys Pro Ile Leu Asp Cys Cys Ala Cys Gly Thr Ala Lys Tyr Arg
        195                 200                 205

Leu Thr Phe Tyr Gly Asn Trp Ser Glu Lys Thr His Pro Lys Asp Tyr
    210                 215                 220

Pro Arg Arg Ala Asn His Trp Ser Ala Ile Ile Gly Gly Ser His Ser
225                 230                 235                 240

Lys Asn Tyr Val Leu Trp Glu Tyr Gly Gly Tyr Ala Ser Glu Gly Val
                245                 250                 255

Lys Gln Val Ala Glu Leu Gly Ser Pro Val Lys Met Glu Glu Ile
            260                 265                 270

Arg Gln Gln Ser Asp Glu Val Leu Thr Val Ile Lys Ala Lys Ala Gln
        275                 280                 285

Trp Pro Ala Trp Gln Pro Leu Asn Val Arg Ala Ala Pro Ser Ala Glu
290                 295                 300

Phe Ser Val Asp Arg Thr Arg His Leu Met Ser Phe Leu Thr Met Met
305                 310                 315                 320

Gly Pro Ser Pro Asp Trp Asn Val Gly Leu Ser Ala Glu Asp Leu Cys
                325                 330                 335

Thr Lys Glu Cys Gly Trp Val Gln Lys Val Val Gln Asp Leu Ile Pro
            340                 345                 350

```
Trp Asp Ala Gly Thr Asp Ser Gly Val Thr Tyr Glu Ser Pro Asn Lys
            355                 360                 365

Pro Thr Ile Pro Gln Glu Lys Ile Arg Pro Leu Thr Ser Leu Asp His
370                 375                 380

Pro Gln Ser Pro Phe Tyr Asp Pro Gly Gly Ser Ile Thr Gln Val
385                 390                 395                 400

Ala Arg Val Val Ile Glu Arg Ile Ala Arg Lys Gly Glu Gln Cys Asn
                405                 410                 415

Ile Val Pro Asp Asn Val Asp Asp Ile Val Ala Asp Leu Ala Pro Glu
            420                 425                 430

Glu Lys Asp Glu Asp Asp Thr Pro Glu Thr Cys Ile Tyr Ser Asn Trp
        435                 440                 445

Ser Pro Trp Ser Ala Cys Ser Ser Ser Thr Cys Asp Lys Gly Lys Arg
    450                 455                 460

Met Arg Gln Arg Met Leu Lys Ala Gln Leu Asp Leu Ser Val Pro Cys
465                 470                 475                 480

Pro Asp Thr Gln Asp Phe Gln Pro Cys Met Gly Pro Gly Cys Ser Asp
                485                 490                 495

Glu Asp Gly Ser Thr Cys Thr Met Ser Glu Trp Ile Thr Trp Ser Pro
            500                 505                 510

Cys Ser Ile Ser Cys Gly Met Gly Met Arg Ser Arg Glu Arg Tyr Val
        515                 520                 525

Lys Gln Phe Pro Glu Asp Gly Ser Val Cys Thr Leu Pro Thr Glu Glu
    530                 535                 540

Thr Glu Lys Cys Thr Val Asn Glu Glu Cys Ser Pro Ser Ser Cys Leu
545                 550                 555                 560

Met Thr Glu Trp Gly Glu Trp Asp Glu Cys Ser Ala Thr Cys Gly Met
                565                 570                 575

Gly Met Lys Lys Arg His Arg Met Ile Lys Met Asn Pro Ala Asp Gly
            580                 585                 590

Ser Met Cys Lys Ala Glu Thr Ser Gln Ala Glu Lys Cys Met Met Pro
        595                 600                 605

Glu Cys His Thr Ile Pro Cys Leu Leu Ser Pro Trp Ser Glu Trp Ser
    610                 615                 620

Asp Cys Ser Val Thr Cys Gly Lys Gly Met Arg Thr Arg Gln Arg Met
625                 630                 635                 640

Leu Lys Ser Leu Ala Glu Leu Gly Asp Cys Asn Glu Asp Leu Glu Gln
                645                 650                 655

Val Glu Lys Cys Met Leu Pro Glu Cys Pro Ile Asp Cys Glu Leu Thr
            660                 665                 670

Glu Trp Ser Gln Trp Ser Glu Cys Asn Lys Ser Cys Gly Lys Gly His
        675                 680                 685

Val Ile Arg Thr Arg Met Ile Gln Met Glu Pro Gln Phe Gly Gly Ala
    690                 695                 700

Pro Cys Pro Glu Thr Val Gln Arg Lys Lys Cys Arg Ile Arg Lys Cys
705                 710                 715                 720

Leu Arg Asn Pro Ser Ile Gln Lys Leu Arg Trp Arg Glu Ala Arg Glu
                725                 730                 735

Ser Arg Arg Ser Glu Gln Leu Lys Glu Glu Ser Glu Gly Glu Gln Phe
            740                 745                 750

Pro Gly Cys Arg Met Arg Pro Trp Thr Ala Trp Ser Glu Cys Thr Lys
        755                 760                 765
```

-continued

Leu Cys Gly Gly Gly Ile Gln Glu Arg Tyr Met Thr Val Lys Lys Arg
770                     775                     780

Phe Lys Ser Ser Gln Phe Thr Ser Cys Lys Asp Lys Lys Glu Ile Arg
785                     790                     795                     800

Ala Cys Asn Val His Pro Cys
                805

<210> SEQ ID NO 9
<211> LENGTH: 3470
<212> TYPE: DNA
<213> ORGANISM: Homo sapiens

<400> SEQUENCE: 9

| | | | | |
|---|---|---|---|---|
| aaagctctgg | gccccaggga | ggaggctcag | cacagagagt | ggaaaacagc | agaggtgaca | 60 |
| gagcagccgt | gctcgaagcg | ttcctggagc | ccaagctctc | ctccacaggt | gaagacaggg | 120 |
| ccagcaggag | acaccatggg | gcacctctca | gccccacttc | acagagtgcg | tgtaccctgg | 180 |
| caggggcttc | tgctcacagc | ctcacttcta | accttctgga | acccgcccac | cactgcccag | 240 |
| ctcactactg | aatccatgcc | attcaatgtt | gcagagggga | aggaggttct | tctccttgtc | 300 |
| cacaatctgc | cccagcaact | ttttggctac | agctggtaca | aaggggaaag | agtggatggc | 360 |
| aaccgtcaaa | ttgtaggata | tgcaatagga | actcaacaag | ctaccccagg | gcccgcaaac | 420 |
| agcggtcgag | agacaatata | ccccaatgca | tccctgctga | tccagaacgt | cacccagaat | 480 |
| gacacaggat | tctacaccct | acaagtcata | aagtcagatc | ttgtgaatga | agaagcaact | 540 |
| ggacagttcc | atgtataccc | ggagctgccc | aagccctcca | tctccagcaa | caactccaac | 600 |
| cctgtggagg | acaaggatgc | tgtggccttc | acctgtgaac | ctgagactca | ggacacaacc | 660 |
| tacctgtggt | ggataaacaa | tcagagcctc | ccggtcagtc | ccaggctgca | gctgtccaat | 720 |
| ggcaacagga | ccctcactct | actcagtgtc | acaaggaatg | cacaggacc | ctatgagtgt | 780 |
| gaaatacaga | acccagtgag | tgcgaaccgc | agtgacccag | tcaccttgaa | tgtcacctat | 840 |
| ggcccggaca | cccccaccat | ttcccccttca | gacaccatt | accgtccagg | ggcaaacctc | 900 |
| agcctctcct | gctatgcagc | ctctaaccca | cctgcacagt | actcctggct | tatcaatgga | 960 |
| acattccagc | aaagcacaca | agagctcttt | atccctaaca | tcactgtgaa | taatagtgga | 1020 |
| tcctatacct | gccacgccaa | taactcagtc | actggctgca | acaggaccac | agtcaagacg | 1080 |
| atcatagtca | ctgagctaag | tccagtagta | gcaaagcccc | aaatcaaagc | cagcaagacc | 1140 |
| acagtcacag | gagataagga | ctctgtgaac | ctgacctgct | ccacaaatga | cactggaatc | 1200 |
| tccatccgtt | ggttcttcaa | aaaccagagt | ctcccgtcct | cggagaggat | gaagctgtcc | 1260 |
| cagggcaaca | ccaccctcag | cataaaccct | gtcaagaggg | aggatgctgg | gacgtattgg | 1320 |
| tgtgaggtct | tcaacccaat | cagtaagaac | caaagcgacc | ccatcatgct | gaacgtaaac | 1380 |
| tataatgctc | taccacaaga | aaatggcctc | tcacctgggg | ccattgctgg | cattgtgatt | 1440 |
| ggagtagtgg | ccctggttgc | tctgatagca | gtagccctgg | catgttttct | gcatttcggg | 1500 |
| aagaccggca | ggaccactcc | aatgacccac | taacaagat | gaatgaagtt | acttattcta | 1560 |
| ccctgaactt | tgaagcccag | caacccacac | aaccaacttc | agcctcccca | tccctaacag | 1620 |
| ccacagaaat | aatttattca | gaagtaaaaa | agcagtaatg | aaacctgtcc | tgctcactgc | 1680 |
| agtgctgatg | tatttcaagt | ctctccaccct | catcactagg | agattccttt | ccctgtagg | 1740 |
| ggtagagggg | tggggacaga | acaactttc | tcctactctt | ccttcctaat | aggcatctcc | 1800 |
| aggctgcctg | gtcactgccc | ctctctcagt | gtcaatagat | gaaagtacat | tgggagtctg | 1860 |

```
taggaaaccc aaccttcttg tcattgaaat ttggcaaagc tgactttggg aaagagggac    1920
cagaacttcc cctcccttcc cctttctcca acctggactt gttttaaact tgcctgttca    1980
gagcactcat tccttcccac ccccagtcct gtcctatcac tctaattcgg atttgccata    2040
gccttgaggt tatgtccttt tccattaagt acatgtgcca ggaaacaaga gagagagaaa    2100
gtaaaggcag taatgccttc tcctatttct ccaaagcctt gtgtgaactc accaaacaca    2160
agaaaatcaa atatataacc aatagtgaaa tgccacacct ttgtccactg tcagggttgt    2220
ctacctgtag gatcagggtc taagcacctt ggtgcttagc tagaatacca cctaatcctt    2280
ctggcaagcc tgtcttcaga gaacccacta gaagcaacta ggaaaatcac ttgccaaaat    2340
ccaaggcaat tcctgatgga aaatgcaaaa gcacatatat gttttaatat ctttatgggc    2400
tctgttcaag gcagtgctga gagggagggg ttatagcttc aggagggaac cagcttctga    2460
taaacacaat ctgctaggaa cttgggaaag gaatcagaga gctgcccttc agcgattatt    2520
taaattattg ttaaagaata cacaatttgg ggtattggga ttttttctcct tttctctgag    2580
acattccacc attttaattt ttgtaactgc ttatttatgt gaaaagggtt atttttactt    2640
agcttagcta tgtcagccaa tccgattgcc ttaggtgaaa gaaaccaccg aaatccctca    2700
ggtcccttgg tcaggagcct ctcaagattt ttttttgtcag aggctccaaa tagaaaataa    2760
gaaaaggttt tcttcattca tggctagagc tagatttaac tcagtttcta ggcacctcag    2820
accaatcatc aactaccatt ctattccatg tttgcacctg tgcattttct gtttgccccc    2880
attcactttg tcaggaaacc ttggcctctg ctaaggtgta tttggtcctt gagaagtggg    2940
agcaccctac agggacacta tcactcatgc tggtggcatt gtttacagct agaaagctgc    3000
actggtgcta atgccccttg gggaaatggg gctgtgagga ggaggattat aacttaggcc    3060
tagcctcttt taacagcctc tgaaatttat cttttcttct atggggtcta taatgtatc    3120
ttataataaa aaggaaggac aggaggaaga caggcaaatg tacttctcac ccagtcttct    3180
acacagatgg aatctctttg gggctaagag aaaggtttta ttctatattg cttacctgat    3240
ctcatgttag gcctaagagg ctttctccag gaggattagc ttggagttct ctatactcag    3300
gtacctctt  cagggttttc taaccctgac acggactgtg catactttcc ctcatccatg    3360
ctgtgctgtg ttatttaatt tttcctggct aagatcatgt ctgaattatg tatgaaaatt    3420
attctatgtt tttataataa aaataatata tcagacatcg aaaaaaaaaa              3470
```

<210> SEQ ID NO 10
<211> LENGTH: 764
<212> TYPE: DNA
<213> ORGANISM: Homo sapiens

<400> SEQUENCE: 10

```
ggcacgagga gcagagtcag ccagcatgac cgagcgccgc gtccccttct cgctcctgcg     60
gggccccagc tgggacccct tccgcgactg gtacccgcat agccgcctct tcgaccaggc    120
cttcgggctg cccccggctgc cggaggagtg gtcgcagtgg ttaggcggca gcagctggcc    180
aggctacgtg cgcccccctgc cccccgccgc catcgagagc cccgcagtgg ccgcgcccgc    240
ctacagccgc cgcgctcagcc ggcaactcag cagcggggtc tcggagatcc ggcacactgc    300
ggaccgctgg cgcgtgtccc tggatgtcaa ccacttcgcc ccggacgagc tgacggtcaa    360
gaccaaggat ggcgtggtgg agatcaccgg caagcacgag gagcggcagg acgagcatgg    420
ctacatctcc cggtgcttca cgcggaaata cacgctgccc ccggtgtgg acccccacca    480
agtttcctcc tccctgtccc ctgagggcac actgaccgtg gaggccccca tgcccaagct    540
```

```
agccacgcag tccaacgaga tcaccatccc agtcaccttc gagtcgcggg cccagcttgg    600
gggcccagaa gctgcaaaat ccgatgagac tgccgccaag taaagcctta gcccggatgc    660
ccacccctgc tgccgccact ggctgtgcct ccccgccac ctgtgtgttc ttttgataca     720
tttatcttct gttttctca aataaagttc aaagcaacca cctg                     764

<210> SEQ ID NO 11
<211> LENGTH: 2277
<212> TYPE: DNA
<213> ORGANISM: Homo sapiens

<400> SEQUENCE: 11
aatcgaaagt agactctttt ctgaagcatt tcctgggatc agcctgacca cgctccatac    60
tgggagaggc ttctgggtca aaggaccagt ctgcagaggg atcctgtggc tggaagcgag    120
gaggctccac acggccgttg cagctaccgc agccaggatc tgggcatcca ggcacggcca    180
tgacccctcc gaggctcttc tgggtgtggc tgctggttgc aggaacccaa ggcgtgaacg    240
atggtgacat gcggctggcc gatggggcg ccaccaacca gggccgcgtg gagatcttct    300
acagaggcca gtggggcact gtgtgtgaca acctgtggga cctgactgat gccagcgtcg    360
tctgccgggc cctgggcttc gagaacgcca cccaggctct gggcagagct gccttcgggc    420
aaggatcagg ccccatcatg ctggatgagg tccagtgcac gggaaccgag gcctcactgg    480
ccgactgcaa gtccctgggc tggctgaaga gcaactgcag gcacgagaga gacgctggtg    540
tggtctgcac caatgaaacc aggagcaccc acaccctgga cctctccagg gagctctcgg    600
aggcccttgg ccagatcttt gacagccagc ggggctgcga cctgtccatc agcgtgaatg    660
tgcagggcga ggacgccctg gcttctgtg ccacacggt catcctgact gccaacctgg    720
aggcccaggc cctgtggaag gagccgggca gcaatgtcac catgagtgtg gatgctgagt    780
gtgtgcccat ggtcagggac cttctcaggt acttctactc ccgaaggatt gacatcaccc    840
tgtcgtcagt caagtgcttc cacaagctgg cctctgccta tgggggccagg cagctgcagg    900 gctactgcgc aagcctcttt gccatcctcc tcccccagga cccctcgttc cagatgcccc    960
tggacctgta tgcctatgca gtggccacag gggacgccct gctggagaag ctctgcctac    1020
agttcctggc ctggaacttc gaggccttga cgcaggccga ggcctggccc agtgtcccca    1080
cagacctgct ccaactgctg ctgcccagga gcgacctggc ggtgcccagc gagctggccc    1140
tactgaaggc cgtggacacc tggagctggg gggagcgtgc ctcccatgag gaggtggagg    1200
gcttggtgga gaagatccgc ttccccatga tgctccctga ggagctcttt gagctgcagt    1260
tcaacctgtc cctgtactgg agccacgagg ccctgttcca agaagagact ctgcaggccc    1320
tggaattcca cactgtgccc ttccagttgc tggccggta caaaggcctg aacctcaccg    1380 aggatacccta caagccccgg atttacacct cgcccacctg gagtgccttt gtgacagaca    1440
gttcctggag tgcacggaag tcacaactgg tctatcagtc cagacggggg cctttggtca    1500
aatattcttc tgattacttc caagcccccct ctgactacag atactacccc taccagtcct    1560
tccagactcc acaacacccc agcttcctct tccaggacaa gagggtgtcc tggtccctgg    1620
tctacctccc caccatccag agctgctgga actacgggct ctcctgctcc tcggacgagc    1680
tccctgtcct gggcctcacc aagtctggcg gctcagatcg caccattgcc tacgaaaaca    1740
aagccctgat gctctgcgaa gggctcttcg tggcagacgt caccgatttc gagggctgga    1800
aggctgcgat tcccagtgcc ctggacacca acagctcgaa gagcacctcc tccttcccct    1860
```

```
gcccggcagg gcacttcaac ggcttccgca cggtcatccg ccccttctac ctgaccaact   1920
cctcaggtgt ggactagacg gcgtggccca agggtggtga gaaccggaga accccaggac   1980
gccctcactg caggctcccc tcctcggctt ccttcctctc tgcaatgacc ttcaacaacc   2040
ggccaccaga tgtcgcccta ctcacctgag cgctcagctt caagaaatta ctggaaggct   2100
tccactaggg tccaccagga gttctcccac cacctcacca gtttccaggt ggtaagcacc   2160
aggacgccct cgaggttgct ctgggatccc cccacagccc ctggtcagtc tgcccttgtc   2220
actggtctga ggtcattaaa attacattga ggttcctaca aaaaaaaaaa aaaaaaa     2277
```

<210> SEQ ID NO 12
<211> LENGTH: 529
<212> TYPE: DNA
<213> ORGANISM: Homo sapiens

<400> SEQUENCE: 12

```
cttctgtggc cagaggggac agcggaggag cccagtccac gatggcccgg tccctggtgt    60
gccttggtgt catcatcttg ctgtctgcct tctccggacc tggtgtcagg ggtggtccta   120
tgcccaagct ggctgaccgg aagctgtgtg cggaccagga gtgcagccac cctatctcca   180
tggctgtggc ccttcaggac tacatggccc ccgactgccg attcctgacc attcaccggg   240
gccaagtggt gtatgtcttc tccaagctga agggccgtgg gcggctcttc tggggaggca   300
gcgttcaggg agattactat ggagatctgg ctgctcgcct gggctatttc cccagtagca   360
ttgtccgaga ggaccagacc ctgaaacctg gcaaagtcga tgtgaagaca gacaaatggg   420
atttctactg ccagtgagct cagcctaccg ctggccctgc cgtttcccct ccttggcttt   480
atgcaaatac aatcagccca gtgcaaacgg aaaaaaaaaa aaaaaaaa               529
```

<210> SEQ ID NO 13
<211> LENGTH: 1202
<212> TYPE: DNA
<213> ORGANISM: Homo sapiens

<400> SEQUENCE: 13

```
gcggccgctg cacagccatg cccgggcaag aactcaggac gctgaatggc tctcagatgc    60
tcctggtgtt gctggtgctc tcgtggctgc cgcatggggg cgccctgtct ctggccgagg   120
cgagccgcgc aagtttcccg ggaccctcag agttgcacac cgaagactcc agattccgag   180
agttgcggaa acgctacgag gacctgctaa ccaggctgcg ggccaaccag agctgggaag   240
attcgaacac cgaccctcgtc ccggcccctg cagtccggat actcacgcca gaagtgcggc   300
tgggatccgg cggccacctg cacctgcgta tctctcgggc cgcccttccc gagggggctcc   360 ccgaggcctc ccgccttcac cgggctctgt tccggctgtc cccgacggcg tcaaggtcgt   420
gggacgtgac acgacctctg cggcgtcagc tcagccttgc aagacccccag cgcccgcgc   480 tgcacctgcg actgtcgccg ccgccgtcgc agtcggacca actgctggca gaatcttcgt   540
ccgcacggcc ccagctggag ttgcacttgc ggccgcaagc cgccaggggg cgccgcagag   600
cgcgtgcgcg caacggggac cactgtccgc tcgggcccgg gcgttgctgc cgtctgcaca   660
cggtccgcgc gtcgctggaa gacctgggct gggccgattg ggtgctgtcg ccacgggagg   720
tgcaagtgac catgtgcatc ggcgcgtgcc cgagccagtt ccgggcggca acatgcacg   780 cgcagatcaa gacgagcctg caccgcctga agcccgacac ggtgccagcg ccctgctgcg   840
tgcccgccaa ctacaatccc atggtgctca ttcaaaagac cgacaccggg gtgtcgctcc   900
agacctatga tgacttgtta gccaaagact gccactgcat atgagcagtc ctggtccttc   960
```

```
cactgtgcac ctgcgcgggg gaggcgacct cagttgtcct gccctgtgga atgggctcaa   1020
ggttcctgag acacccgatt cctgcccaaa cagctgtatt tatataagtc tgttatttat   1080
tattaattta ttggggtgac cttcttgggg actcgggggc tggtctgatg gaactgtgta   1140
tttatttaaa actctggtga taaaaataaa gctgtctgaa ctgttaaaaa aaaaaaaaaa   1200
aa                                                                  1202

<210> SEQ ID NO 14
<211> LENGTH: 1560
<212> TYPE: DNA
<213> ORGANISM: Homo sapiens

<400> SEQUENCE: 14
ctccctgtgt tggtggagga tgtctgcagc agcatttaaa ttctgggagg gcttggttgt     60
cagcagcagc aggaggaggc agagcacagc atcgtcggga ccagactcgt ctcaggccag    120
ttgcagcctt ctcagccaaa cgccgaccaa ggaaaactca ctaccatgag aattgcagtg    180
atttgctttt gcctcctagg catcacctgt gccataccag ttaaacaggc tgattctgga    240
agttctgagg aaaagcagaa tgctgtgtcc tctgaagaaa ccaatgactt taaacaagag    300
acccttccaa gtaagtccaa cgaaagccat gaccacatgg atgatatgga tgatgaagat    360
gatgatgacc atgtggacag ccaggactcc attgactcga acgactctga tgatgtagat    420
gacactgatg attctcacca gtctgatgag tctcaccatt ctgatgaatc tgatgaactg    480
gtcactgatt ttcccacgga cctgccagca accgaagttt tcactccagt tgtccccaca    540
gtagacacat atgatggccg aggtgatagt gtggtttatg gactgaggtc aaaatctaag    600
aagtttcgca gacctgacat ccagtaccct gatgctacag acgaggacat cacctcacac    660
atggaaagcg aggagttgaa tggtgcatac aaggccatcc ccgttgccca ggacctgaac    720
gcgccttctg attgggacag ccgtgggaag gacagttatg aaacgagtca gctggatgac    780
cagagtgctg aaacccacag ccacaagcag tccagattat ataagcggaa agccaatgat    840
gagagcaatg agcattccga tgtgattgat agtcaggaac tttccaaagt cagccgtgaa    900
ttccacagcc atgaatttca cagccatgaa gatatgctgg ttgtagaccc caaaagtaag    960
gaagaagata aacacctgaa atttcgtatt tctcatgaat tagatagtgc atcttctgag   1020
gtcaattaaa aggagaaaaa atacaatttc tcactttgca tttagtcaaa agaaaaaatg   1080
ctttatagca aaatgaaaga gaacatgaaa tgcttctttc tcagtttatt ggttgaatgt   1140
gtatctattt gagtctggaa ataactaatg tgtttgataa ttagtttagt ttgtggcttc   1200
atggaaactc cctgtaaact aaaagcttca gggttatgtc tatgttcatt ctatagaaga   1260
aatgcaaact atcactgtat tttaatattt gttattctct catgaataga aatttatgta   1320
gaagcaaaca aaatactttt acccacttaa aaagagaata taacatttta tgtcactata   1380
atcttttgtt ttttaagtta gtgtatattt tgttgtgatt atctttttgt ggtgtgaata   1440
aatcttttat cttgaatgta ataagaattt ggtggtgtca attgcttatt tgttttccca   1500
cggttgtcca gcaattaata aaacataacc tttttactg cctaaaaaaa aaaaaaaaaa    1560

<210> SEQ ID NO 15
<211> LENGTH: 2455
<212> TYPE: DNA
<213> ORGANISM: Homo sapiens

<400> SEQUENCE: 15

```

```
agagactcaa gatgattccc tttttaccca tgttttctct actattgctg cttattgtta      60
accctataaa cgccaacaat cattatgaca agatcttggc tcatagtcgt atcagggtc     120 gggaccaagg cccaaatgtc tgtgcccttc aacagatttt gggcaccaaa aagaaatact    180
tcagcacttg taagaactgg tataaaaagt ccatctgtgg acagaaaacg actgtgttat    240
atgaatgttg ccctggttat atgagaatgg aaggaatgaa aggctgccca gcagttttgc    300
ccattgacca tgtttatggc actctgggca tcgtgggagc caccacaacg cagcgctatt    360
ctgacgcctc aaaactgagg gaggagatcg agggaaaggg atccttcact tactttgcac    420
cgagtaatga ggcttgggac aacttggatt ctgatatccg tagaggtttg agagcaacg     480 tgaatgttga attactgaat gctttacata gtcacatgat aataagaga atgttgacca     540 aggacttaaa aaatggcatg attattcctt caatgtataa caatttgggg cttttcatta    600
accattatcc taatggggtt gtcactgtta attgtgctcg aatcatccat gggaaccaga    660
ttgcaacaaa tggtgttgtc catgtcattg accgtgtgct tacacaaatt ggtacctcaa    720
ttcaagactt cattgaagca gaagatgacc tttcatcttt tagagcagct gccatcacat    780
cggacatatt ggaggccctt ggaagagacg tcacttcac actctttgct cccaccaatg     840
aggcttttga gaaacttcca cgaggtgtcc tagaaaggat catgggagac aaagtggctt    900
ccgaagctct tatgaagtac cacatcttaa atactctcca gtgttctgag tctattatgg    960
gaggagcagt ctttgagacg ctggaaggaa atacaattga gataggatgt gacggtgaca   1020
gtataacagt aaatggaatc aaaatggtga acaaaaagga tattgtgaca aataatggtg   1080
tgatccattt gattgatcag gtcctaattc ctgattctgc caaacaagtt attgagctgg   1140
ctggaaaaca gcaaccacc ttcacggatc ttgtggccca attaggcttg gcatctgctc     1200
tgaggccaga tggagaatac actttgctgg cacctgtgaa taatgcattt tctgatgata   1260
ctctcagcat ggatcagcgc ctccttaaat taattctgca gaatcacata ttgaaagtaa   1320
aagttggcct taatgagctt tacaacgggc aaatactgga aaccatcgga ggcaaacagc   1380
tcagagtctt cgtatatcgt acagctgtct gcattgaaaa ttcatgcatg gagaaaggga   1440
gtaagcaagg gagaaacggt gcgattcaca tattccgcga gatcatcaag ccagcagaga   1500
aatccctcca tgaaaagtta aaacaagata gcgctttag caccttcctc agcctacttg     1560
aagctgcaga cttgaaagag ctcctgacac aacctggaga ctggacatta tttgtgccaa   1620
ccaatgatgc ttttaaggga atgactagtg aagaaaaga aattctgata cgggacaaaa     1680
atgctcttca aaacatcatt ctttatcacc tgacaccagg agttttcatt ggaaaaggat   1740
ttgaacctgg tgttactaac attttaaaga ccacacaagg aagcaaaatc tttctgaaag   1800
aagtaaatga tacacttctg gtgaatgaat tgaaatcaaa agaatctgac atcatgacaa   1860
caaatggtgt aattcatgtt gtagataaac tcctctatcc agcagacaca cctgttggaa   1920
atgatcaact gctggaaata cttaataaat taatcaaata catccaaatt aagtttgttc   1980
gtggtagcac cttcaaagaa atccccgtga ctgtctataa gccaattatt aaaaaataca   2040
ccaaaatcat tgatggagtg cctgtggaaa taactgaaaa agagacacga gaagaacgaa   2100
tcattacagg tcctgaaata aaatacacta ggatttctac tggaggtgga aaacagaag    2160 aaactctgaa gaaattgtta caagaagagg tcaccaaggt caccaaattc attgaaggtg   2220
gtgatggtca tttatttgaa gatgaagaaa ttaaaagact gcttcaggga gacacacccg   2280
tgaggaagtt gcaagccaac aaaaaagttc aaggatctag aagacgatta agggaaggtc   2340
gttctcagtg aaaatccaaa aaccagaaaa aaatgtttat acaaccctaa gtcaataacc   2400
```

```
tgaccttaga aaattgtgag agccaagttg acttcaggaa ctgaaacatc agcac      2455
```

<210> SEQ ID NO 16
<211> LENGTH: 5154
<212> TYPE: DNA
<213> ORGANISM: Homo sapiens

<400> SEQUENCE: 16

```
gcaaaatcag ccctccctcc tcccgctcct tcgccgcggc cctcccctcc tcgcgctgct      60
ctcgttcgct tggctcagct cagctcagct cagcgcagct ccgcggccgc caagccgagg     120
cgggcacggt ctccgagtcg cggacgccag ctccgagctc cctctctccg ccgcgcctcc     180
gccaggtcgc gccttcgtcg ggaccacttc gggcaggagt cgcgtggcga aggcctgcgg     240
ccgcggcaca aagttggggg ccgcgaagat gaggctgtcc ccggcgcccc tgaagctgag     300
ccggactccg gcactgctgg ccctggcgct gccctggcc gcggcgctgg ccttctccga      360
cgagaccctg acaaagtgc ccaagtcaga gggctactgc agccgtatcc tgcgcgccca      420
gggcacgcgg cgcgagggct acaccgagtt cagcctccgc gtggagggcg accccgactt     480
ctacaagccg ggaaccagct accgcgtaac actttcagct gctcctccct cctacttcag     540
aggattcaca ttaattgccc tcagagagaa cagagagggt gataaggaag aagaccatgc     600
tgggaccttc cagatcatag acgaagaaga aactcagttt atgagcaatt gccctgttgc     660
agtcactgaa agcactccac ggaggaggac ccggatccag gtgttttgga tagcaccacc     720
agcgggaaca ggctgcgtga ttctgaaggc cagcatcgta caaaaacgca ttatttattt     780
tcaagatgag ggctctctga ccaagaaact tgtgaacaa gattccacat ttgatggggt      840
gactgacaaa cccatcttag actgctgtgc ctgcggaact gccaagtaca gactcacatt     900
ttatgggaat tggtccgaga agacacaccc aaaggattac cctcgtcggg ccaaccactg     960
gtctgcgatc atcggaggat cccactccaa gaattatgta ctgtgggaat atggaggata    1020
tgccagcgaa ggcgtcaaac aagttgcaga attgggctca cccgtgaaaa tggaggaaga    1080
aattcgacaa cagagtgatg aggtcctcac cgtcatcaaa gccaaagccc aatggccagc    1140
ctggcagcct ctcaacgtga gagcagcacc ttcagctgaa ttttccgtgg acagaacgcg    1200
ccatttaatg tccttcctga ccatgatggg ccctagtccc gactggaacg taggcttatc    1260
tgcagaagat ctgtgcacca aggaatgtgg ctgggtccag aaggtggtgc aagacctgat    1320
tccctgggac gctggcaccg acagcggggt gacctatgag tcacccaaca aacccaccat    1380
tccccaggag aaaatccggc ccctgaccag cctggaccat cctcagagtc ctttctatga    1440
cccagagggt gggtccatca ctcaagtagc cagagttgtc atcgagagaa tcgcacggaa    1500
gggtgaacaa tgcaatattg tacctgacaa tgtcgatgat attgtagctg acctggctcc    1560
agaagagaaa gatgaagatg acacccctga acctgcatc tactccaact ggtccccatg     1620
gtccgcctgc agctcctcca cctgtgacaa aggcaagagg atgcgacagc gcatgctgaa    1680
agcacagctg gacctcagcg tcccctgccc tgacacccag gacttccagc cctgcatggg    1740
ccctggctgc agtgacgaag acggctccac ctgcaccatg tccgagtgga tcacctggtc    1800
gccctgcagc atctcctgcg gcatgggcat gaggtcccgg gagaggtatg tgaagcagtt    1860
cccggaggac ggctccgtgt gcacgctgcc cactgaggaa acggagaagt gcacggtcaa    1920
cgaggagtgc tctcccagca gctgcctgat gaccgagtgg ggcgagtggg acgagtgcag    1980
cgccacctgc ggcatgggca tgaagaagcg gcaccgcatg atcaagatga accccgcaga    2040
```

```
tggctccatg tgcaaagccg agacatcaca ggcagagaag tgcatgatgc cagagtgcca    2100
caccatccca tgcttgctgt ccccatggtc cgagtggagt gactgcagcg tgacctgcgg    2160
gaagggcatg cgaacccgac agcggatgct caagtctctg gcagaacttg gagactgcaa    2220
tgaggatctg gagcaggtgg agaagtgcat gctccctgaa tgccccattg actgtgagct    2280
caccgagtgg tcccagtggt cggaatgtaa caagtcatgt gggaaaggcc acgtgattcg    2340
aacccggatg atccaaatgg agcctcagtt tggaggtgca ccctgcccag agactgtgca    2400
gcgaaaaaag tgccgcatcc gaaaatgcct tcgaaatcca tccatccaaa agctacgctg    2460
gagggaggcc cgagagagcc ggcggagtga gcagctgaag gaagagtctg aaggggagca    2520
gttcccaggt tgtaggatgc gcccatggac ggcctggtca gaatgcacca aactgtgcgg    2580
aggtggaatt caggaacgtt acatgactgt aaagaagaga ttcaaaagct cccagtttac    2640
cagctgcaaa gacaagaagg agatcagagc atgcaatgtt catccttgtt agcaagggta    2700
cgagttcccc agggctgcac tctagattcc agagtcacca atggctggat tatttgcttg    2760
tttaagacaa tttaaattgt gtacgctagt tttcattttt gcagtgtggt tcgcccagta    2820
gtcttgtgga tgccagagac atcctttctg aatacttctt gatgggtaca ggctgagtgg    2880
ggcgccctca cctccagcca gcctcttcct gcagaggagt agtgtcagcc accttgtact    2940
aagctgaaac atgtccctct ggagcttcca cctggccagg gaggacggag actttgacct    3000
actccacatg gagaggcaac catgtctgga agtgactatg cctgagtccc agggtgcggc    3060
aggtaggaaa cattcacaga tgaagacagc agattcccca cattctcatc tttggcctgt    3120
tcaatgaaac cattgtttgc ccatctcttc ttagtggaac tttaggtctc ttttcaagtc    3180
tcctcagtca tcaatagttc ctggggaaaa acagagctgg tagacttgaa gaggagcatt    3240
gatgttgggt ggcttttgtt ctttcactga gaaattcgga atacatttgt ctcacccctg    3300
atattggttc ctgatgcccc cccaacaaaa ataaataaat aaattatggc tgctttatt    3360 aaaatataagg tagctagttt ttacacctga gataaataat aagcttagag tgtatttttc    3420
ccttgctttt gggggttcag aggagtatgt acaattcttc tgggaagcca gccttctgaa    3480 cttttttggta ctaaatcctt attggaacca agacaaagga agcaaaattg gtctctttag    3540
agaccaattt gcctaaattt taaaatcttc ctacacacat ctagacgttc aagtttgcaa    3600
atcagttttt agcaagaaaa cattttttgct atacaaacat tttgctaagt ctgcccaaag    3660 ccccccaat gcattccttc aacaaaatac aatctctgta ctttaaagtt attttagtca    3720
tgaaatttta tatgcagaga gaaaagtta ccgagacaga aaacaaatct aagggaaagg    3780
aatattatgg gattaagctg agcaagcaat tctggtggaa agtcaaacct gtcagtgctc    3840
cacaccaggg ctgtggtcct cccagacatg cataggaatg ccacaggtt tacactgcct    3900 tcccagcaat tataagcaca ccagattcag ggagactgac caccaaggga tagtgtaaaa    3960
ggacattttc tcagttgggt ccatcagcag ttttttcttcc tgcatttatt gttgaaaact    4020
attgtttcat ttcttctttt ataggcctta ttactgctta atccaaatgt gtaccattgg    4080
tgagacacat acaatgctct gaatacacta cgaatttgta ttaaacacat cagaatattt    4140
ccaaatacaa catagtatag tcctgaatat gtacttttaa cacaagagag actattcaat    4200
aaaaactcac tgggtctttc atgtctttaa gctaagtaag tgttcagaag gttcttttttt    4260 atattgtcct ccacctccat cattttcaat aaaagatagg gcttttgctc ccttgttctt    4320
ggagggacca ttattacatc tctgaactac cctttgtatcc aacatgtttt aaatccttaa    4380
atgaattgct ttctcccaaa aaaagcacaa tataaagaaa cacaagattt aattattttt    4440
```

```
ctacttgggg ggaaaaaagt cctcatgtag aagcacccac ttttgcaatg ttgttctaag      4500
ctatctatct aactctcagc ccatgataaa gttccttaag ctggtgattc ctaatcaagg      4560
acaagccacc ctagtgtctc atgtttgtat ttggtcccag ttgggtacat tttaaaatcc      4620
tgattttgga gacttaaaac caggttaatg gctaagaatg ggtaacatga ctcttgttgg      4680
attgttattt tttgtttgca atggggaatt tataagaagc atcaagtctc tttcttacca      4740
aagtcttgtt aggtggttta tagttctttt ggctaacaaa tcattttgga aataaagatt      4800
ttttactaca aaaatgaaat ttgtttggac ttccacttga gacagtaaag agagtattag      4860
acacccagta aaaactgcca tataaagaag ttgtaattgt ttgttgtgta tgtattttt       4920 tcaatgccaa accagctgtg atccaattta catccacatt ttaggtccaa cagcaagaag      4980
ttcagagaga gatttcccaa ccagacattg ggtcactcac tggtcacctt gccagtgcat      5040
tttattagaa gggaatctgt tgtagcaaat gggaataaac ctgggtttct atagacccag      5100
aactgaaaaa ataaacatcg tgctgttttt aatttgaaaa aaaaaaaaaa aaaa           5154
```